(12) United States Patent
Chatterjee et al.

(10) Patent No.: US 11,891,619 B2
(45) Date of Patent: Feb. 6, 2024

(54) ADENO-ASSOCIATED VIRUS COMPOSITIONS FOR RESTORING F8 GENE FUNCTION AND METHODS OF USE THEREOF

(71) Applicants: City of Hope, Duarte, CA (US); Homology Medicines, Inc., Bedford, MA (US)

(72) Inventors: Saswati Chatterjee, Altadena, CA (US); Laura Jane Smith, Bedford, MA (US); Jeff Lynn Ellsworth, Lexington, MA (US); Hillard Rubin, Northborough, MA (US); Jason Boke Wright, Bedford, MA (US); James Anthony McSwiggen, Arlington, MA (US)

(73) Assignees: City of Hope, Duarte, CA (US); Homology Medicines, Inc., Bedford, MA (US)

( * ) Notice: Subject to any disclaimer, the term of this patent is extended or adjusted under 35 U.S.C. 154(b) by 2 days.

(21) Appl. No.: 17/654,300

(22) Filed: Mar. 10, 2022

(65) Prior Publication Data

US 2022/0333138 A1 Oct. 20, 2022

Related U.S. Application Data

(62) Division of application No. 16/279,688, filed on Feb. 19, 2019, now Pat. No. 11,306,329.

(60) Provisional application No. 62/672,385, filed on May 16, 2018, provisional application No. 62/632,919, filed on Feb. 20, 2018, provisional application No. 62/632,300, filed on Feb. 19, 2018.

(51) Int. Cl.
*C12N 15/86* (2006.01)
*C12N 15/90* (2006.01)
*C12N 7/00* (2006.01)

(52) U.S. Cl.
CPC .............. *C12N 15/907* (2013.01); *C12N 7/00* (2013.01); *C12N 15/86* (2013.01); *C12N 2710/10042* (2013.01); *C12N 2710/10043* (2013.01); *C12N 2710/10061* (2013.01)

(58) Field of Classification Search
CPC ........ C12N 15/907; C12N 15/86; C12N 7/00; C12N 2710/10042; C12N 2710/10043; C12N 2710/10061
See application file for complete search history.

(56) References Cited

U.S. PATENT DOCUMENTS

| | | |
|---|---|---|
| 5,252,479 A | 10/1993 | Srivastava |
| 5,474,935 A | 12/1995 | Chatterjee et al. |
| 5,589,377 A | 12/1996 | Lebkowski et al. |
| 5,622,856 A | 4/1997 | Natsoulis |
| 5,650,309 A | 7/1997 | Wong-Staal et al. |
| 5,753,500 A | 5/1998 | Shenk et al. |
| 5,780,447 A | 7/1998 | Nienhuis |
| 5,895,759 A | 4/1999 | Strauss et al. |
| 6,025,195 A | 2/2000 | Sandig et al. |
| 6,153,436 A | 11/2000 | Hermonat et al. |
| 6,156,303 A | 12/2000 | Russell et al. |
| 6,180,613 B1 | 1/2001 | Kaplitt et al. |
| 6,238,914 B1 | 5/2001 | Boyce |
| 6,268,212 B1 | 7/2001 | Simonet |
| 6,329,181 B1 | 12/2001 | Xiao et al. |
| 6,338,962 B1 | 1/2002 | Boyce |
| 6,387,670 B1 | 5/2002 | Leblois-Prehaud et al. |
| 6,610,906 B1 | 8/2003 | Kurachi et al. |
| 6,759,237 B1 | 7/2004 | Wilson et al. |
| 6,919,209 B1 | 7/2005 | Chatterjee et al. |
| 6,924,128 B2 | 8/2005 | Allen |
| 6,936,243 B2 | 8/2005 | Snyder et al. |
| 6,936,466 B2 | 8/2005 | Feldhaus |
| 6,953,690 B1 | 10/2005 | Gao et al. |
| 6,984,517 B1 | 1/2006 | Chiorini et al. |
| 7,001,764 B2 | 2/2006 | Little et al. |
| 7,022,519 B2 | 4/2006 | Gao et al. |
| 7,056,502 B2 | 6/2006 | Hildinger et al. |
| 7,091,029 B2 | 8/2006 | Hwang |
| 7,094,604 B2 | 8/2006 | Snyder et al. |

(Continued)

FOREIGN PATENT DOCUMENTS

| | | |
|---|---|---|
| EP | 746624 A1 | 12/1996 |
| WO | 1996008560 A1 | 3/1996 |

(Continued)

OTHER PUBLICATIONS

*Homo sapiens* coagulation factor VIII (F8), RefSeqGene on chromosome X NCBI Reference Sequence: NG_011403.1; 2018. Searched Apr. 15, 2022 <https://www.ncbi.nlm.nih.gov/nuccore/224586932?sat=46&satkey=166719631>.

(Continued)

*Primary Examiner* — Nancy J Leith
*Assistant Examiner* — Khaleda B Hasan
(74) *Attorney, Agent, or Firm* — Mintz, Levin, Cohn, Ferris, Glovsky and Popeo, P.C.

(57) ABSTRACT

Provided herein are adeno-associated virus (AAV) compositions that can restore F8 gene function in a cell without co-transducing or co-administering an exogenous nuclease or a nucleotide sequence that encodes an exogenous nuclease. Also provided are methods of using the AAV compositions to correct an F8 gene mutation and/or treat a disease or disorder associated with an F8 gene mutation. Packaging systems for making the adeno-associated virus compositions are also provided.

21 Claims, 28 Drawing Sheets

Specification includes a Sequence Listing.

(56) References Cited

U.S. PATENT DOCUMENTS

| | | |
|---|---|---|
| 7,148,341 B2 | 12/2006 | Kleinschmidt et al. |
| 7,157,571 B2 | 1/2007 | Wang et al. |
| 7,172,893 B2 | 2/2007 | Rabinowitz et al. |
| 7,179,903 B2 | 2/2007 | McArthur et al. |
| 7,198,951 B2 | 4/2007 | Gao et al. |
| 7,220,577 B2 | 5/2007 | Zolotukhin |
| 7,235,393 B2 | 6/2007 | Gao et al. |
| 7,259,151 B2 | 8/2007 | Arbetman et al. |
| 7,282,199 B2 | 10/2007 | Gao et al. |
| 7,351,813 B2 | 4/2008 | Miao et al. |
| 7,465,583 B2 | 12/2008 | Samulski et al. |
| 7,482,156 B2 | 1/2009 | Arroyo et al. |
| 7,588,772 B2 | 9/2009 | Kay et al. |
| 7,749,492 B2 | 7/2010 | Bartlett et al. |
| 7,790,154 B2 | 9/2010 | Samulski et al. |
| 7,906,111 B2 | 3/2011 | Wilson et al. |
| 8,030,065 B2 | 10/2011 | Gray |
| 8,067,156 B2 | 11/2011 | Kaplitt et al. |
| 8,163,543 B2 | 4/2012 | Urabe et al. |
| 8,168,425 B2 | 5/2012 | Gray |
| 8,241,622 B2 | 8/2012 | Englehardt et al. |
| 8,283,151 B2 | 10/2012 | Schmidt et al. |
| 8,298,818 B2 | 10/2012 | Boye et al. |
| 8,476,418 B2 | 7/2013 | Mueller et al. |
| 8,524,446 B2 | 9/2013 | Gao et al. |
| 8,628,966 B2 | 1/2014 | Chatterjee et al. |
| 8,632,764 B2 | 1/2014 | Xiao et al. |
| 8,716,461 B2 | 5/2014 | Delwart et al. |
| 8,802,620 B2 * | 8/2014 | Chtourou ............... A61P 7/02 514/14.1 |
| 8,846,387 B2 | 9/2014 | Russell et al. |
| 8,846,389 B2 | 9/2014 | Chiorini et al. |
| 8,926,958 B2 | 1/2015 | Shah et al. |
| 8,999,678 B2 | 4/2015 | Vandenberghe et al. |
| 8,999,948 B2 | 4/2015 | Tubert et al. |
| 9,150,882 B2 | 10/2015 | Kay et al. |
| 9,169,299 B2 | 10/2015 | Lisowski et al. |
| 9,169,494 B2 | 10/2015 | Hewitt et al. |
| 9,193,956 B2 | 11/2015 | Schaffer et al. |
| 9,217,155 B2 | 12/2015 | Gao et al. |
| 9,222,105 B2 | 12/2015 | Cost et al. |
| 9,402,919 B2 | 8/2016 | Roeth et al. |
| 9,408,904 B2 | 8/2016 | Wright et al. |
| 9,409,953 B2 | 8/2016 | Asokan et al. |
| 9,441,244 B2 | 9/2016 | Schaffer et al. |
| 9,617,548 B2 | 4/2017 | Chuah et al. |
| 9,764,045 B2 | 9/2017 | Nathwani et al. |
| 9,783,824 B2 | 10/2017 | Kay et al. |
| 9,840,719 B2 | 12/2017 | High et al. |
| 9,890,396 B2 | 2/2018 | Chatterjee et al. |
| 2003/0129203 A1 | 7/2003 | Vega et al. |
| 2003/0130221 A1 | 7/2003 | High et al. |
| 2004/0086485 A1 | 5/2004 | Aguilar-Cordova |
| 2004/0235174 A1 | 11/2004 | Grimm et al. |
| 2005/0112765 A1 | 5/2005 | Li et al. |
| 2009/0191597 A1 | 7/2009 | Samulski et al. |
| 2009/0215879 A1 | 8/2009 | Diprimio et al. |
| 2010/0297084 A1 | 11/2010 | Bennett et al. |
| 2012/0046349 A1 | 2/2012 | Bell et al. |
| 2012/0093772 A1 | 4/2012 | Horsager et al. |
| 2012/0244127 A1 | 9/2012 | Lipschutz et al. |
| 2013/0023033 A1 | 1/2013 | Wilson et al. |
| 2013/0189225 A1 | 7/2013 | Voit et al. |
| 2013/0310443 A1 | 11/2013 | Srivastava et al. |
| 2013/0323226 A1 | 12/2013 | Wilson et al. |
| 2014/0037585 A1 | 2/2014 | Wright et al. |
| 2014/0050701 A1 | 2/2014 | Zhong et al. |
| 2014/0107185 A1 | 4/2014 | Maclaren et al. |
| 2014/0271550 A1 | 9/2014 | Rabinowitz et al. |
| 2014/0336245 A1 | 11/2014 | Mingozzi et al. |
| 2014/0359799 A1 | 12/2014 | Wang et al. |
| 2015/0023924 A1 | 1/2015 | High et al. |
| 2015/0024467 A1 | 1/2015 | Sheldon et al. |
| 2015/0065562 A1 | 3/2015 | Yazicioglu et al. |
| 2015/0079038 A1 | 3/2015 | Deverman et al. |
| 2015/0110762 A1 | 4/2015 | Holmes et al. |
| 2015/0111955 A1 | 4/2015 | High et al. |
| 2015/0184197 A1 | 7/2015 | Davidson et al. |
| 2015/0238550 A1 | 8/2015 | McCown et al. |
| 2015/0306250 A1 * | 10/2015 | Laterza ............... C07K 14/755 435/375 |
| 2015/0315610 A1 | 11/2015 | Nishie et al. |
| 2015/0352228 A1 | 12/2015 | Torbett et al. |
| 2015/0374803 A1 | 12/2015 | Wolfe |
| 2015/0376240 A1 | 12/2015 | Cronin et al. |
| 2016/0000887 A1 | 1/2016 | Wilson et al. |
| 2016/0017295 A1 | 1/2016 | Schaffer et al. |
| 2016/0032319 A1 | 2/2016 | Wright et al. |
| 2016/0123990 A1 | 5/2016 | High et al. |
| 2016/0175365 A1 | 6/2016 | Golden |
| 2016/0229904 A1 | 8/2016 | Xiao et al. |
| 2017/0081680 A1 * | 3/2017 | Chatterjee ............ C12N 15/907 |
| 2017/0119906 A1 | 5/2017 | Riley |
| 2017/0198265 A1 | 7/2017 | Chatterjee et al. |
| 2017/0326256 A1 | 11/2017 | Doering et al. |
| 2018/0163227 A1 | 6/2018 | Chatterjee et al. |
| 2018/0282765 A1 | 10/2018 | Chatterjee et al. |

FOREIGN PATENT DOCUMENTS

| | | |
|---|---|---|
| WO | 1998009524 A1 | 3/1998 |
| WO | 1998021349 A1 | 5/1998 |
| WO | 1998027207 A1 | 6/1998 |
| WO | 1998028417 A1 | 7/1998 |
| WO | 1999003981 A1 | 1/1999 |
| WO | 1999018227 A1 | 4/1999 |
| WO | 1999055564 A1 | 11/1999 |
| WO | 1999064569 A1 | 12/1999 |
| WO | 2001036620 A2 | 5/2001 |
| WO | 2002066611 A2 | 8/2002 |
| WO | 2005111220 A2 | 11/2005 |
| WO | 2006096815 A2 | 9/2006 |
| WO | 2007019646 A1 | 2/2007 |
| WO | 2008021140 A2 | 2/2008 |
| WO | 2009043936 A1 | 4/2009 |
| WO | 2009130208 A1 | 10/2009 |
| WO | 2009134681 A2 | 11/2009 |
| WO | 2011012724 A1 | 2/2011 |
| WO | 2011038187 A1 | 3/2011 |
| WO | 2014064277 A1 | 5/2014 |
| WO | 2014089212 A1 | 6/2014 |
| WO | 2014193716 A2 | 12/2014 |
| WO | 2015143177 A1 | 9/2015 |
| WO | 2015164723 A1 | 10/2015 |
| WO | 2016049230 A1 | 3/2016 |
| WO | WO-2016049230 A1 * | 3/2016 ......... A61K 48/0008 |
| WO | 2016097218 A1 | 6/2016 |
| WO | 2016097219 A1 | 6/2016 |
| WO | 2016100575 A1 | 6/2016 |
| WO | 2016145757 A1 | 9/2016 |
| WO | 2017100551 A1 | 6/2017 |
| WO | 2018126116 A1 | 7/2018 |
| WO | 2018129586 A1 | 7/2018 |
| WO | 2019010091 A1 | 1/2019 |

OTHER PUBLICATIONS

Wu et al., "In situ genetic correction of F8 intron 22 inversion in hemophilia A patient-specific iPSCs," Scientific Reports. 2016; 6(8865):11 pages.

Barzel et al., "Promoterless gene targeting without nucleases ameliorates haemophilia B in mice," Nature. 2015;517:360-64.

Clark et al., "GenBank," Nucleic Acids Res. 2016;44(Database issue):D67-72.

Farré et al., "Identification of patterns in biological sequences at the ALGGEN server: PROMO and MALGEN," Nucleic Acids Res. 2003;31(13):3651-653.

Frock et al., "Genome-wide detection of DNA double-stranded breaks induced by engineered nucleases," Nat Biotechnol. 2015;33(2):179-86.

(56) References Cited

OTHER PUBLICATIONS

Griffith et al., "ORegAnno: an open-access community-driven resource for regulatory annotation," Nucleic Acids Res. 2008; 36(Database issue):D107-13.
Hacein-Bey-Abina et al., "Insertional oncogenesis in 4 patients after retrovirus-mediated gene therapy of SCID-X1," J Clin Invest. 2008;118(9):3132-142.
Khan et al., "JASPAR 2018: update of the open-access database of transcription factor binding profiles and its web framework," Nucleic Acids Res. 2018;46(D1):D260-66.
Kramer et al., "In vitro and in vivo comparative study of chimeric liver-specific promoters," Mol Therapy. 2003; 7(3):375-85.
Landrum et al., "ClinVar: public archive of relationships among sequence variation and human phenotype," Nucleic Acids Res. 2014;42(Database issue):D980-5.
Lu et al., "A mini-intronic plasmid (MIP): a novel robust transgene expression vector in vivo and in vitro," Mol Ther. 2013;21(5):954-63.
Lu et al., "A 5' Noncoding Exon Containing Engineered Intron Enhances Transgene Expression from Recombinant AAV Vectors in vivo," Hum Gene Ther. 2017;28(1):125-34.
Mauro, "A critical analysis of codon optimization in human therapeutics," Trends Mol Med. 2014;20(11):604-13.
MacDonald et al., "The Database of Genomic Variants: a curated collection of structural variation in the human genome," Nucleic Acids Res. 2014;42(Database issue):D986-92.
Messeguer et al., "PROMO: detection of known transcription regulatory elements using species-tailored searches," Bioinformatics. 2002;18(2):333-34.
Nair et al., "A simple practice guide for dose conversion between animals and human," J. Basic Clin. Pharm. 2016;7(2):27-31.
PCT International Search Report and Written Opinion from PCT/US2019/18502 dated Jun. 28, 2019.
Rando et al., "Genome-wide views of chromatin structure," Annu Rev Biochem. 2009;78:245-71.
Sabo et al., "Genome-scale mapping of DNase I sensitivity in vivo using tiling DNA microarrays," Nat Methods. 2006;3(7):511-18.
Savy et al., "Impact of Inverted Terminal Repeat Integrity on rAAV8 Production Using the Baculovirus/Sf9 Cells System," Human Gene Therapy Methods. 2017;28(5):277-89.
Sherry et al., "dbSNP: the NCBI database of genetic variation," Nucleic Acids Res. 2001;29(1):308-11.
Sibley et al., "Lessons from non-canonical splicing," Nat Rev Genet. 2016; 17(7):407-21.
VandenDreissche et al., "Hitting the target without pulling the trigger," The American Society of Gene & Cell Therapy. 2015;23(1):4-6.
Khan et al., "Engineering of human pluripotent stem cells by AAV-mediated gene targeting," Mol Ther. 2010; 18(6):1192-9.
McIntosh et al., "Therapeutic levels of FVIII following a single peripheral vein administration of rAAV vector encoding a novel human factor VIII variant," Blood. 2013; 121(17):3335-44.
Park et al., "Functional Correction of Large Factor VIII Gene Chromosomal Inversions in Hemophilia A Patient-Derived IPSCs Using CRISPR-Cas9," Cell Stem Cell. 2015; 17(2):213-20.
Smith et al., "Stem cell-derived clade F AAVs mediate high-efficiency homologous recombination-based genome editing," Proc Natl Acad Sci U S A. 2018; 115(31):E7379-E7388.

\* cited by examiner

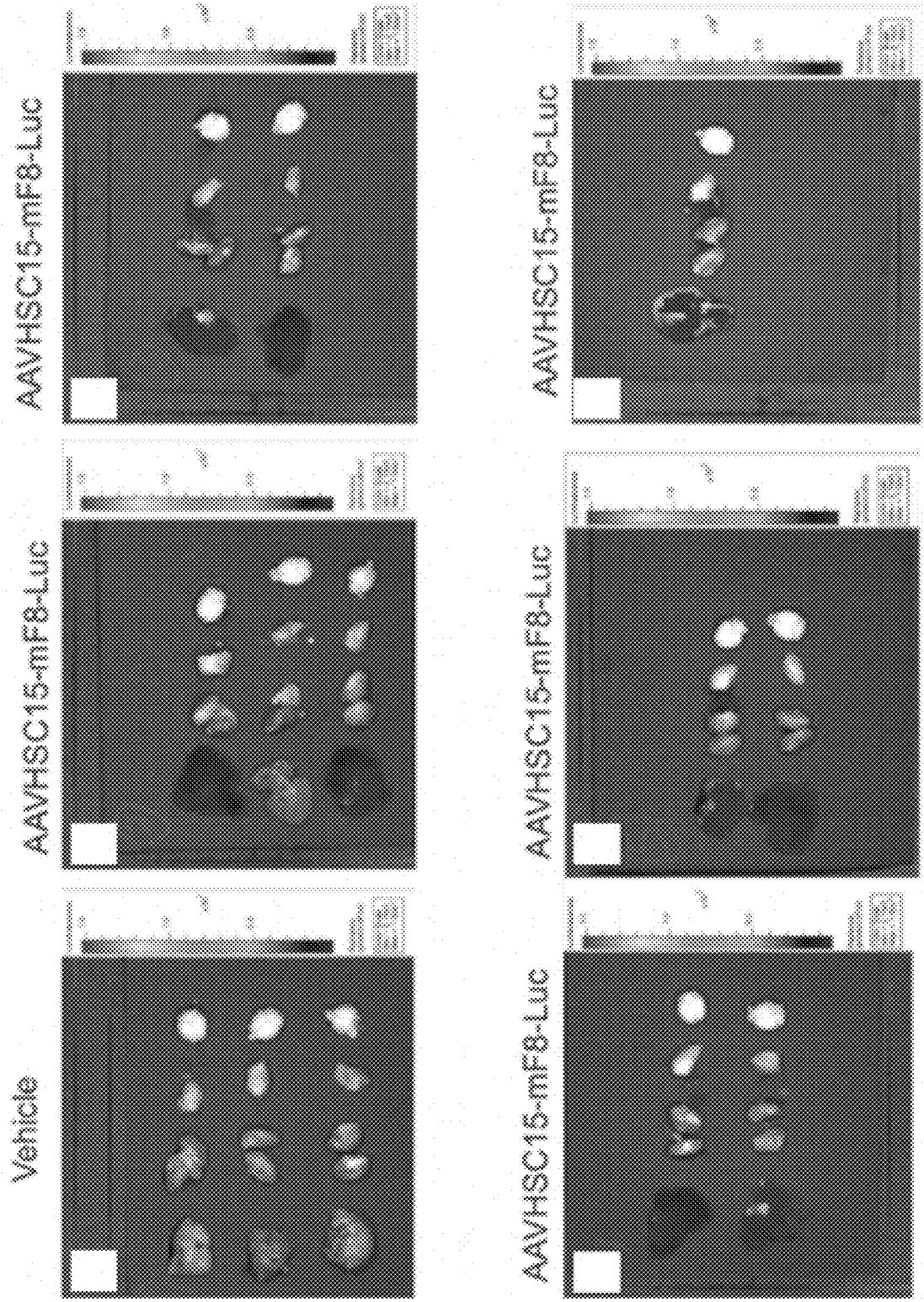

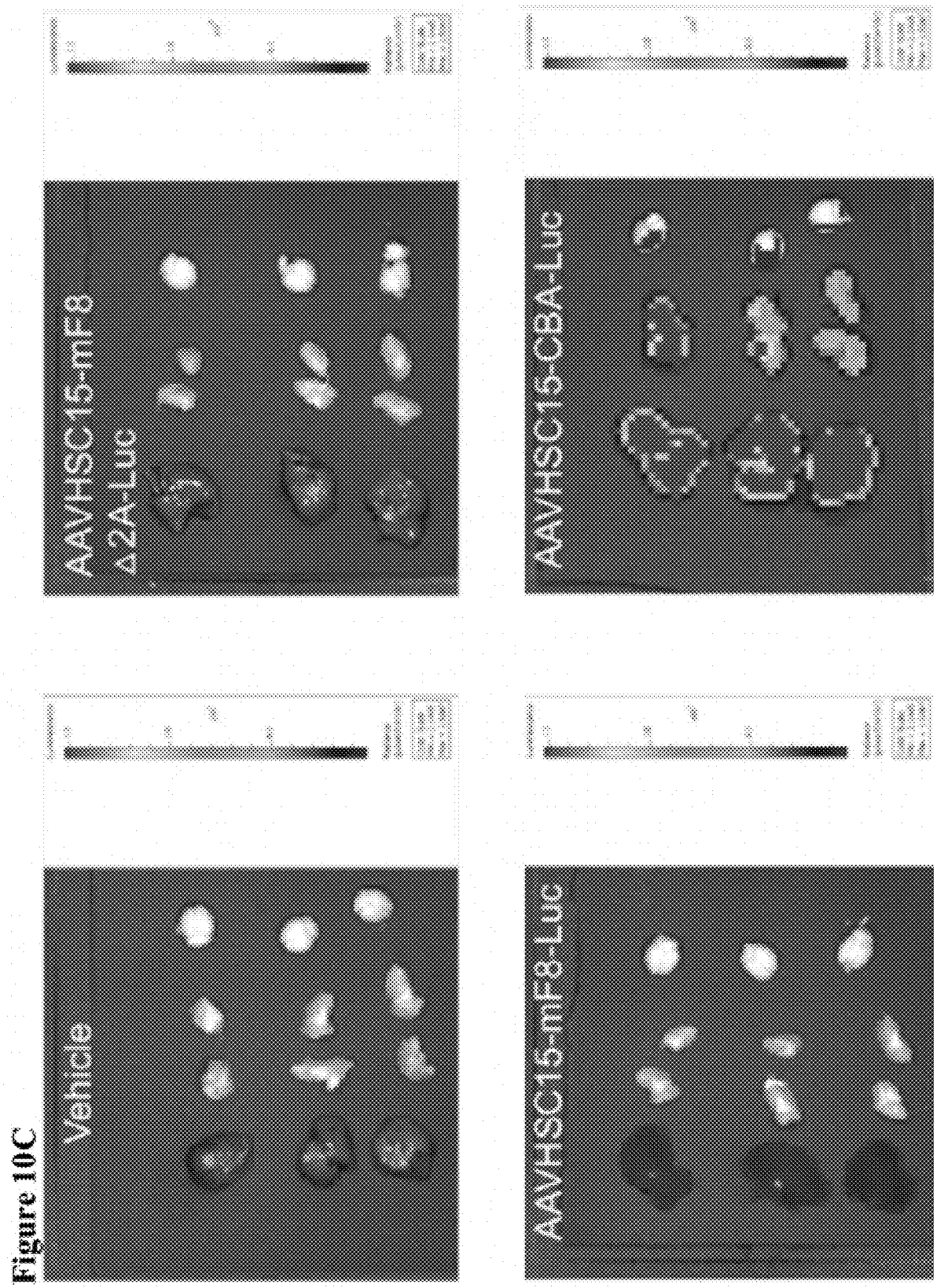

ADENO-ASSOCIATED VIRUS COMPOSITIONS FOR RESTORING F8 GENE FUNCTION AND METHODS OF USE THEREOF

RELATED APPLICATIONS

This application is a continuation of U.S. patent application Ser. No. 16/279,688, filed Feb. 19, 2019, which claims priority to U.S. Provisional Patent Application Ser. No. 62/632,300, filed Feb. 19, 2018, 62/632,919, filed Feb. 20, 2018, and 62/672,385, filed May 16, 2018, the entire disclosures of which are hereby incorporated herein by reference.

STATEMENT OF GOVERNMENT INTEREST

This invention was made with government support under Grant No. P30CA033572 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Feb. 19, 2019, is named 610725_HMT-026_SequenceListing.TXT and is 157,054 bytes in size.

BACKGROUND

Factor VIII (FVIII), also known as anti-hemophilic factor, is a circulating glycoprotein that is important for normal blood clotting. Factor VIII is produced by liver sinusoidal endothelial cells and endothelial cells outside of the liver. This protein circulates in the bloodstream in an inactive form, bound to another molecule called von Willebrand factor (vWF), until an injury that damages blood vessels occurs. In response to injury, FVIII is activated and separates from vWF. The active protein, FVIIIa, interacts with another coagulation factor called factor IX to initiate a cascade of additional chemical reactions that form a blood clot.

Hemophilia A, also called factor VIII deficiency or classic hemophilia, is an inherited or spontaneous genetic disorder caused by missing or defective factor VIII. In the majority of cases it is inherited as an X-linked recessive trait, while nearly one third of cases arise from spontaneous mutations. Clinically, hemophilia A is characterized by internal or external bleeding episodes. Individuals with more severe hemophilia suffer more severe and more frequent bleeding, while others with mild haemophilia typically suffer more minor symptoms except after surgery or serious trauma; individuals with moderate hemophilia have variable symptoms which manifest along a spectrum between severe and mild forms.

F8, the gene for FVIII is located on the long arm of chromosome X, within the Xq28 region. The gene represents 186 kb of the X chromosome. It comprises a 9 kb coding region that contains 26 exons and 25 introns. Mature FVIII is a single-chain polypeptide containing 2332 amino acids. Approximately 40% of cases of severe FVIII deficiency arise from a large inversion involving intron 22 that disrupts the F8 gene. Deletions, insertions, and point mutations account for the remaining 50-60% of the F8 defects that cause hemophilia A.

Currently there is no cure for hemophilia A. For patients with moderate to severe hemophilia A or acute bleeding episodes, treatment typically involves an infusion of recombinant FVIII or FVIII derived from donated human blood. Patients may also be treated prophylactically with regular infusions of FVIII or desmopressin (DDAVP), the latter directly promoting the release of von Willebrand factor (vWF) and indirectly promoting FVIII half-life.

Gene therapy provides a unique opportunity to cure genetic disorders. Retroviral vectors, including lentiviral vectors, are capable of integrating nucleic acids into host cell genomes. However, these vectors may raise safety concerns due to their non-targeted insertion into the genome. For example, there is a risk of the vector disrupting a tumor suppressor gene or activating an oncogene, thereby causing a malignancy. Indeed, in a clinical trial for treating X-linked severe combined immunodeficiency (X-SCID) by transducing $CD34^+$ bone marrow precursors with a gammaretroviral vector, four out of ten patients developed leukemia (Hacein-Bey-Abina et al., *J. Clin. Invest.* (2008) 118(9):3132-42).

Nuclease-based gene editing technologies, such as meganucleases, zinc finger nucleases (ZFNs), transcription activator-like effector nucleases (TALENs), and clustered, regularly interspaced, short palindromic repeat (CRISPR) technology, may be used to correct defects in genes in patients. However, each of these technologies raises safety concerns due to the potential for off-target mutation of sites in the human genome similar in sequence to the intended target site.

Accordingly, there is a need in the art for improved gene therapy compositions and methods that can efficiently and safely restore F8 gene function in hemophilia A patients.

SUMMARY

Provided herein are adeno-associated virus (AAV) compositions that can restore F8 gene function in cells, and methods for using the same to treat diseases associated with reduction of F8 gene function (e.g., hemophilia A). Also provided are packaging systems for making the adeno-associated virus compositions.

The AAV compositions and methods disclosed herein are particularly advantageous in that they allow for highly efficient correction of mutations in an F8 gene in vivo, without the need for cleavage of genomic DNA using an exogenous nuclease (e.g., a meganuclease, a zinc finger nuclease, a transcriptional activator-like nuclease (TALEN), or an RNA-guided nuclease such as a Cas9).

Accordingly, in one aspect the instant disclosure provides a replication-defective adeno-associated virus (AAV) comprising: an AAV capsid; and a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus.

In another aspect, a method for correcting a mutation in an F8 gene in a cell, the method comprising transducing the cell with a replication-defective adeno-associated virus (AAV) comprising: an AAV capsid; and a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus, wherein the cell is transduced without co-transducing or co-administering an exogenous nuclease or a nucleotide sequence that encodes an exogenous nuclease.

In certain embodiments, the cell is a hepatocyte or an endothelial cell. In certain embodiments, the endothelial cell is a hepatic sinusoidal endothelial cell. In certain embodiments, the cell is in a mammalian subject and the AAV is administered to the subject in an amount effective to transduce the cell in the subject.

In another aspect, the instant disclosure provides a method for treating a subject having a disease or disorder associated with an F8 gene mutation, the method comprising administering to the subject an effective amount of a replication-defective AAV comprising: an AAV capsid comprising an AAV Clade F capsid protein; and a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus, wherein an exogenous nuclease or a nucleotide sequence that encodes an exogenous nuclease is not co-administered to the subject.

In certain embodiments, the disease or disorder is hemophilia A. In certain embodiments, the subject is a human subject.

The following embodiments apply to each of the foregoing aspects.

In certain embodiments, the editing element comprises a portion of an F8 coding sequence. In certain embodiments, the portion of the F8 coding sequence encodes an amino acid sequence set forth in SEQ ID NO: 25. In certain embodiments, the portion of the F8 coding sequence comprises or consists of the sequence set forth in SEQ ID NO: 26. In certain embodiments, the portion of the F8 coding sequence is silently altered.

In certain embodiments, the editing element comprises 5' to 3' a portion of an F8 coding sequence and a polyadenylation sequence. In certain embodiments, the portion of the F8 coding sequence consists of the sequence set forth in SEQ ID NO: 26. In certain embodiments, the target locus is the internucleotide bond between nucleotide 126,476 and nucleotide 126,477 of the F8 gene. In certain embodiments, the target locus is a nucleotide sequence adjacently 3' to nucleotide 126,476 of the F8 gene.

In certain embodiments, the editing element comprises 5' to 3' a splice acceptor site, a portion of an F8 coding sequence, and optionally a polyadenylation sequence. In certain embodiments, the nucleotide adjacently 5' to the target locus is in an intron of the F8 gene. In certain embodiments, the portion of the F8 coding sequence consists of the sequence set forth in SEQ ID NO: 26. In certain embodiments, the nucleotide adjacently 5' to the target locus is in intron 22 of the F8 gene.

In certain embodiments, the polyadenylation sequence is an exogenous polyadenylation sequence. In certain embodiments, the exogenous polyadenylation sequence is an SV40 polyadenylation sequence. In certain embodiments, the SV40 polyadenylation sequence has a nucleotide sequence set forth in SEQ ID NO: 23, 35, 36, or 37.

In certain embodiments, the editing element comprises the nucleic acid sequence set forth in SEQ ID NO: 33.

In certain embodiments, the 5' homology arm nucleotide sequence is at least 90%, 95%, 96%, 97%, 98%, or 99% identical to the first genomic region. In certain embodiments, the 3' homology arm nucleotide sequence is at least 90%, 95%, 96%, 97%, 98%, or 99% identical to the second genomic region. In certain embodiments, the first genomic region is located in a first editing window, and the second genomic region is located in a second editing window. In certain embodiments, the first editing window consists of the nucleotide sequence set forth in SEQ ID NO: 31, 32, or 34. In certain embodiments, the second editing window consists of the nucleotide sequence set forth in SEQ ID NO: 31, 32, or 34. In certain embodiments, the first editing window consists of the nucleotide sequence set forth in SEQ ID NO: 31, and the second editing window consists of the nucleotide sequence set forth in SEQ ID NO: 32.

In certain embodiments, the first genomic region consists of the nucleotide sequence set forth in SEQ ID NO: 31. In certain embodiments, the second genomic region consists of the nucleotide sequence set forth in SEQ ID NO: 32.

In certain embodiments, each of the 5' and 3' homology arm nucleotide sequences independently has a length of about 100 to about 4500 nucleotides. In certain embodiments, the correction genome comprises a nucleic acid sequence selected from the group consisting of SEQ ID NOs: 38-41.

In certain embodiments, the correction genome further comprises a 5' inverted terminal repeat (5' ITR) nucleotide sequence 5' to the 5' homology arm nucleotide sequence, and a 3' inverted terminal repeat (3' ITR) nucleotide sequence 3' to the 3' homology arm nucleotide sequence. In certain embodiments, the 5' ITR nucleotide sequence has at least 95% sequence identity to SEQ ID NO: 18, and the 3' ITR nucleotide sequence has at least 95% sequence identity to SEQ ID NO: 19, 61, or 63. In certain embodiments, the 5' ITR nucleotide sequence has at least 95% sequence identity to SEQ ID NO: 20, and the 3' ITR nucleotide sequence has at least 95% sequence identity to SEQ ID NO: 21. In certain embodiments, the 5' ITR nucleotide sequence has at least 95% sequence identity to SEQ ID NO: 46, and the 3' ITR nucleotide sequence has at least 95% sequence identity to SEQ ID NO: 19, 61, or 63.

In certain embodiments, the correction genome comprises a nucleic acid sequence selected from the group consisting of SEQ ID NOs: 42-45. In certain embodiments, the correction genome consists of a nucleic acid sequence selected from the group consisting of SEQ ID NOs: 42-45.

In certain embodiments, the integration efficiency of the editing element into the target locus is at least 2% when the AAV is contacted in vitro in the absence of an exogenous nuclease with a population of B lymphoblastoid cells under standard AAV transduction conditions. In certain embodiments, the allelic frequency of integration of the editing element into the target locus is at least 1% when the AAV is contacted in vitro in the absence of an exogenous nuclease with a population of B lymphoblastoid cells under standard AAV transduction conditions.

In certain embodiments, the AAV capsid comprises an AAV Clade F capsid protein.

In certain embodiments, the AAV Clade F capsid protein comprises an amino acid sequence having at least 95% sequence identity with the amino acid sequence of amino acids 203-736 of SEQ ID NO: 1, 2, 3, 4, 6, 7, 10, 11, 12, 13, 15, 16, or 17. In certain embodiments, the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments,
(a) the amino acid in the capsid protein corresponding to amino acid 626 of SEQ ID NO: 2 is G, and the amino acid in the capsid protein corresponding to amino acid 718 of SEQ ID NO: 2 is G;
(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(c) the amino acid in the capsid protein corresponding to amino acid 505 of SEQ ID NO: 2 is R, and the amino acid in the capsid protein corresponding to amino acid 687 of SEQ ID NO: 2 is R;
(d) the amino acid in the capsid protein corresponding to amino acid 346 of SEQ ID NO: 2 is A, and the amino acid in the capsid protein corresponding to amino acid 505 of SEQ ID NO: 2 is R; or
(e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 203-736 of SEQ ID NO: 1, 2, 3, 4, 6, 7, 10, 11, 12, 13, 15, 16, or 17.

In certain embodiments, the AAV Clade F capsid protein comprises an amino acid sequence having at least 95% sequence identity with the amino acid sequence of amino acids 138-736 of SEQ ID NO: 1, 2, 3, 4, 5, 6, 7, 9, 10, 11, 12, 13, 15, 16, or 17. In certain embodiments, the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments,
(a) the amino acid in the capsid protein corresponding to amino acid 626 of SEQ ID NO: 2 is G, and the amino acid in the capsid protein corresponding to amino acid 718 of SEQ ID NO: 2 is G;
(b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(c) the amino acid in the capsid protein corresponding to amino acid 505 of SEQ ID NO: 2 is R, and the amino acid in the capsid protein corresponding to amino acid 687 of SEQ ID NO: 2 is R;
(d) the amino acid in the capsid protein corresponding to amino acid 346 of SEQ ID NO: 2 is A, and the amino acid in the capsid protein corresponding to amino acid 505 of SEQ ID NO: 2 is R; or
(e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 138-736 of SEQ ID NO: 1, 2, 3, 4, 5, 6, 7, 9, 10, 11, 12, 13, 15, 16, or 17.

In certain embodiments, the AAV Clade F capsid protein comprises an amino acid sequence having at least 95% sequence identity with the amino acid sequence of amino acids 1-736 of SEQ ID NO: 1, 2, 3, 4, 5, 6, 7, 8, 9, 10, 11, 12, 13, 15, 16, or 17. In certain embodiments, the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G.

In certain embodiments,
(a) the amino acid in the capsid protein corresponding to amino acid 2 of SEQ ID NO: 2 is T, and the amino acid in the capsid protein corresponding to amino acid 312 of SEQ ID NO: 2 is Q;
(b) the amino acid in the capsid protein corresponding to amino acid 65 of SEQ ID NO: 2 is I, and the amino acid in the capsid protein corresponding to amino acid 626 of SEQ ID NO: 2 is Y;
(c) the amino acid in the capsid protein corresponding to amino acid 77 of SEQ ID NO: 2 is R, and the amino acid in the capsid protein corresponding to amino acid 690 of SEQ ID NO: 2 is K;
(d) the amino acid in the capsid protein corresponding to amino acid 119 of SEQ ID NO: 2 is L, and the amino acid in the capsid protein corresponding to amino acid 468 of SEQ ID NO: 2 is S;
(e) the amino acid in the capsid protein corresponding to amino acid 626 of SEQ ID NO: 2 is G, and the amino acid in the capsid protein corresponding to amino acid 718 of SEQ ID NO: 2 is G;
(f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M;
(g) the amino acid in the capsid protein corresponding to amino acid 505 of SEQ ID NO: 2 is R, and the amino acid in the capsid protein corresponding to amino acid 687 of SEQ ID NO: 2 is R;
(h) the amino acid in the capsid protein corresponding to amino acid 346 of SEQ ID NO: 2 is A, and the amino acid in the capsid protein corresponding to amino acid 505 of SEQ ID NO: 2 is R; or
(i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C.

In certain embodiments, the capsid protein comprises the amino acid sequence of amino acids 1-736 of SEQ ID NO: 1, 2, 3, 4, 5, 6, 7, 8, 9, 10, 11, 12, 13, 15, 16, or 17.

In another aspect, the instant disclosure provides a pharmaceutical composition comprising an AAV described herein.

In another aspect, the instant disclosure provides a packaging system for recombinant preparation of an AAV, wherein the packaging system comprises: a Rep nucleotide sequence encoding one or more AAV Rep proteins; a Cap nucleotide sequence encoding one or more AAV Clade F capsid proteins described herein; and a correction genome described herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome. In certain embodiments, the Rep nucleotide sequence encodes an AAV2 Rep protein. In certain embodiments, the AAV2 Rep protein is 78/68 or Rep 68/52. In certain embodiments, the AAV2 Rep protein comprises an amino acid sequence having a minimum percent sequence identity to the AAV2 Rep amino acid sequence of SEQ ID NO: 22, wherein the minimum percent sequence identity is at least 70% across the length of the amino acid sequence encoding the AAV2 Rep protein.

In certain embodiments, the packaging system further comprises a third vector, wherein the third vector is a helper virus vector. In certain embodiments, the helper virus vector is an independent third vector. In certain embodiments, the helper virus vector is integral with the first vector. In certain embodiments, the helper virus vector is integral with the second vector. In certain embodiments, the third vector comprises genes encoding helper virus proteins. In certain embodiments, the helper virus is selected from the group consisting of adenovirus, herpes virus, vaccinia virus, and cytomegalovirus (CMV). In certain embodiments, the helper virus is adenovirus. In certain embodiments, the adenovirus genome comprises one or more adenovirus RNA genes selected from the group consisting of E1, E2, E4 and VA. In certain embodiments, the helper virus is herpes simplex virus (HSV). In certain embodiments, the HSV genome comprises one or more of HSV genes selected from the group consisting of UL5/8/52, ICPO, ICP4, ICP22 and UL30/UL42.

In certain embodiments, the first vector and the third vector are contained within a first transfecting plasmid. In certain embodiments, the nucleotides of the second vector and the third vector are contained within a second transfecting plasmid. In certain embodiments, the nucleotides of the first vector and the third vector are cloned into a recombinant helper virus. In certain embodiments, the nucleotides of the second vector and the third vector are cloned into a recombinant helper virus.

In another aspect, the instant disclosure provides a method for recombinant preparation of an AAV, the method comprising introducing the packaging system described herein into a cell under conditions operative for enclosing the correction genome in the capsid to form the AAV.

BRIEF DESCRIPTION OF THE DRAWINGS

FIG. 7D is a set of photographs showing bioluminescence images of the liver, kidney, muscle, and brain tissues (from left to right in each photograph) of mice at various time points post administration of the VG-mF8-001-Luc vector packaged in AAVHSC15 capsid (AAVHSC15-mF8-Luc). The various time points increase from left to right in the top row and continue from left to right in the bottom row of photographs.

FIG. 10C is a set of photographs showing, from top to bottom, the liver, brain, and kidney obtained from mice administered the indicated vectors.

DETAILED DESCRIPTION

Figure 1A:
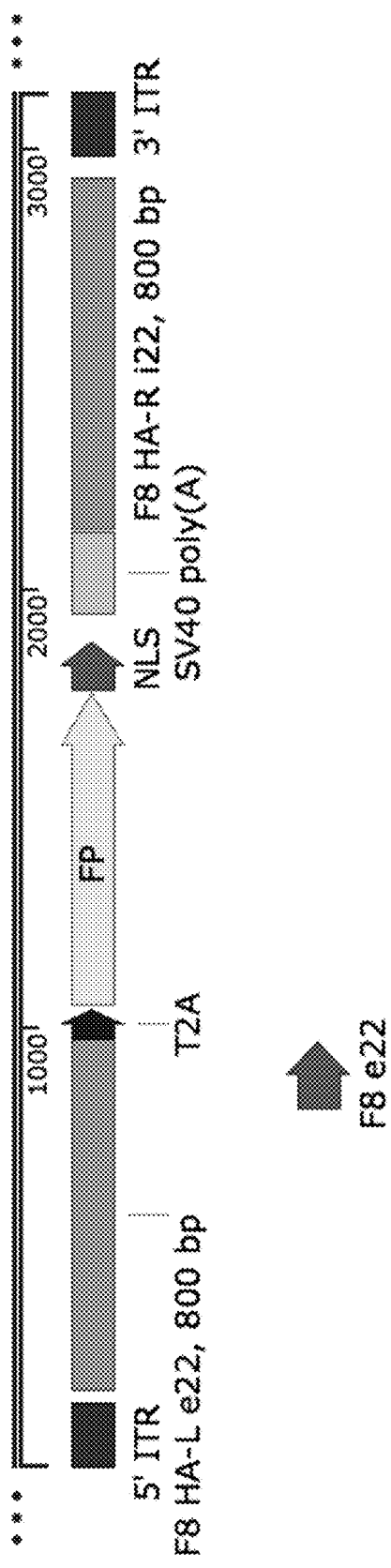
FIGS. 1A and 1B are maps of the VG-F8-002-FP and VG-F8-003-FP vectors, respectivley.

The instant disclosure provided adeno-associated virus (AAV) compositions that can restore F8 gene function in a cell. Also provide are packaging systems for making the adeno-associated virus compositions.

I. Definitions

As used herein, the term "replication-defective adeno-associated virus" refers to an AAV comprising a genome lacking Rep and Cap genes.

As used herein, the term "F8 gene" refers to a wild-type or mutant gene encoding the FVIII protein, including but not limited to the coding regions, exons, introns, 5' UTR, 3' UTR, and transcriptional regulatory regions of the F8 gene. The human F8 gene is identified by Entrez Gene ID 2157. Wild-type human F8 gene is identified by nucleotides 5,001 to 191,936 of NCBI Reference Sequence: NG_011403.1. An exemplary nucleotide sequence of a full-length human F8 cDNA is identified by NCBI Reference No.: NM_000132.3. An exemplary amino acid sequence of a full-length human FVIII polypeptide, including its 19-amino acid signal peptide, is identified by NCBI Reference No.: NP_000123.1. Intron 22 of human F8 corresponds to nucleotides 131,648-164,496 (32,849 nt) of NCBI Reference Sequence: NG_011403.1.

As used herein, the term "correcting a mutation in an F8 gene" refers to the insertion, deletion, or substitution of one or more nucleotides at a target locus in a mutant F8 gene to create an F8 gene that is capable of expressing a wild-type FVIII polypeptide or a functional equivalent thereof. In certain embodiments, "correcting a mutation in an F8 gene" involves inserting a nucleotide sequence encoding at least a portion of a wild-type FVIII polypeptide or a functional equivalent thereof into the mutant F8 gene, such that a wild-type FVIII polypeptide or a functional equivalent thereof is expressed from the mutant F8 gene locus (e.g., under the control of an endogenous F8 gene promoter). A skilled person in the art will appreciate that the portion of a correction genome comprising the 5' homology arm, editing element, and 3' homology arm can be in the sense or antisense orientation relative to the target locus (e.g., the human F8 gene).

As used herein, the term "correction genome" refers to a recombinant AAV genome that is capable of integrating an editing element (e.g., one or more nucleotides or an internucleotide bond) via homologous recombination into a target locus to correct a genetic defect in an F8 gene. In certain embodiments, the target locus is in the human F8 gene. The skilled artisan will appreciate that the portion of a correction genome comprising the 5' homology arm, editing element, and 3' homology arm can be in the sense or antisense orientation relative to the target locus (e.g., the human F8 gene).

As used herein, the term "editing element" refers to the portion of a correction genome that when integrated at a target locus modifies the target locus. An editing element can mediate insertion, deletion, or substitution of one or more nucleotides at the target locus.

As used herein, the term "target locus" refers to a region of a chromosome or an internucleotide bond (e.g., a region or an internucleotide bond of the human F8 gene) that is modified by an editing element.

As used herein, the term "homology arm" refers to a portion of a correction genome positioned 5' or 3' to an editing element that is substantially identical to the genome flanking a target locus. In certain embodiments, the target locus is in a human F8 gene, and the homology arm comprises a sequence substantially identical to the genome flanking the target locus.

As used herein, the term "Clade F capsid protein" refers to an AAV VP1, VP2, or VP3 capsid protein that has at least 90% identity with the VP1, VP2, or VP3 amino acid sequences set forth, respectively, in amino acids 1-736, 138-736, and 203-736 of SEQ ID NO: 1 herein. As used herein, the identity between two nucleotide sequences or between two amino acid sequences is determined by the number of identical nucleotides or amino acids in alignment divided by the full length of the longer nucleotide or amino acid sequence.

As used herein, the term "a disease or disorder associated with an F8 gene mutation" refers to any disease or disorder caused by, exacerbated by, or genetically linked with mutation of an F8 gene. In certain embodiments, the disease or disorder associated with an F8 gene mutation is hemophilia A.

As used herein, the term "coding sequence" refers to the portion of a complementary DNA (cDNA) that encodes a polypeptide, starting at the start codon and ending at the stop codon. A gene may have one or more coding sequences due to alternative splicing and/or alternative translation initiation. A coding sequence may either be wild-type or silently altered. An exemplary full-length wild-type F8 coding sequence is identified by nucleotides 172 to 7,227 of NCBI Reference No.: NM_000132.3. An exemplary portion of wild-type F8 coding sequence, corresponding to exons 22-26, is set forth in SEQ ID NO: 26.

As used herein, the term "silently altered" or "silent alteration" refers to alteration of a coding sequence of a gene (e.g., by nucleotide substitution) without changing the amino acid sequence of the polypeptide encoded by the gene. In certain embodiments, silent alteration increases the expression level of a coding sequence. In certain embodiments, silent alteration reduces off-targeting to undesired genomic loci.

As used herein, the term "polyadenylation sequence" refers to a DNA sequence that when transcribed into RNA constitutes a polyadenylation signal sequence. The polyadenylation sequence can be native (e.g., from the F8 gene) or exogenous. The exogenous polyadenylation sequence can be a mammalian or a viral polyadenylation sequence (e.g., an SV40 polyadenylation sequence).

In the instant disclosure, nucleotide positions in an F8 gene are specified relative to the first nucleotide of the start codon. The first nucleotide of a start codon is position 1; the nucleotides 5' to the first nucleotide of the start codon have negative numbers; the nucleotides 3' to the first nucleotide of the start codon have positive numbers. A skilled person will appreciate that a gene may have multiple start codons due to alternative splicing and/or alternative translation initiation. As used herein, nucleotide 1 of the human F8 gene is nucleotide 5172 of the NCBI Reference Sequence: NG_011403.1. The nucleotide adjacently 5' to the start codon is nucleotide −1. Thus, nucleotide −1 of the human F8 gene is nucleotide 5173 of the NCBI Reference Sequence: NG_011403.1. As used herein, nucleotide 1 of the mouse F8 gene is nucleotide 75,383,525 of the NCBI Reference Sequence: NC_000086.7 on the negative strand.

In the instant disclosure, exons and introns in an F8 gene are specified relative to the exon encompassing the first nucleotide of the start codon, which is nucleotide 5,172 of the NCBI Reference Sequence: NG_011403.1. The exon encompassing the first nucleotide of the start codon is exon 1. Exons 3' to exon 1 are from 5' to 3': exon 2, exon 3, etc. Introns 3' to exon 1 are from 5' to 3': intron 1, intron 2, etc. Accordingly, the F8 gene comprises from 5' to 3': exon 1, intron 1, exon 2, intron 2, exon 3, etc. A skilled person will appreciate that a gene may be transcribed into multiple different mRNAs. As such, a gene (e.g., F8) may have multiple different sets of exons and introns. As used herein, exon 1 of the human F8 gene is nucleotides 5,001-5,314 of the NCBI Reference Sequence: NG_011403.1. An exemplary intron 1 of the human F8 gene is nucleotides 5,315-28,123 of the NCBI Reference Sequence: NG_011403.1. An exemplary exon 22 of the human F8 gene is nucleotides 131,492-131,647 (156 nt) of the NCBI Reference Sequence: NG_011403.1. An exemplary intron 22 of the human F8 gene is nucleotides 131,648-164,496 (32,849 nt) of the NCBI Reference Sequence: NG_011403.1. An exemplary exon 23 of the human F8 gene is nucleotides 164,497-164,641 (145 nt) of the NCBI Reference Sequence: NG_011403.1. An exemplary intron 23 of the human F8 gene is nucleotides 164,642-165,857 (1216 nt) of the NCBI Reference Sequence: NG_011403.1. An exemplary exon 24 of the human F8 gene is nucleotides 165,858-166,006 (149 nt) of the NCBI Reference Sequence: NG_011403.1. An exemplary intron 24 of the human F8 gene is nucleotides 166,007-167,115 (1109 nt) of the NCBI Reference Sequence: NG_011403.1. An exemplary exon 25 of the human F8 gene is nucleotides 167,116-167,292 (177 nt) of the NCBI Reference Sequence: NG_011403.1. An exemplary intron 25 of the human F8 gene is nucleotides 167, 293-189,971 (22,679 nt) of the NCBI Reference Sequence: NG_011403.1. An exemplary exon 26 of the human F8 gene is nucleotides 189,972-191,936 (1965 nt) of the NCBI Reference Sequence: NG_011403.1.

As used herein, the term "integration" refers to introduction of an editing element into a target locus of a target gene by homologous recombination between a correction genome and the target gene. Integration of an editing element can result in substitution, insertion and/or deletion of one or more nucleotides in a target gene. For example, in certain embodiments, the term "integration" refers to introduction of an editing element into a target locus of an F8 gene by homologous recombination between a correction genome and the F8 gene. Integration of an editing element can result in substitution, insertion and/or deletion of one or more nucleotides in an F8 gene.

As used herein, the term "integration efficiency of the editing element into the target locus" refers to the percentage of cells in a transduced population in which integration of the editing element into the target locus has occurred.

As used herein, the term "allelic frequency of integration of the editing element into the target locus" refers to the percentage of alleles in a population of transduced cells in which integration of the editing element into the target locus has occurred.

As used herein, the term "standard AAV transduction conditions" refers to transduction of B lymphoblastoid cells with an AAV at a multiplicity of infection (MOI) of $1.5 \times 10^5$, wherein the cells are cultured in RPMI-1640 media supplemented with 15% fetal calf serum (FCS), and 2 mmol/L L-glutamine at 37° C. in an incubator environment of 5% carbon dioxide ($CO_2$), wherein the cells in log phase growth are seeded at approximately 200,000 cells per ml and infected on the same day, wherein the AAV is formulated in phosphate buffered saline (PBS), and wherein the AAV is added to the cell culture medium containing the B lymphoblastoid cells in a volume that is less than or equal to 5% of the volume of the culture medium.

As used herein, "exogenous polyadenylation sequence" refers to a polyadenylation sequence not identical or substantially identical to the endogenous polyadenylation sequence of a gene (e.g., human gene). For example, in certain embodiments, "exogenous polyadenylation sequence" refers to a polyadenylation sequence not identical or substantially identical to the endogenous polyadenylation sequence of an F8 gene (e.g., human F8 gene). In certain embodiments, an exogenous polyadenylation sequence is a polyadenylation sequence of a non-F8 gene in the same species (e.g., human). In certain embodiments, an exogenous polyadenylation sequence is a polyadenylation sequence of a different species (e.g., a virus).

As used herein, the term "effective amount" in the context of the administration of an AAV to a subject refers to the amount of the AAV that achieves a desired prophylactic or therapeutic effect.

II. Adeno-Associated Virus Compositions

In one aspect, provided herein are novel replication-defective AAV compositions useful for restoring F8 expression in cells with reduced or otherwise defective F8 gene function. Such AAV compositions are highly efficient at correcting mutations in the F8 gene or restoring F8 expression, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the AAV composition disclosed herein does not comprise an exogenous nuclease or a nucleotide sequence that encodes an exogenous nuclease.

In certain embodiments, the AAV disclosed herein comprise: an AAV capsid comprising an AAV capsid protein; and a correction genome for editing a target locus in an F8 gene.

The AAV capsid proteins that can be used in the AAV compositions disclosed herein include without limitation AAV capsid proteins and derivatives thereof of Clade A AAVs, Clade B AAVs, Clade C AAVs, Clade D AAVs, Clade E AAVs, and Clade F AAVs. In certain embodiments, the AAV capsid protein is an AAV capsid protein or a derivative thereof of AAV1, AAV2, AAV3, AAV4, AAV5, AAV6, AAV7, AAV8, AAV9, or AAVrh10.

In certain embodiments, the AAV capsid protein is a Clade F AAV capsid protein. Any AAV Clade F capsid protein or derivative thereof can be used in the AAV compositions disclosed herein. For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 203-736 of SEQ ID NO: 1, 2, 3, 4, 5, 6, 7, 8, 9, 10, 11, 12, 13, 15, 16, or 17, wherein: the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 203-736 of SEQ ID NO: 1, 2, 3, 4, 6, 7, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 138-736 of SEQ ID NO: 1, 2, 3, 4, 5, 6, 7, 8, 9, 10, 11, 12, 13, 15, 16, or 17, wherein: the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 138-736 of SEQ ID NO: 1, 2, 3, 4, 5, 6, 7, 9, 10, 11, 12, 13, 15, 16, or 17.

For example, in certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17. In certain embodiments, the AAV Clade F capsid protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the amino acid sequence of amino acids 1-736 of SEQ ID NO: 1, 2, 3, 4, 5, 6, 7, 8, 9, 10, 11, 12, 13, 15, 16, or 17, wherein: the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G. In certain embodiments, the amino acid in the capsid protein corresponding to amino acid 2 of SEQ ID NO: 2 is T, and the amino acid in the capsid protein corresponding to amino acid 312 of SEQ ID NO: 2 is Q. In certain embodiments, the amino acid in the capsid protein corresponding to amino acid 65 of SEQ ID NO: 2 is I, and the amino acid in the capsid protein corresponding to amino acid 626 of SEQ ID NO: 2 is Y. In certain embodiments, the amino acid in the capsid protein corresponding to amino acid 77 of SEQ ID NO: 2 is R, and the amino acid in the capsid protein corresponding to amino acid 690 of SEQ ID NO: 2 is K. In certain embodiments, the amino acid in the capsid protein corresponding to amino acid 119 of SEQ ID NO: 2 is L, and the amino acid in the capsid protein corresponding to amino acid 468 of SEQ ID NO: 2 is S. In certain embodiments, the amino acid in the capsid protein corresponding to amino acid 626 of SEQ ID NO: 2 is G, and the amino acid in the capsid protein corresponding to amino acid 718 of SEQ ID NO: 2 is G. In certain embodiments, the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M. In certain embodiments, the amino acid in the capsid protein corresponding to amino acid 505 of SEQ ID NO: 2 is R, and the amino acid in the capsid protein corresponding to amino acid 687 of SEQ ID NO: 2 is R. In certain embodiments, the amino acid in the capsid protein corresponding to amino acid 346 of SEQ ID NO: 2 is A, and the amino acid in the capsid protein corresponding to amino acid 505 of SEQ ID NO: 2 is R. In certain embodiments, the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C. In certain embodiments, the AAV Clade F capsid protein comprises the amino acid sequence of amino acids 1-736 of SEQ ID NO: 1, 2, 3, 4, 5, 6, 7, 8, 9, 10, 11, 12, 13, 15, 16, or 17.

In certain embodiments, the AAV capsid comprises two or more of: a) a Clade F capsid protein comprising the amino acid sequence of amino acids 203-736 of SEQ ID NO: 1, 2, 3, 4, 5, 6, 7, 8, 9, 10, 11, 12, 13, 14, 15, 16, or 17; b) a Clade F capsid protein comprising the amino acid sequence of amino acids 138-736 of SEQ ID NO: 1, 2, 3, 4, 5, 6, 7, 8, 9, 10, 11, 12, 13, 14, 15, 16, or 17; and c) a Clade F capsid protein comprising the amino acid sequence of amino acids 1-736 of SEQ ID NO: 1, 2, 3, 4, 5, 6, 7, 8, 9, 10, 11, 12, 13, 14, 15, 16, or 17. In certain embodiments, the AAV capsid comprises: a) a Clade F capsid protein having an amino acid sequence consisting of amino acids 203-736 of SEQ ID NO: 1, 2, 3, 4, 5, 6, 7, 8, 9, 10, 11, 12, 13, 14, 15, 16, or 17; b) a Clade F capsid protein having an amino acid sequence consisting of amino acids 138-736 of SEQ ID NO: 1, 2, 3, 4, 5, 6, 7, 8, 9, 10, 11, 12, 13, 14, 15, 16, or 17; and c) a Clade F capsid protein having an amino acid sequence consisting of amino acids 1-736 of SEQ ID NO: 1, 2, 3, 4, 5, 6, 7, 8, 9, 10, 11, 12, 13, 14, 15, 16, or 17.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 8; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 8; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 8. In certain embodiments, the AAV capsid comprises one or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises two or more of: (a) a Clade F capsid protein comprising the amino acid sequence of amino acids 203-736 of SEQ ID NO: 8; (b) a Clade F capsid protein comprising the amino acid sequence of amino acids 138-736 of SEQ ID NO: 8; and (c) a Clade F capsid protein comprising the amino acid sequence of amino acids 1-736 of SEQ ID NO: 8. In certain embodiments, the AAV capsid comprises: (a) a Clade F capsid protein having an amino acid sequence consisting of amino acids 203-736 of SEQ ID NO: 8; (b) a Clade F capsid protein having an amino acid sequence consisting of amino acids 138-736 of SEQ ID NO: 8; and (c) a Clade F capsid protein having an amino acid sequence consisting of amino acids 1-736 of SEQ ID NO: 8.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 11; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 11; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 11. In certain embodiments, the AAV capsid comprises one or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises two or more of: (a) a Clade F capsid protein comprising the amino acid sequence of amino acids 203-736 of SEQ ID NO: 11; (b) a Clade F capsid protein comprising the amino acid sequence of amino acids 138-736 of SEQ ID NO: 11; and (c) a Clade F capsid protein comprising the amino acid sequence of amino acids 1-736 of SEQ ID NO: 11. In certain embodiments, the AAV capsid comprises: (a) a Clade F capsid protein having an amino acid sequence consisting of amino acids 203-736 of SEQ ID NO: 11; (b) a Clade F capsid protein having an amino acid sequence consisting of amino acids 138-736 of SEQ ID NO: 11; and (c) a Clade F capsid protein having an amino acid sequence consisting of amino acids 1-736 of SEQ ID NO: 11.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 13; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 13; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 13. In certain embodiments, the AAV capsid comprises one or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises two or more of: (a) a Clade F capsid protein comprising the amino acid sequence of amino acids 203-736 of SEQ ID NO: 13; (b) a Clade F capsid protein comprising the amino acid sequence of amino acids 138-736 of SEQ ID NO: 13; and (c) a Clade F capsid protein comprising the amino acid sequence of amino acids 1-736 of SEQ ID NO: 13. In certain embodiments, the AAV capsid comprises: (a) a Clade F capsid protein having an amino acid sequence consisting of amino acids 203-736 of SEQ ID NO: 13; (b) a Clade F capsid protein having an amino acid sequence consisting of amino acids 138-736 of SEQ ID NO: 13; and (c) a Clade F capsid protein having an amino acid sequence consisting of amino acids 1-736 of SEQ ID NO: 13.

In certain embodiments, the AAV capsid comprises one or more of: (a) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 203-736 of SEQ ID NO: 16; (b) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 138-736 of SEQ ID NO: 16; and (c) a Clade F capsid protein comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% sequence identity with the sequence of amino acids 1-736 of SEQ ID NO: 16. In certain embodiments, the AAV capsid comprises one or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises two or more of: (a) a Clade F capsid protein comprising the amino acid sequence of amino acids 203-736 of SEQ ID NO: 16; (b) a Clade F capsid protein comprising the amino acid sequence of amino acids 138-736 of SEQ ID NO: 16; and (c) a Clade F capsid protein comprising the amino acid sequence of amino acids 1-736 of SEQ ID NO: 16. In certain embodiments, the AAV capsid comprises: (a) a Clade F capsid protein having an amino acid sequence consisting of amino acids 203-736 of SEQ ID NO: 16; (b) a Clade F capsid protein having an amino acid sequence consisting of amino acids 138-736 of SEQ ID NO: 16; and (c) a Clade F capsid protein having an amino acid sequence consisting of amino acids 1-736 of SEQ ID NO: 16.

Correction genomes useful in the AAV compositions disclosed herein generally comprise: (i) an editing element for editing a target locus in an F8 gene, (ii) a 5' homology arm nucleotide sequence 5' to the editing element having homology to a first genomic region 5' to the target locus, and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus. In certain embodiments, the correction genome further comprises a 5' inverted terminal repeat (5' ITR) nucleotide sequence 5' to the 5' homology arm nucleotide sequence, and a 3' inverted terminal repeat (3' ITR) nucleotide sequence 3' to the 3' homology arm nucleotide sequence.

Editing elements used in the correction genomes disclosed herein can mediate insertion, deletion, or substitution of one or more nucleotides at the target locus.

In certain embodiments, when correctly integrated by homologous recombination at the target locus, the editing element corrects a mutation in an F8 gene back to the wild-type F8 sequence or a functional equivalent thereof. In certain embodiments, the editing element comprises a portion of an F8 coding sequence (e.g., a portion of a wild-type FVIII coding sequence or a portion of a silently altered F8 coding sequence).

In certain embodiments, the editing element comprises a wild-type or silently altered sequence of exons 23-26 of an F8 gene (e.g., the human F8 gene). In certain embodiments, the editing element comprises at least a portion of an F8 coding sequence. For example, in certain embodiments, the editing element comprises a portion of an F8 coding sequence, and may optionally further comprise an exogenous polyadenylation sequence 3' to the coding sequence. In certain embodiments, the portion of the F8 coding sequence comprises the sequences of exons 23-26 of an F8 gene, optionally further comprising the sequences of one or more of exons 15-22 in the same order as in a genome (e.g., human genome). In certain embodiments, the portion of the F8 coding sequence comprises the sequences of exons 15-26, 16-26, 17-26, 18-26, 19-26, 20-26, 21-26, or 22-26 of an F8 gene. In certain embodiments, the portion of the F8 coding sequence comprises the sequences of exons 22-26 (SEQ ID NO: 26). In certain embodiments, the editing element comprises the sequence set forth in SEQ ID NO: 33.

In certain embodiments, the target locus is an internucleotide bond or a nucleotide sequence adjacently 3' to the last nucleotide of any one of exons 15-22. In certain embodiments, integration of the editing element in a genome (e.g., human genome) results in generation of a sequence comprising exons 1 to X and introns 1 to X−1 (X minus 1) of an F8 gene (e.g., the human F8 gene), and a portion of an F8 coding sequence (e.g., a human F8 coding sequence) comprising the sequences of exons X+1 (X plus 1) to 26 or a silently altered variant thereof, wherein X is any number selected from 14, 15, 16, 17, 18, 19, 20, 21, and 22, and wherein the exons and introns in the editing element are positioned in the same order as in the genome. In certain embodiments, X is 22.

In certain embodiments, the portion of the F8 coding sequence encodes an amino acid sequence comprising or consisting of the sequence set forth in SEQ ID NO: 25. In certain embodiments, the nucleic acid sequence encoding SEQ ID NO: 25 is wild-type (e.g., having the sequence set forth in SEQ ID NO: 26). In certain embodiments, the nucleic acid sequence encoding SEQ ID NO: 25 is silently altered. In certain embodiments, the target locus is an internucleotide bond or a nucleotide sequence adjacently 3' to the last nucleotide of exon 22 of an F8 gene (e.g., the internucleotide bond between nucleotides 126,476 and 126,477 of the human F8 gene, or a sequence starting at nucleotide 126,477 of the human F8 gene), wherein integration of the editing element results in generation of a sequence comprising 5' to 3': exon 1, intron 1, exon 2, intron 2, exon 3, intron 3, exon 4, intron 4, exon 5, intron 5, exon 6, intron 6, exon 7, intron 7, exon 8, intron 8, exon 9, intron 9, exon 10, intron 10, exon 11, intron 11, exon 12, intron 12, exon 13, intron 13, exon 14, intron 14, exon 15, intron 15, exon 16, intron 16, exon 17, intron 17, exon 18, intron 18, exon 19, intron 19, exon 20, intron 20, exon 21, intron 21, exon 22, exon 23, exon 24, exon 25, and exon 26 of an F8 gene at the F8 gene locus, wherein the sequence of each of exon 23, exon 24, exon 25, and exon 26 may be independently wild-type or silently altered.

In certain embodiments, the editing element comprises a portion of an F8 coding sequence (e.g., a portion of a wild-type F8 coding sequence, or a portion of a silently altered F8 coding sequence). Such editing elements can further comprise a splice acceptor site and/or an exogenous polyadenylation sequence. In certain embodiments, the editing element comprises 5' to 3': a splice acceptor site; a portion of an F8 coding sequence (e.g., a portion of a wild-type F8 coding sequence, or a portion of a silently altered F8 coding sequence); and an exogenous polyadenylation sequence. In certain embodiments, the portion of the F8 coding sequence comprises the sequences of exons 23-26 of an F8 gene, optionally further comprising the sequences of one or more of exons 15-22 in the same order as in a genome (e.g., human genome). In certain embodiments, the portion of the F8 coding sequence comprises the sequences of exons 15-26, 16-26, 17-26, 18-26, 19-26, 20-26, 21-26, or 22-26 of an F8 gene.

In certain embodiments, the aforementioned editing element can be integrated into an intron of the F8 gene (e.g., the nucleotide 5' to the target locus is in an intron of the F8 gene, or the 5'-most nucleotide of the target locus is in an intron of the F8 gene) by homologous recombination to produce a recombinant sequence comprising 5' to 3': a portion of the F8 gene 5' to the target locus including the endogenous splice donor site but not the endogenous splice acceptor site of the intron; a splice acceptor site; a portion of an F8 coding sequence (e.g., a portion of a wild-type F8 coding sequence, or a portion of a silently altered F8 coding sequence); and an exogenous polyadenylation sequence. Expression of this recombinant sequence produces a polypeptide comprising the amino acid sequence encoded by the portion of the F8 gene 5' to the target locus fused to a polypeptide comprising the partial amino acid sequence of the FVIII polypeptide encoded by the portion of F8 coding sequence.

In certain embodiments, the nucleotide adjacently 5' to the target locus is in an intron of the F8 gene. In certain embodiments, the target locus is an internucleotide bond in any one of introns 15-22. In certain embodiments, the target locus is a nucleotide sequence adjacently 3' to a nucleotide in any one of introns 15-22. In certain embodiments, integration of the editing element in a genome (e.g., human genome) results in generation of a sequence comprising exons 1 to X, introns 1 to X−1 (X minus 1) and a portion of intron X, a splice acceptor, and a portion of an F8 coding sequence (e.g., a human F8 coding sequence) comprising the sequences of exons X+1 (X plus 1) to 26 or a silently altered variant thereof, wherein X is any number selected from 14, 15, 16, 17, 18, 19, 20, 21, and 22, wherein the exons and introns in the editing element are positioned in the same order as in the genome, and wherein the splice acceptor is between the portion of intron X and the portion of F8 coding sequence. In certain embodiments, X is 22.

In certain embodiments, the nucleotide adjacently 5' to the target locus is in intron 22 of the F8 gene. In certain embodiments, the target locus is an internucleotide bond in intron 22 of the F8 gene. In certain embodiments, the target locus is a sequence in the F8 gene wherein the nucleotide adjacently 5' to this sequence is in intron 22 of the F8 gene, wherein the 3' end of this sequence can be any downstream nucleotide in the F8 gene.

In certain embodiments, one or more portions of an F8 coding sequence within an editing element can be silently altered to be non-identical to the corresponding sequences of the wild-type F8 gene. Silent alteration can be conducted by any method known in the art (e.g., as described in Mauro & Chappell (2014) *Trends Mol Med.* 20(11):604-13, which is incorporated by reference herein in its entirety). An exemplary partial silently altered F8 coding sequence is set forth in SEQ ID NO: 33.

Accordingly, in certain embodiments, the editing element comprises an F8 coding sequence that has been silently altered to be less than 100% (e.g., less than 95%, 90%, 85%, 80%, 75%, 70%, 65%, 60%, 55%, or 50%) identical to the corresponding exons of the wild-type F8 gene. In certain embodiments, the editing element comprises a nucleotide sequence that has been silently altered to be less than 100% (e.g., less than 95%, 90%, 85%, 80%, 75%, 70%, 65%, 60%, 55%, or 50%) identical to the sequence set forth in SEQ ID NO: 26. Such editing elements can further comprise an exogenous polyadenylation sequence 3' to the F8 gene coding sequence.

In certain embodiments, the editing element further comprises a polyadenylation sequence 3' to the portion of F8 coding sequence. In certain embodiments, the polyadenylation sequence is an exogenous polyadenylation sequence. In certain embodiments, the exogenous polyadenylation sequence is an SV40 polyadenylation sequence. In certain embodiments, the SV40 polyadenylation sequence has a nucleotide sequence set forth in SEQ ID NO: 23, 35, 36, or 37.

Any and all of the editing elements disclosed herein can further include a restriction endonuclease site not present in the wild-type F8 gene. Such restriction endonuclease sites allow for identification of cells that have integration of the editing element at the target locus based upon restriction fragment length polymorphism analysis or by nucleic sequencing analysis of the target locus and its flanking regions, or a nucleic acid amplified therefrom.

Any and all of the editing elements disclosed herein can comprise one or more nucleotide alterations that cause one or more amino acid mutations in FVIII polypeptide when integrated into the target locus. In certain embodiments, the mutant FVIII polypeptide is a functional equivalent of the wild-type FVIII polypeptide, i.e., can function as a wild-type FVIII polypeptide. In certain embodiments, the functionally equivalent FVIII polypeptide further comprises at least one characteristic not found in the wild-type FVIII polypeptide, e.g., the ability to resist protein degradation.

In certain embodiments, an editing element as described herein comprises at least 0, 1, 2, 10, 100, 200, 500, 1000, 1500, 2000, 3000, 4000, or 5000 nucleotides. In certain embodiments, the editing element comprises or consists of 1 to 5000, 1 to 4500, 1 to 4000, 1 to 3000, 1 to 2000, 1 to 1000, 1 to 500, 1 to 200, 1 to 100, 1 to 50, or 1 to 10 nucleotides.

In certain embodiments, an editing element as described herein comprises or consists of a partial F8 coding sequence (e.g., exons 22-26 of human F8 coding sequence, or nucleotides 4 to 783 of SEQ ID NO: 31), a 5' untranslated region (UTR), a 3' UTR, a promoter, a splice donor, a splice acceptor, a sequence encoding a non-coding RNA, an insulator, a gene, or a combination thereof.

In certain embodiments, the editing element comprises a nucleic acid sequence at least 70%, 75%, 80%, 85%, 90%, 91%, 92%, 93%, 94%, 95%, 96%, 97%, 98%, 99%, or 99.5% identical to the sequence set forth in SEQ ID NO: 33. In certain embodiments, the editing element comprises the nucleic acid sequence set forth in SEQ ID NO: 33.

Homology arms used in the correction genomes disclosed herein can be directed to any region of the F8 gene or a gene nearby on the genome. The precise identity and positioning of the homology arms are determined by the identity of the editing element and/or the target locus.

Homology arms employed in the correction genomes disclosed herein are substantially identical to the genome flanking a target locus (e.g., a target locus in the F8 gene). In certain embodiments, the 5' homology arm has at least about 90% (e.g., at least about 95%, 96%, 97%, 98%, 99%, or 99.5%) nucleotide sequence identity to a first region 5' to the target locus. In certain embodiments, the 5' homology arm has 100% nucleotide sequence identity to the first region. In certain embodiments, the 3' homology arm has at least about 90% (e.g., at least about 95%, 96%, 97%, 98%, 99%, or 99.5%) nucleotide sequence identity to a second region 3' to the target locus. In certain embodiments, the 3' homology arm has 100% nucleotide sequence identity to the second region. In certain embodiments, the 5' and 3' homology arms are each at least about 90% (e.g., at least about 95%, 96%, 97%, 98%, 99%, or 99.5%) identical to the first and second regions flanking the target locus (e.g., a target locus in the F8 gene), respectively. In certain embodiments, the 5' and 3' homology arms are each 100% identical to the first and second regions flanking the target locus (e.g., a target locus in the F8 gene), respectively. In certain embodiments, differences in nucleotide sequences of the 5' homology arm and/or the 3' homology arm and the corresponding regions the genome flanking a target locus comprise, consist essentially of, or consist of non-coding differences in nucleotide sequences.

The skilled worker will appreciate that homology arms do not need to be 100% identical to the genomic sequence flanking the target locus to be able to mediate integration of an editing element into that target locus by homologous recombination. For example, the homology arms can comprise one or more genetic variations in the human population, and/or one or more modifications (e.g., nucleotide substitutions, insertions, or deletions) designed to improve expression level or specificity. Human genetic variations include both inherited variations and de novo variations that are private to the target genome, and encompass simple nucleotide polymorphisms, insertions, deletions, rearrangements, inversions, duplications, micro-repeats, and combinations thereof. Such variations are known in the art, and can be found, for example, in the databases of dnSNP (see Sherry et al. Nucleic Acids Res. 2001; 29(1):308-11), the Database of Genomic Variants (see Nucleic Acids Res. 2014; 42(Database issue):D986-92), ClinVar (see Nucleic Acids Res. 2014; 42(Database issue): D980-D985), Genbank (see Nucleic Acids Res. 2016; 44(Database issue): D67-D72), ENCODE (genome.ucsc.edu/encode/terms.html), JASPAR (see Nucleic Acids Res. 2018; 46(D1): D260-D266), and PROMO (see Messenger et al. Bioinformatics 2002; 18(2):333-334; Farré et al. Nucleic Acids Res. 2003; 31(13):3651-3653), each of which is incorporated herein by reference. The skilled worker will further appreciate that in situations where a homology arm is not 100% identical to the genomic sequence flanking the target locus, homologous recombination between the homology arm and the genome may alter the genomic sequence flanking the target locus such that it becomes identical to the sequence of the homology arm used.

In certain embodiments, the first genomic region 5' to the target locus is located in a first editing window, wherein the first editing window consists of the nucleotide sequence set forth in SEQ ID NO: 31, 32, or 34. In certain embodiments, the second genomic region 3' to the target locus is located in a second editing window, wherein the second editing window consists of the nucleotide sequence set forth in SEQ ID NO: 31, 32, or 34.

In certain embodiments, the first and second editing windows are different. In certain embodiments, the first editing window is located 5' to the second editing window. In certain embodiments, the first genomic region consists of a portion of the sequence of the first editing window in which the first genomic region is located. In certain embodiments, the first genomic region consists of the sequence of the first editing window in which the first genomic region is located. In certain embodiments, the second genomic region consists of a portion of the sequence of the second editing window in which the second genomic region is located. In certain embodiments, the second genomic region consists of the sequence of the second editing window in which the second genomic region is located. In certain embodiments, the first editing window consists of the nucleotide sequence set forth in SEQ ID NO: 31; and the second editing window consists of the nucleotide sequence set forth in SEQ ID NO: 32. In certain embodiments, the first genomic region 5' to the target locus consists of the sequence set forth in SEQ ID NO: 31. In certain embodiments, the second genomic region 3' to the target locus consists of the sequence set forth in SEQ ID NO: 32. In certain embodiments, the first genomic region 5' to the target locus and the second genomic region 3' to the target locus consist of the sequences set forth in SEQ ID NOs: 31 and 32, respectively.

In certain embodiments, the 5' homology arm consists of a nucleotide sequence at least about 90% (e.g., at least about 95%, 96%, 97%, 98%, 99%, or 99.5%) identical to the nucleotide sequence of SEQ ID NO: 31. In certain embodiments, the 5' homology arm consists of the nucleotide sequence set forth in SEQ ID NO: 31. In certain embodiments, the 3' homology arm consists of a nucleotide sequence at least about 90% (e.g., at least about 95%, 96%, 97%, 98%, 99%, or 99.5%) identical to the nucleotide sequence of SEQ ID NO: 32. In certain embodiments, the 3' homology arm consists of the nucleotide sequence set forth in SEQ ID NO: 32. In certain embodiments, the 5' and 3' homology arms consist of nucleotide sequences at least about 90% (e.g., at least about 95%, 96%, 97%, 98%, 99%, or 99.5%) identical to the nucleotide sequences of SEQ ID NOs: 31 and 32, respectively. In certain embodiments, the 5' and 3' homology arms consist of nucleotide sequences set forth in SEQ ID NOs: 31 and 32, respectively.

In certain embodiments, the first and second editing windows are the same. In certain embodiments, the target locus is an internucleotide bond or a nucleotide sequence in the editing window, wherein the first genomic region consists of a first portion of the editing window 5' to the target locus, and the second genomic region consists of a second portion of the editing window 3' to the target locus. In certain embodiments, the first portion of the editing window consists of the sequence from the 5' end of the editing window to the nucleotide adjacently 5' to the target locus. In certain embodiments, the second portion of the editing window consists of the sequence from the nucleotide adjacently 3' to the target locus to the 3' end of the editing window. In certain embodiments, the first portion of the editing window consists of the sequence from the 5' end of the editing window to the nucleotide adjacently 5' to the target locus, and the second portion of the editing window consists of the sequence from the nucleotide adjacently 3' to the target locus to the 3' end of the editing window. In certain embodiments, the editing window consists of the nucleotide sequence set forth in SEQ ID NO: 34. In certain embodiments, the first and second portions of the editing windows have substantially equal lengths (e.g., the ratio of the length of the shorter portion to the length of the longer portion is greater than 0.5, 0.55, 0.6, 0.65, 0.7, 0.75, 0.8, 0.85, 0.9, 0.95, 0.96, 0.97, 0.98, or 0.99).

In certain embodiments, the 5' homology arm consists of a nucleotide sequence at least about 90% (e.g., at least about 95%, 96%, 97%, 98%, 99%, or 99.5%) identical to a first portion of the nucleotide sequence of SEQ ID NO: 34. In certain embodiments, the 5' homology arm consists of a first portion of the nucleotide sequence of SEQ ID NO: 34. In certain embodiments, the 3' homology arm consists of a nucleotide sequence at least about 90% (e.g., at least about 95%, 96%, 97%, 98%, 99%, or 99.5%) identical to a second portion of the nucleotide sequence of SEQ ID NO: 34. In certain embodiments, the 3' homology arm consists of a second portion of the nucleotide sequence of SEQ ID NO: 34. In certain embodiments, the first portion is 5' to the second portion in SEQ ID NO: 34. In certain embodiments, the 5' and 3' homology arms consist of nucleotide sequences at least about 90% (e.g., at least about 95%, 96%, 97%, 98%, 99%, or 99.5%) identical to a first portion and a second portion, respectively, of the nucleotide sequences of SEQ ID NO: 34, wherein the first portion is 5' to the second portion in SEQ ID NO: 34. In certain embodiments, the 5' and 3' homology arms consist of a first portion and a second portion, respectively, of the nucleotide sequences of SEQ ID NO: 34, wherein the first portion is 5' to the second portion in SEQ ID NO: 34.

In certain embodiments, the first genomic region 5' to the target locus is located in a first editing window, wherein the first editing window consists of the nucleotide sequence set forth in SEQ ID NO: 34. In certain embodiments, the second genomic region 3' to the target locus is located in a second F8 targeting locus consisting of the nucleotide sequence set forth in SEQ ID NO: 34. In certain embodiments, the first genomic region 5' to the target locus is located in a first F8 targeting locus consisting of the nucleotide sequence set forth in SEQ ID NOs: 34; and the second genomic region 3' to the target locus is located in a second F8 targeting locus consisting of the nucleotide sequence set forth in SEQ ID NOs: 34.

In certain embodiments, the first genomic region 5' to the target locus comprises or consists of the sequence set forth in SEQ ID NO: 31. In certain embodiments, the second genomic region 3' to the target locus comprises or consists of the sequence set forth in SEQ ID NO: 32. In certain embodiments, the first genomic region 5' to the target locus and the second genomic region 3' to the target locus comprise or consist of the sequences set forth in SEQ ID NOs: 31 and 32, respectively.

In certain embodiments, the 5' homology arm has a length of about 50 to about 4500 nucleotides (e.g., about 100 to about 3000, about 200 to about 2500, about 300 to about 2000, about 400 to about 1500, about 500 to about 1000 nucleotides). In certain embodiments, the 5' homology arm has a length of about 800 nucleotides. In certain embodiments, the 5' homology arm has a length of about 100 nucleotides. In certain embodiments, the 3' homology arm has a length of about 50 to about 4500 nucleotides (e.g., about 100 to about 3000, about 200 to about 2500, about 300 to about 2000, about 400 to about 1500, about 500 to about 1000 nucleotides). In certain embodiments, the 3' homology arm has a length of about 800 nucleotides. In certain embodiments, the 3' homology arm has a length of about 100 nucleotides. In certain embodiments, each of the 5' and 3' homology arms independently has a length of about 50 to about 4500 nucleotides (e.g., about 100 to about 3000, about 200 to about 2500, about 300 to about 2000, about 400 to about 1500, about 500 to about 1000 nucleotides). In certain embodiments, each of the 5' and 3' homology arms has a length of about 800 nucleotides.

In certain embodiments, the 5' and 3' homology arms have substantially equal nucleotide lengths. In certain embodiments, the 5' and 3' homology arms have asymmetrical nucleotide lengths. In certain embodiments, the asymmetry in nucleotide length is defined by a difference between the 5' and 3' homology arms of up to 90% in the length, such as up to an 80%, 70%, 60%, 50%, 40%, 30%, 20%, or 10% difference in the length.

In certain embodiments, the correction genome comprises a nucleic acid sequence selected from the group consisting of SEQ ID NOs: 38-41.

In certain embodiments, the correction genomes disclosed herein further comprise a 5' inverted terminal repeat (5' ITR) nucleotide sequence 5' to the 5' homology arm nucleotide sequence, and a 3' inverted terminal repeat (3' ITR) nucleotide sequence 3' to the 3' homology arm nucleotide sequence. ITR sequences from any AAV serotype or variant thereof can be used in the correction genomes disclosed herein. The 5' and 3' ITR can be from an AAV of the same serotype or from AAVs of different serotypes. Exemplary ITRs for use in the correction genomes disclosed herein are set forth in SEQ ID NOs: 18-21, 46, 61, and 63 herein.

In certain embodiments, the 5' ITR or 3' ITR is from AAV2. In certain embodiments, both the 5' ITR and the 3' ITR are from AAV2. In certain embodiments, the 5' ITR nucleotide sequence has at least 95% (e.g., at least 96%, at least 97%, at least 98%, at least 99%, or 100%) sequence identity to SEQ ID NO: 18, or the 3' ITR nucleotide sequence has at least 95% (e.g., at least 96%, at least 97%, at least 98%, at least 99%, or 100%) sequence identity to SEQ ID NO: 19, 61, or 63. In certain embodiments, the 5' ITR nucleotide sequence has at least 95% (e.g., at least 96%, at least 97%, at least 98%, at least 99%, or 100%) sequence identity to SEQ ID NO: 18, and the 3' ITR nucleotide sequence has at least 95% (e.g., at least 96%, at least 97%, at least 98%, at least 99%, or 100%) sequence identity to SEQ ID NO: 19, 61, or 63. In certain embodiments, the correction genome comprises an editing element having the nucleic acid sequence set forth in SEQ ID NO: 34, a 5' ITR nucleotide sequence having the sequence of SEQ ID NO: 18, and a 3' ITR nucleotide sequence having the sequence of SEQ ID NO: 19, 61, or 63. In certain embodiments, the correction genome comprises the nucleic acid sequence set forth in SEQ ID NO: 34, a 5' ITR nucleotide sequence having the sequence of SEQ ID NO: 18, and a 3' ITR nucleotide sequence having the sequence of SEQ ID NO: 19, 61, or 63.

In certain embodiments, the 5' ITR or 3' ITR are from AAV5. In certain embodiments, both the 5' ITR and 3' ITR are from AAV5. In certain embodiments, the 5' ITR nucleotide sequence has at least 95% (e.g., at least 96%, at least 97%, at least 98%, at least 99%, or 100%) sequence identity to SEQ ID NO: 20, or the 3' ITR nucleotide sequence has at least 95% sequence identity to SEQ ID NO: 21. In certain embodiments, the 5' ITR nucleotide sequence has at least 95% (e.g., at least 96%, at least 97%, at least 98%, at least 99%, or 100%) sequence identity to SEQ ID NO: 20, and the 3' ITR nucleotide sequence has at least 95% (e.g., at least 96%, at least 97%, at least 98%, at least 99%, or 100%) sequence identity to SEQ ID NO: 21. In certain embodiments, the correction genome comprises an editing element having the nucleic acid sequence set forth in SEQ ID NO: 34, a 5' ITR nucleotide sequence having the sequence of SEQ ID NO: 20, and a 3' ITR nucleotide sequence having the sequence of SEQ ID NO: 21. In certain embodiments, the correction genome comprises the nucleic acid sequence set forth in SEQ ID NO: 34, a 5' ITR nucleotide sequence having the sequence of SEQ ID NO: 20, and a 3' ITR nucleotide sequence having the sequence of SEQ ID NO: 21.

In certain embodiments, the 5' ITR nucleotide sequence and the 3' ITR nucleotide sequence are substantially complementary to each other (e.g., are complementary to each other except for mismatch at 1, 2, 3, 4, or 5 nucleotide positions in the 5' or 3' ITR).

In certain embodiments, the 5' ITR or the 3' ITR is modified to reduce or abolish resolution by Rep protein ("non-resolvable ITR"). In certain embodiments, the non-resolvable ITR comprises an insertion, deletion, or substitution in the nucleotide sequence of the terminal resolution site. Such modification allows formation of a self-complementary, double-stranded DNA genome of the AAV after the transfer genome is replicated in an infected cell. Exemplary non-resolvable ITR sequences are known in the art (see e.g., those provided in U.S. Pat. Nos. 7,790,154 and 9,783,824, which are incorporated by reference herein in their entirety). In certain embodiments, the 5' ITR comprises a nucleotide sequence at least 95%, 96%, 97%, 98%, or 99% identical to SEQ ID NO: 46. In certain embodiments, the 5' ITR consists of a nucleotide sequence at least 95%, 96%, 97%, 98%, or 99% identical to SEQ ID NO: 46. In certain embodiments, the 5' ITR consists of the nucleotide sequence set forth in SEQ ID NO: 46. In certain embodiments, the 5' ITR and 3' ITR consist of the nucleotide sequences set forth in SEQ ID NOs: 46 and 19, respectively. In certain embodiments, the 5' ITR and 3' ITR consist of the nucleotide sequences set forth in SEQ ID NOs: 46 and 61, respectively.

In certain embodiments, the 5' ITR comprises a nucleotide sequence at least 95%, 96%, 97%, 98%, or 99% identical to the nucleotide sequence set forth in any one of SEQ ID NOs: 18, 20, 46. In certain embodiments, the 5' ITR consists of a nucleotide sequence at least 95%, 96%, 97%, 98%, or 99% identical to the nucleotide sequence set forth in any one of SEQ ID NOs: 18, 20, 46.

In certain embodiments, the 3' ITR comprises a nucleotide sequence at least 95%, 96%, 97%, 98%, or 99% identical to the nucleotide sequence set forth in any one of SEQ ID NOs: 19, 21, 61, 63. In certain embodiments, the 3' ITR consists of a nucleotide sequence at least 95%, 96%, 97%, 98%, or 99% identical to the nucleotide sequence set forth in any one of SEQ ID NOs: 19, 21, 61, 63.

In certain embodiments, the 3' ITR is flanked by an additional nucleotide sequence derived from a wild-type AAV2 genomic sequence. In certain embodiments, the 3' ITR is flanked by an additional 37 bp sequence derived from a wild-type AAV2 sequence that is adjacent to a wild-type AAV2 ITR. See, e.g., Savy et al., *Human Gene Therapy Methods* (2017) 28(5): 277-289 (which is hereby incorporated by reference herein in its entirety). In certain embodiments, the additional 37 bp sequence is internal to the 3' ITR. In certain embodiments, the 37 bp sequence consists of the sequence set forth in SEQ ID NO: 62 In certain embodiments, the 3' ITR comprises a nucleotide sequence at least 95%, 96%, 97%, 98%, or 99% identical to SEQ ID NO: 63. In certain embodiments, the 3' ITR comprises the nucleotide sequence set forth in SEQ ID NO: 63. In certain embodiments, the nucleotide sequence of the 3' ITR consists of a nucleotide sequence at least 95%, 96%, 97%, 98%, or 99% identical to SEQ ID NO: 63. In certain embodiments, the nucleotide sequence of the 3' ITR consists of the nucleotide sequence set forth in SEQ ID NO: 63.

In certain embodiments, the correction genome comprises a nucleic acid sequence selected from the group consisting of SEQ ID NOs: 42-45.

In certain embodiments, the correction genome consists of a nucleic acid sequence selected from the group consisting of SEQ ID NOs: 42-45.

In certain embodiments, the replication-defective AAV comprises: (a) an AAV capsid protein comprising the amino acid sequence of amino acids 203-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the replication-defective AAV comprises: (a) an AAV capsid protein comprising the amino acid sequence of amino acids 203-736 of SEQ ID NO: 16, and a correction genome comprising the nucleotide sequence set forth in SEQ ID NO: 26; (b) an AAV capsid protein comprising the amino acid sequence of amino acids 138-736 of SEQ ID NO: 16, and a correction genome comprising the nucleotide sequence set forth in SEQ ID NO: 26; and/or (c) an AAV capsid protein comprising the amino acid sequence of SEQ ID NO: 16, and a correction genome comprising the nucleotide sequence set forth in SEQ ID NO: 26.

In certain embodiments, the replication-defective AAV comprises: (a) an AAV capsid protein comprising the amino acid sequence of amino acids 203-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the replication-defective AAV comprises: (a) an AAV capsid protein comprising the amino acid sequence of amino acids 203-736 of SEQ ID NO: 13, and a correction genome comprising the nucleotide sequence set forth in SEQ ID NO: 26; (b) an AAV capsid protein comprising the amino acid sequence of amino acids 138-736 of SEQ ID NO: 13, and a correction genome comprising the nucleotide sequence set forth in SEQ ID NO: 26; and/or (c) an AAV capsid protein comprising the amino acid sequence of SEQ ID NO: 13, and a correction genome comprising the nucleotide sequence set forth in SEQ ID NO: 26.

The AAV compositions disclosed herein are particularly advantageous in that they are capable of correcting an F8 gene in a cell with high efficiency both in vivo and in vitro. In certain embodiments, the integration efficiency of the editing element into the target locus is at least 2% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of B lymphoblastoid cells under standard AAV transduction conditions for B lymphoblastoid cells. In certain embodiments, the allelic frequency of integration of the editing element into the target locus is at least 1% (e.g., at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of a exogenous nuclease with a population of B lymphoblastoid cells under standard AAV transduction conditions for B lymphoblastoid cells. In certain embodiments, the integration efficiency of the editing element into the target locus in the liver is at least 2% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of an exogenous nuclease or a nuclease sequence that encodes an exogenous nuclease under standard AAV administration conditions. In certain embodiments, the allelic frequency of integration of the editing element into the target locus in the liver is at least 1% (e.g., at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of a exogenous nuclease or a nuclease sequence that encodes an exogenous nuclease under standard AAV administration conditions. As used herein, the term "standard AAV administration conditions" refers to administration of an AAV intravenously at a dose of $1.5 \times 10^5$ vector genomes per kilogram of body weight for a subject having the size and body shape of a mouse. A skilled worker will appreciate that the dose should be adjusted according to the size and body shape of the subject to achieve similar predicted efficacy. An exemplary dose conversion between species is provided by Nair et al. (2016) J. Basic Clin. Pharm. 7(2): 27-31, which is incorporated by reference herein in its entirety.

Any methods of determining the efficiency of editing of the F8 gene can be employed. In certain embodiments, individual cells are separated from the population of transduced cells and subject to single-cell PCR using PCR primers that can identify the presence of an editing element correctly integrated into the target locus of the F8 gene. Such method can further comprise single-cell PCR of the same cells using PCR primers that selectively amplify an unmodified target locus. In this way, the genotype of the cells can be determined. For example, if the single-cell PCR showed that a cell has both an edited target locus and an unmodified target locus, then the cell would be considered heterozygous for the edited F8 gene.

Additionally or alternatively, in certain embodiments, linear amplification mediated PCR (LAM-PCR), quantitative PCR (qPCR), or digital droplet PCR (ddPCR) can be performed on DNA extracted from the population of transduced cells using primers and probes that only detect edited F8 alleles. Such method can further comprise an additional qPCR or ddPCR (either in the same reaction or a separate reaction) to determine the number of total genomes in the sample and the number of unedited F8 alleles. These numbers can be used to determine the allelic frequency of integration of the editing element into the target locus.

Additionally or alternatively, in certain embodiments, the F8 locus can be amplified from DNA extracted from the population of transduced cells either by PCR using primers that bind to regions of the F8 gene flanking the genomic region encompassed by the correction genome, or by linear amplification mediated PCR (LAM-PCR) using a primer that binds a region within the correction genome (e.g., a region comprising an exogenous sequence non-native to the locus. The resultant PCR amplicons can be individually sequenced using single molecule next generation sequencing (NGS) techniques to determine the relative number of edited and unedited F8 alleles present in the population of transduced cells. These numbers can be used to determine the allelic frequency of integration of the editing element into the target locus.

In another aspect, the instant disclosure provides pharmaceutical compositions comprising an AAV as disclosed herein together with a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., 7th ed., Lippincott, Williams, & Wilkins; and Handbook of Pharmaceutical Excipients (2000) A. H. Kibbe et al., 3rd ed. Amer. Pharmaceutical Assoc.

III. Methods of Use

In another aspect, the instant disclosure provides methods for correcting a mutation in the F8 gene or expressing a FVIII polypeptide in a cell. The methods generally comprise transducing the cell with a replication-defective AAV as disclosed herein. Such methods are highly efficient at correcting mutations in the F8 gene or restoring F8 expression, and do not require cleavage of the genome at the target locus by the action of an exogenous nuclease (e.g., a meganuclease, a zinc finger nuclease, a transcriptional activator-like nuclease (TALEN), or an RNA-guided nuclease such as a Cas9) to facilitate such correction. Accordingly, in certain embodiments, the methods disclosed herein involve transducing the cell with a replication-defective AAV as disclosed herein without co-transducing or co-administering an exogenous nuclease or a nucleotide sequence that encodes an exogenous nuclease.

The methods disclosed herein can be applied to any cell harboring a mutation in any or all of exons 23-26 or any or all of introns 22-25 of the F8 gene. The skilled worker will appreciate that cells that are active in F8 expression are of particular interest. Accordingly, in certain embodiments, the method is applied to hepatocytes, liver sinusoidal endothelial cells and/or other endothelial cells. In certain embodiments, the method is applied to a liver. The cells or liver can be in a subject (e.g., a human subject).

The methods disclosed herein can be performed in vitro for research purposes or can be performed ex vivo or in vivo for therapeutic purposes.

In certain embodiments, the cell to be transduced is in a mammalian subject and the AAV is administered to the subject in an amount effective to transduce the cell in the subject. Accordingly, in certain embodiments, the instant disclosure provides a method for treating a subject having a disease or disorder associated with an F8 gene mutation, the method generally comprising administering to the subject an effective amount of a replication-defective AAV as disclosed herein. The subject can be a human subject or a rodent subject (e.g., a mouse) containing human liver cells. Suitable mouse subjects include without limitation, mice into which human liver cells (e.g., human hepatocytes and human hepatic sinusoidal endothelial cell) have been engrafted. Hemophilia A or any other disorder associated with an F8 gene mutation in any or all of exons 23-26 or any or all of introns 22-25 can be treated using the methods disclosed herein. In certain embodiments, the cell is transduced without co-transducing or co-administering an exogenous nuclease or a nucleotide sequence that encodes an exogenous nuclease.

In certain embodiments, the foregoing methods emply a replication-defective AAV comprises: (a) an AAV capsid protein comprising the amino acid sequence of amino acids 203-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 16, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the foregoing methods emply a replication-defective AAV comprises: (a) an AAV capsid protein comprising the amino acid sequence of amino acids 203-736 of SEQ ID NO: 16, and a correction genome comprising the nucleotide sequence set forth in SEQ ID NO: 26; (b) an AAV capsid protein comprising the amino acid sequence of amino acids 138-736 of SEQ ID NO: 16, and a correction genome comprising the nucleotide sequence set forth in SEQ ID NO: 26; and/or (c) an AAV capsid protein comprising the amino acid sequence of SEQ ID NO: 16, and a correction genome comprising the nucleotide sequence set forth in SEQ ID NO: 26.

In certain embodiments, the foregoing methods emply a replication-defective AAV comprises: (a) an AAV capsid protein comprising the amino acid sequence of amino acids 203-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); (b) an AAV capsid protein comprising the amino acid sequence of amino acids 138-736 of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63); and/or (c) an AAV capsid protein comprising the amino acid sequence of SEQ ID NO: 13, and a correction genome comprising 5' to 3' the following genetic elements: a 5' ITR element (e.g., the 5' ITR of SEQ ID NO: 18), a 5' homology arm (e.g., the 5' homology arm of SEQ ID NO: 27 or 31), the coding sequence of exons 23-26 of human F8 (e.g., the coding sequence of SEQ ID NO: 26), an optional SV40 polyadenylation sequence (e.g., the SV40 polyadenylation sequence of SEQ ID NO: 37), a 3' homology arm (e.g., the 3' homology arm of SEQ ID NO: 28 or 32), and a 3' ITR element (e.g., the 3' ITR of SEQ ID NO: 19, 61, or 63).

In certain embodiments, the foregoing methods emply a replication-defective AAV comprises: (a) an AAV capsid protein comprising the amino acid sequence of amino acids 203-736 of SEQ ID NO: 13, and a correction genome comprising the nucleotide sequence set forth in SEQ ID NO: 26; (b) an AAV capsid protein comprising the amino acid sequence of amino acids 138-736 of SEQ ID NO: 13, and a correction genome comprising the nucleotide sequence set forth in SEQ ID NO: 26; and/or (c) an AAV capsid protein comprising the amino acid sequence of SEQ ID NO: 13, and a correction genome comprising the nucleotide sequence set forth in SEQ ID NO: 26.

The methods disclosed herein are particularly advantageous in that they are capable of correcting an F8 gene in a cell with high efficiency both in vivo and in vitro. In certain embodiments, the integration efficiency of the editing element into the target locus is at least 2% (e.g. at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of an exogenous nuclease with a population of B lymphoblastoid cells under standard AAV transduction conditions for B lymphoblastoid cells. In certain embodiments, the allelic frequency of integration of the editing element into the target locus is at least 1% (e.g. at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is contacted in vitro in the absence of a exogenous nuclease with a population of B lymphoblastoid cells under standard AAV transduction conditions for B lymphoblastoid cells. In certain embodiments, the integration efficiency of the editing element into the target locus in the liver is at least 2% (e.g., at least 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of an exogenous nuclease or a nuclease sequence that encodes an exogenous nuclease under standard AAV administration conditions. In certain embodiments, the allelic frequency of integration of the editing element into the target locus in the liver is at least 1% (e.g., at least 1%, 1.5%, 2%, 2.5%, 3%, 3.5%, 4%, 4.5%, 5%, 7.5%, 10%, 15%, 20%, 25%, 30%, 35%, 40%, 45%, 50%, 55%, 60%, 65%, 70%, 75%, 80%, 85%, 90%, or 95%) when the AAV is administered to a subject in the absence of a exogenous nuclease or a nuclease sequence that encodes an exogenous nuclease under standard AAV administration conditions. As used herein, the term "standard AAV administration conditions" refers to administration of an AAV intravenously at a dose of $1.5 \times 10^5$ vector genomes per kilogram of body weight for a subject having the size and body shape of a mouse. A skilled worker will appreciate that the dose should be adjusted according to the size and body shape of the subject to achieve similar predicted efficacy. An exemplary dose conversion between species is provided by Nair et al. (2016) J. Basic Clin. Pharm. 7(2): 27-31, which is incorporated by reference herein in its entirety. Any methods of determining the efficiency of editing of the F8 gene can be employed including, without limitation, those described herein.

The methods disclosed herein are also advantageous in that they are capable of expressing a FVIII protein in a cell with high efficiency both in vivo and in vitro. In certain embodiments, the expression level of the FVIII protein is at least 10%, 20%, 30%, 40%, 50%, 60%, 70%, 80%, 90%, or 100% of the expression level of the endogenous FVIII protein in a cell of the same type that does not have a mutation in the F8 gene. In certain embodiments, the expression level of the FVIII protein is at least 1.1, 1.2, 1.3, 1.4, 1.5, 1.6, 1.7, 1.8, 1.9, 2, 3, 4, 5, 6, 7, 8, 9, or 10 fold higher than the expression level of the endogenous FVIII protein in a cell of the same type that does not have a mutation in the F8 gene. Any methods of determining the expression level of the FVIII protein can be employed including, without limitation, ELISA, Western blotting, immunostaining, and mass spectrometry.

In certain embodiments, transduction of a cell with an AAV composition disclosed herein can be performed as provided herein or by any method of transduction known to one of ordinary skill in the art. In certain embodiments, the cell may be contacted with the AAV at a multiplicity of infection (MOI) of 50,000; 100,000; 150,000; 200,000; 250,000; 300,000; 350,000; 400,000; 450,000; or 500,000, or at any MOI that provides for optimal transduction of the cell.

An AAV composition disclosed herein can be administered to a subject by any appropriate route including, without limitation, intravenous, intraperitoneal, subcutaneous, intramuscular, intranasal, topical or intradermal routes. In certain embodiments, the composition is formulated for administration via intravenous injection or subcutaneous injection.

IV. AAV Packaging Systems

In another aspect, the instant disclosure provides packaging systems for recombinant preparation of a replication-defective AAV disclosed herein. Such packaging systems generally comprise: a Rep nucleotide sequence encoding one or more AAV Rep proteins; a Cap nucleotide sequence encoding one or more AAV Clade F capsid proteins as disclosed herein; and a correction genome for correction of the F8 gene as disclosed herein, wherein the packaging system is operative in a cell for enclosing the correction genome in the capsid to form the AAV.

In certain embodiments, the packaging system comprises a first vector comprising the Rep nucleotide sequence and the Cap nucleotide sequence, and a second vector comprising the correction genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

Any AAV Rep protein can be employed in the packaging systems disclosed herein. In certain embodiments of the packaging system, the Rep nucleotide sequence encodes an AAV2 Rep protein. Suitable AAV2 Rep proteins include, without limitation, Rep 78/68 or Rep 68/52. In certain embodiments of the packaging system, the AAV2 Rep protein comprises an amino acid sequence having a minimum percent sequence identity to the AAV2 Rep amino acid sequence of SEQ ID NO: 22, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein. In certain embodiments of the packaging system, the AAV2 Rep protein has the amino acid sequence set forth in SEQ ID NO: 22.

In certain embodiments of the packaging system, the packaging system further comprises a third vector, e.g., a helper virus vector. The third vector may be an independent third vector, integral with the first vector, or integral with the second vector. In certain embodiments, the third vector comprises genes encoding helper virus proteins.

In certain embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In certain embodiments of the packaging system, where the helper virus is adenovirus, the adenovirus genome comprises one or more adenovirus RNA genes selected from the group consisting of E1, E2, E4 and VA. In certain embodiments of the packaging system, where the helper virus is HSV, the HSV genome comprises one or more of HSV genes selected from the group consisting of UL5/8/52, ICPO, ICP4, ICP22 and UL30/UL42.

In certain embodiments of the packaging system, the first, second, and/or third vector are contained within one or more transfecting plasmids. In certain embodiments, the first vector and the third vector are contained within a first transfecting plasmid. In certain embodiments the second vector and the third vector are contained within a second transfecting plasmid.

In certain embodiments of the packaging system, the first, second, and/or third vector are contained within one or more recombinant helper viruses. In certain embodiments, the first vector and the third vector are contained within a recombinant helper virus. In certain embodiments, the second vector and the third vector are contained within a recombinant helper virus.

In a further aspect, the disclosure provides a method for recombinant preparation of an AAV as described herein, wherein the method comprises transfecting or transducing a cell with a packaging system as described under conditions operative for enclosing the correction genome in the capsid to form the AAV as described herein. Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including HSV, cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Clade F capsid proteins as described herein, and with a correction genome as described herein being delivered in the form of a transfecting plasmid or a recombinant helper virus).

V. Examples

The recombinant AAV vectors disclosed herein mediate highly efficient gene editing or gene transfer in vitro and in vivo. The following examples demonstrate the efficient restoration of the expression of the F8 gene which is mutated in certain human diseases, such as hemophilia A, using an AAV-based vector as disclosed herein. These examples are offered by way of illustration, and not by way of limitation.

Example 1: Editing of the Human F8 Gene Locus Using AAV Vectors

This example provides F8 correction vectors VG-F8-002-FP and VG-F8-003-FP, each containing an editing element for insertion of a reporter (a fluorescent protein (FP)) coding sequence after exon 22 or into intron 22, respectively, of the human F8 gene.

VG-F8-002-FP

The VG-F8-002-FP vector, as shown in FIG. 1A, encompasses 5' to 3': a 5' ITR; a 5' homology arm consisting of the sequence of nucleotides 125,677-126,476 of human F8 gene; a T2A element; a FP coding sequence; a nuclear localization signal (NLS) encoding sequence; an SV40 polyadenylation sequence; a 3' homology arm consisting of the sequence of nucleotides 126,477-127,276 of human F8 gene; and a 3' ITR.

Integration of the F8 specific correction vector VG-F8-002-FP into the human genome inserts the T2A element, the FP coding sequence, the NLS, and the SV40 polyadenylation sequence after the last codon of the exon 22 of the human F8 gene. The T2A peptide leads to generation of two polypeptides: a truncated F8 peptide terminated at the end of exon 22 fused with an N-terminal part of the T2A peptide, and a full-length FP polypeptide with a proline from the T2A peptide remaining at the N-terminus. Integration of this vector thereby directs the expression of the fluorescent protein under the control of the F8 promoter which is present in the human genome but not provided in the VG-F8-002-FP vector.

VG-F8-003-FP

Figure 1B:
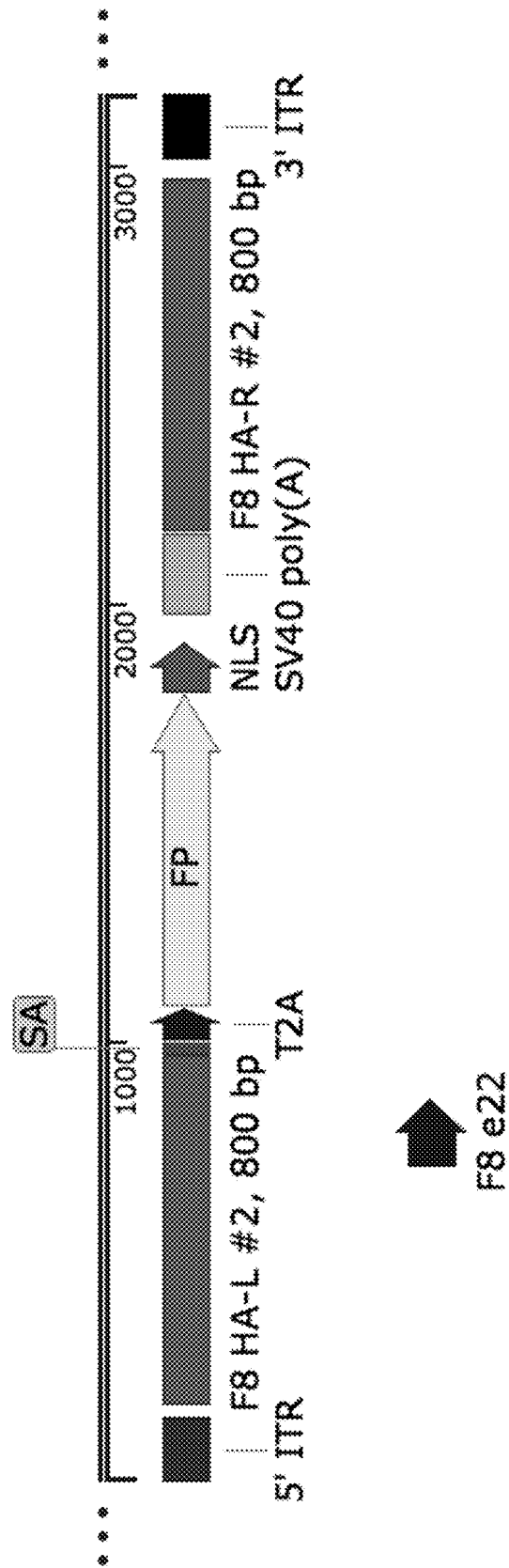

The VG-F8-003-FP vector, as shown in FIG. 1B, encompasses 5' to 3': a 5' ITR; a 5' homology arm consisting of the sequence of nucleotides 125,777-126,576 of human F8 gene; a splice acceptor element; a T2A element; coding sequence for FP; an NLS encoding sequence; an SV40 polyadenylation sequence; a 3' homology arm consisting of the sequence of nucleotides 126,577-127,376 of human F8 gene, and a 3' ITR.

Integration of the F8 specific correction vector VG-F8-003-FP into the human genome inserts the splice acceptor, T2A element, the FP coding sequence, the NLS encoding sequence, and the SV40 polyadenylation sequence after nucleotide 126,576 of the human F8 gene in intron 22. The mRNA transcribed from the edited F8 locus comprises exons 1-22 of the human F8 gene, the T2A element, the FP coding sequence, and the NLS encoding sequence. The 2A peptide leads to generation of two polypeptides: a truncated FVIII peptide terminated at the end of exon 22 fused with an N-terminal part of the 2A peptide, and a full-length FP polypeptide with a proline from the 2A peptide remaining at the N-terminus. Integration of this vector thereby directs the expression of the fluorescent protein under the control of the F8 promoter which is present in the human genome but not provided in the VG-F8-003-FP vector.

VG-F8-002-FP and VG-F8-003-FP were examined in vitro for assessment of targeted integration. B lymphoblastoid cell lines 16756, 14623, and 13023 were cultured in RPMI supplemented with 15% fetal calf serum (FCS) and 2 mM L-glutamine. Cells were seeded at approximately 200,000 cells per mL and split when cells reached between 500,000 to 1,000,000 cells per mL.

Vectors were packaged with AAVHSC17, and the viral particles were tested for their ability to edit the human F8 gene in B lymphoblastoid cells. AAVHSC-AAVS1-FP, an AAV vector comprising AAV2 ITRs, homology arms for genome integration into the AAVS1 locus, and a promoterless fluorescent protein, serves as a control for gene integration (see e.g., WO 2016/049230 A1, which is incorporated by reference herein in its entirety).

Cells were in log phase growth on the day of transduction. Cells were counted and an appropriate number of cells were plated. Typically, 10,000 cells were plated for flow cytometry analysis. Vector did not exceed 10% of the culture volume. Vector was calculated based on the titer and MOI and was calculated before plating to ensure proper plates were used.

Vectors were thawed on ice and sonicated on ice if necessary prior to transductions. Virus was added to each well individually and media was pipetted up and down to evenly distribute virus. 48 hours after transduction, cells transduced with AAVF F8 FP vectors were harvested using FACS Buffer (1×PBS, 2% FCS, 0.1% sodium azide). Cells were spun down at 1200 RPM for 10 minutes. FACS buffer was removed so that approximately 200 µL remained. DAPI (100 µM working stock) was added immediately before flow cytometry analysis to a final concentration of 3 µM.

Figure 2:
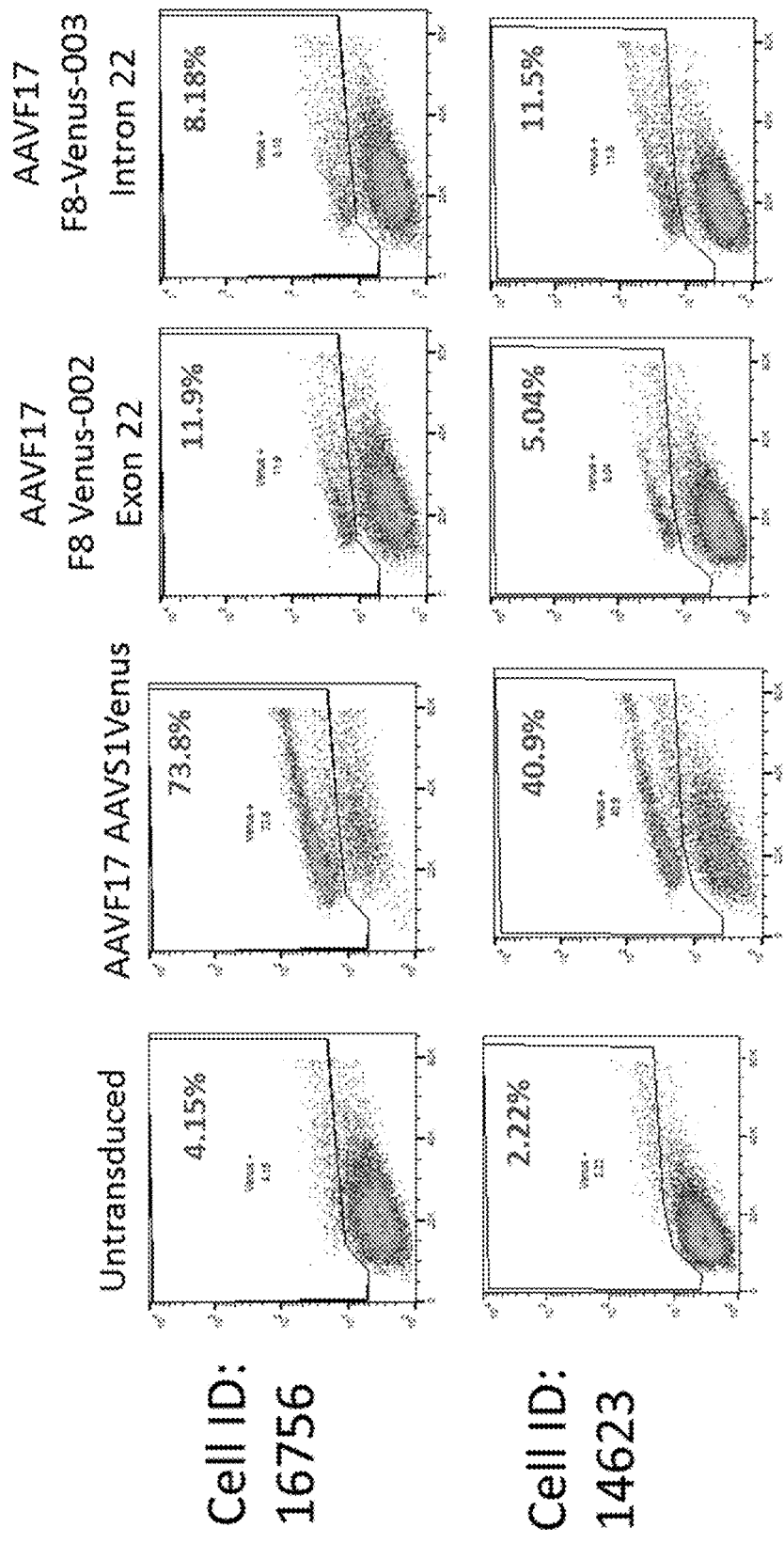
FIG. 2 is a series of graphs depicting editing of the human F8 locus as measured by flow cytometry with three B lymphoblastoid transduced with reporter vectors.
Figure 2:
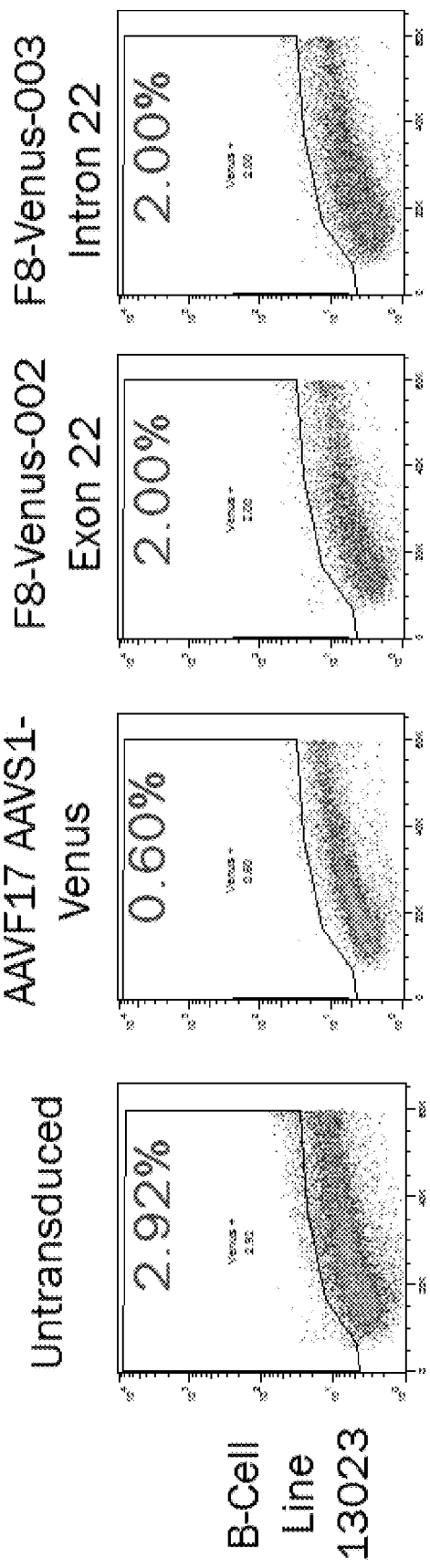

The rate of gene editing was calculated by subtracting the percentage of FP-positive cells in an untransduced sample from the percentage of FP-positive cells in the corresponding transduced sample. As shown in FIG. 2, about 3-8% of FANCD2 heterozygous B lymphoblastoid cells (Cell ID: 16756) were edited by the VG-F8-002-FP vector packaged in AAVHSC17 capsid in the human F8 locus, and about 4-9% of and FANCD1 heterozygous B lymphoblastoid cells (Cell ID: 14623) were edited by the VG-F8-003-FP packaged in AAVHSC17 capsid in the human F8 locus. In contrast, the rate of gene editing in FANCD1 (an essential mediator of homologous recombination also named BRCA2)-deficient B lymphoblastoid cells (Cell ID: 13023) was not detectable. In sum, these data show editing of the F8 gene locus using AAV vectors, and further, that the observed editing is mediated by homologous recombination.

Example 2: Human Tissues Capable of Expressing F8

Figure 3:
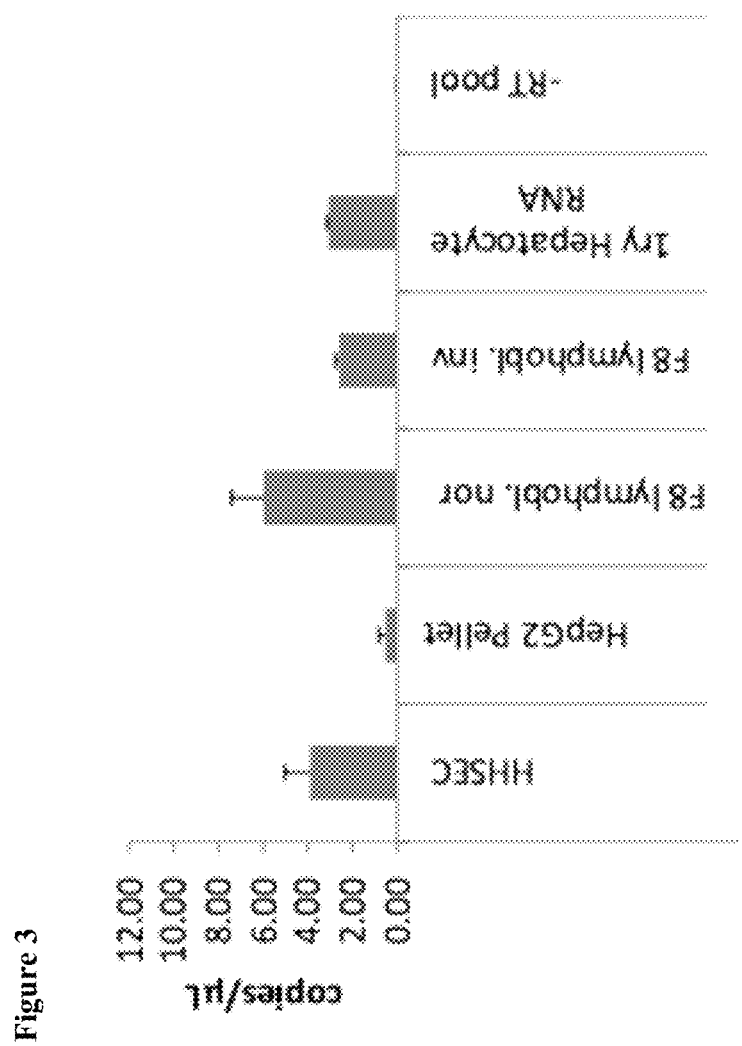
FIG. 3 is a graph showing the mRNA expression of F8 in mammalian cells.

The expression of F8 may be restored in one or more cell types that are capable of expressing F8. FIG. 3 shows the levels of F8 mRNA in primary human hepatic sinusoidal endothelial cells ("HHSEC"), human hepatoma HepG2 cells ("HepG2"), B lymphoblasts from a normal individual ("F8 lymphobl.nor"), B lymphoblasts from a patient harboring the F8 intron 22 inversion ("F8 lymphobl.inv"), and primary human hepatocytes ("1ry Hepatocyte RNA"). These levels were measured by digit droplet PCR (ddPCR) following the protocol described below.

Frozen cell pellets were used for RNA isolation. Cells were thawed and washed with PBS to remove the DMSO. Total RNA was isolated from cell pellets using the RNeasy mini kit (Qiagen), and concentration was measured with SimpliNano (GE healthcare). 900 ng of RNA per cell type was used for a RT reaction to create cDNA, with the exception of the B lymphoblasts from a patient harboring the F8 intron 22 inversion, wherein 450 ng of RNA was used for the RT reaction. This was corrected in the final data analysis.

TaqMan® Reverse Transcription Reagents (Applied Bioscience, Cat. N8080234) were used for generating cDNA. The TaqMan® primers and probes used are shown in Table 1 below. Complementary DNA samples were diluted 1:3 in distilled water and a mixture was made of 10 µl Master mix, 1 µl of FAM probe (F8), 1 µl of VIC probe (GAPDH) and 8 µl of diluted cDNA. Droplets were generated using the DG8 cartridge, according to the QX200 Droplet generator Manual (Bio-Rad #10031907). The cycle parameters for the ddPCR are described in Table 2. After the PCR, the droplets were read on the QX200 droplet reader and analyzed using the Quantasoft Software.

TABLE 1

TaqMan® primers and probes used for quantifying F8 mRNA

| Assay ID | Assay name | Cat # | Lot # |
|---|---|---|---|
| Hs00252034_m1 | F8 | 4331182 | 1276586 |
| Hs00240767_m1 | F8 | 4331182 | 1418037 |
| Hs02758991_g1 | GAPDH | 4448490 | P150630-001 H10 |

TABLE 2

Cycle parameters for ddPCR

| Cycling step | Temp, ° C. | Time | ramp rate | # of cycles |
|---|---|---|---|---|
| Enzyme activation | 95 | 10 min | 2 C./sec | 1 |
| Denaturation | 94 | 30 sec | | 40 |
| Annealing/extension | 60 | 1 min | | 40 |
| Enzyme deactivation | 98 | 10 min | | 1 |
| Hold(optional) | 12 | infinite | | 1 |

Example 3: In Vivo Editing of the Murine F8 Gene Locus Using AAV Vectors

Figure 4A:
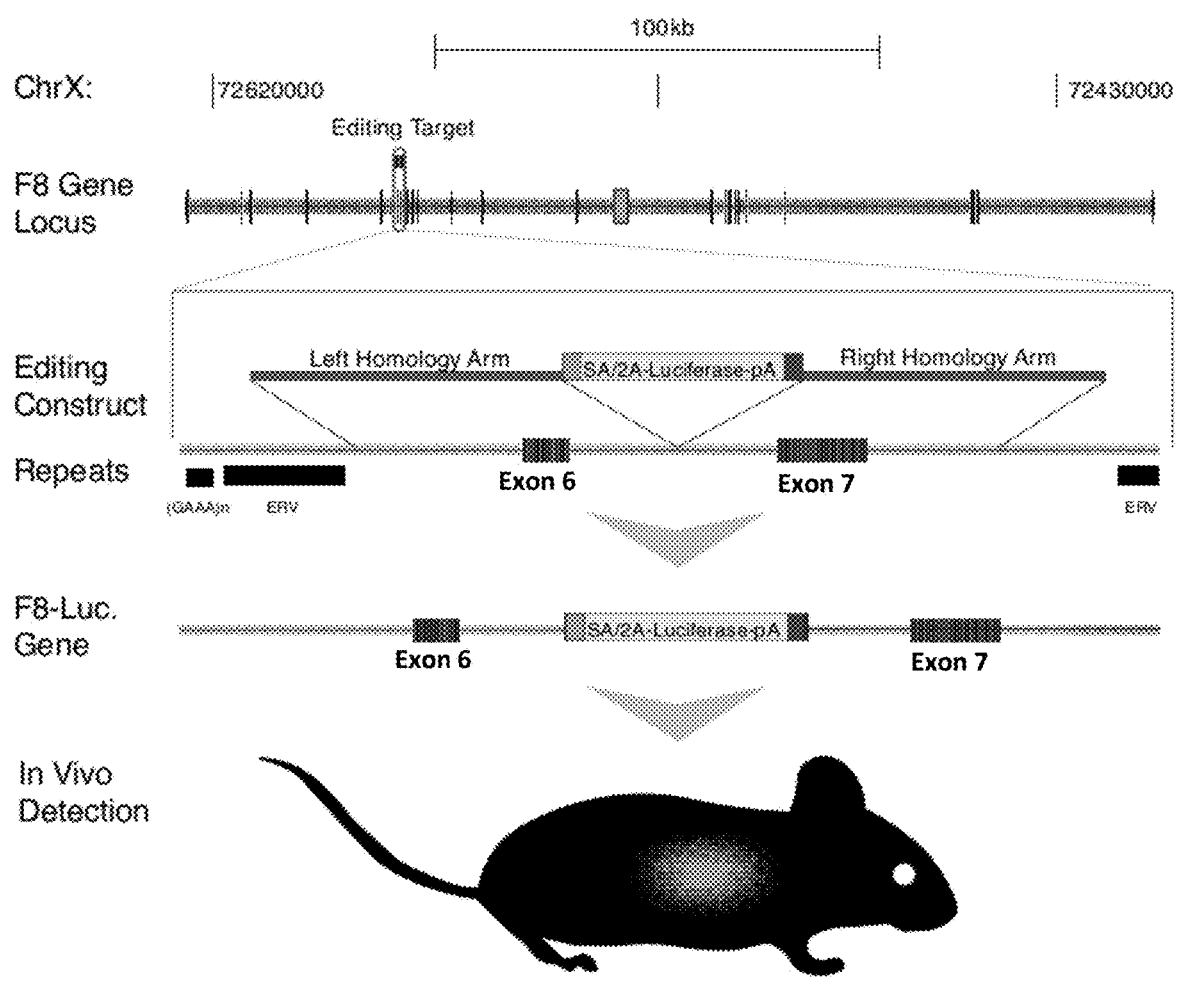
FIG. 4A is a map of the VG-mF8-001-Luc vector and its expected integration into a mouse genome.

This example provides in vivo editing of the F8 locus after administration of VG-mF8-001-Luc vector. A map of the VG-mF8-001-Luc vector is shown in FIG. 4A. This vector comprises 5' to 3' a 5' ITR (not shown), a left homology arm having homology to a first sequence from intron 5 to intron 6 of mouse F8 ("HAL," having the sequence of nucleotides 48,303-49,102 of mouse F8), a splice acceptor ("SA"), a T2A element ("2A"), a promoter-less nucleotide sequence encoding luciferase ("Luc ORF"), an SV40 polyadenylation sequence ("pA"), a right homology arm having homology to a second sequence from intron 6 to intron 7 of mouse F8 ("HAR," having the sequence of nucleotides 49,103-49,902 of mouse F8), and a 3' ITR (not shown).

Integration of the VG-mF8-001-Luc vector into the mouse genome inserts the splice acceptor, T2A element, the luciferase coding sequence, and the SV40 polyadenylation sequence in intron 6 of the mouse F8 gene. The mRNA transcribed from the edited F8 locus comprises exons 1-6 of the mouse F8 gene, the T2A element, and the luciferase coding sequence. The T2A peptide leads to generation of two polypeptides: a truncated FVIII peptide terminated at the end of exon 6 fused with an N-terminal part of the T2A peptide, and a full-length luciferase polypeptide with a proline from the 2A peptide remaining at the N-terminus. Integration of this vector thereby directs the expression of the luciferase protein under the control of the F8 promoter which is present in the mouse genome but not provided in the VG-mF8-001-Luc vector.

Figure 4B:
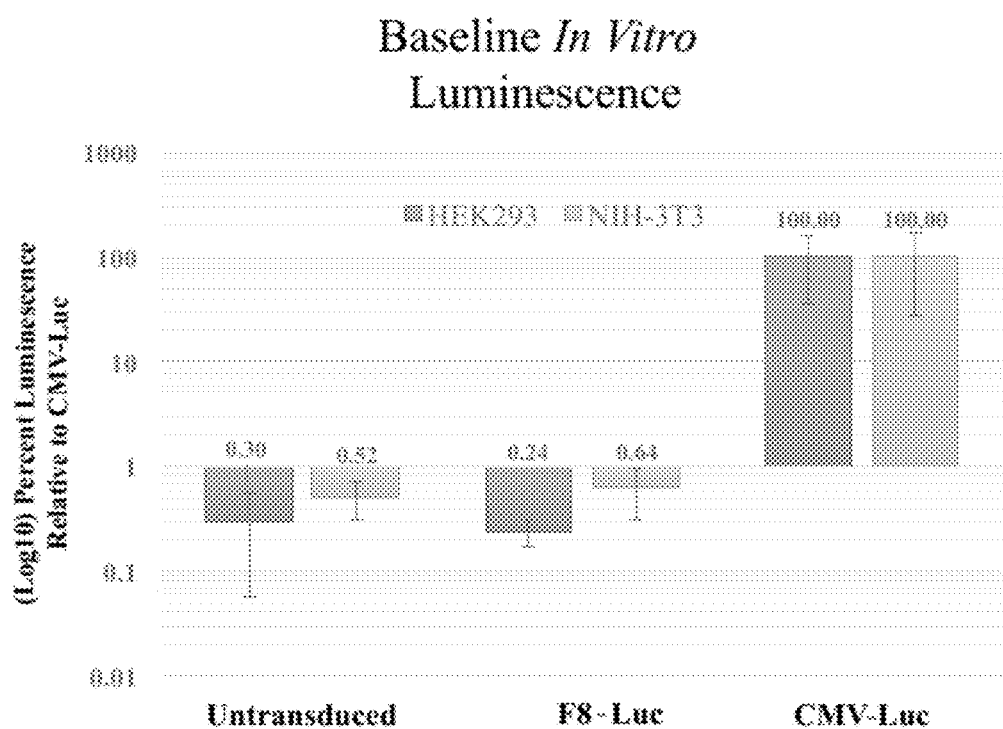
FIG. 4B is a graph showing bioluminescence from HEK293 and NIH3T3 cells transfected with the VG-mF8-001-Luc vector.

The homology arm sequences did not include predicted hallmarks of transcriptional regulatory elements that might act to drive episomal luciferase expression (see transcriptional regulatory elements predicted in Sabo et al. (2006) Nat Methods 3: 511-18; Griffith et al. (2008) Nucleic Acids Res 36: D107-13; and Rando et al. (2009) Annu Rev Biochem 78: 245-71). To ensure that a luciferase protein did not express from the editing vector without genome integration, the VG-mF8-001-Luc vector was transfected into human HEK293 and mouse NIH3T3 cells. As shown in FIG. 4B, no bioluminescence was detected from the transfected cells 24 hours after transfection. By contrast, bioluminescence was detected from the cells transfected with a positive control vector comprising a luciferase encoding sequence driven by a CMV promoter. While not wishing to be bound by theory, it is hypothesized that the vector did not substantially integrate into the genome of NIH3T3 cells because the rate of homologous recombination was low by transfection, i.e., in the absence of the AAVHSC delivery apparatus.

Figure 4C:
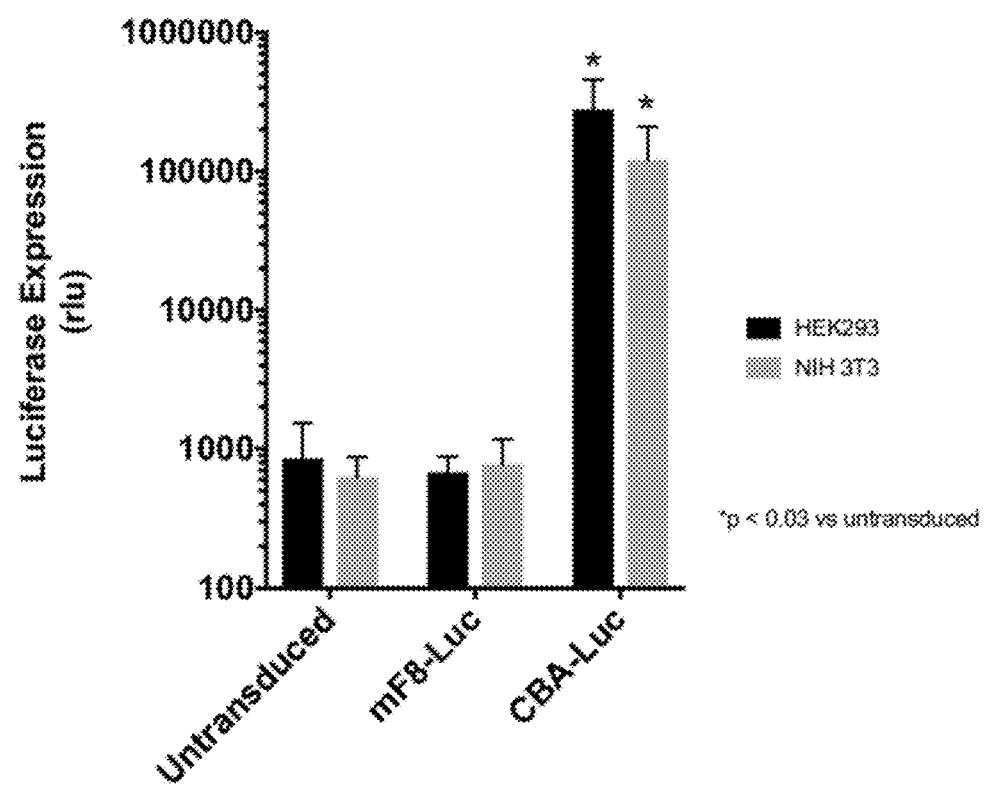
FIG. 4C is a graph showing luciferase expression in relative luminometer units (RLU) from HEK293 and NIH3T3 cells transfected with the VG-mF8-001-Luc vector.

FIG. 4C is a graph showing luciferase expression in relative luminometer units (RLU) from HEK293 and NIH3T3 cells transfected with the VG-mF8-001-Luc vector. As shown in FIG. 4C, luciferase expression was measured to be the same between HEK293 and NIH3T3 cells transfected with the VG-mF8-001-Luc vector, and HEK293 and NIH3T3 cells that were untransduced. In contrast, luciferase expression was detected from cells transfected with a positive control vector comprising a luciferase encoding sequence driven by a chicken β-actin (CBA) promoter.

The VG-mF8-001-Luc vector was packaged in AAVHSC15 or AAVHSC17 (see WO 2016/049230 A1, which is incorporated by reference herein in its entirety). A control vector named VG-ΔSA-mF8-001-Luc, which was different from VG-mF8-001-Luc in the absence of the splice acceptor, was also packaged in AAVHSC15. To ensure consistent AAV virus quality, each vector was analyzed across a panel of characteristics; DNA and capsid titer, vector protein purity by silver stain, capsid protein western-blot and endotoxin burden. There were no significant differences in vector purity, quality or titer between each vector preparation. Female C57BL/6 mice 6-8-week old obtained from Charles River Laboratories received either a low dose of $1\times10^{10}$ vector genomes (approximately $5\times10^{11}$ vector genomes per kilogram of body weight) or a high dose of $3\times10^{12}$ vector genomes (approximately $1.5\times10^{14}$ vector genomes per kilogram of body weight) that was injected intravenously via tail vein at a maximum of 10 ml/kg to each mouse. Serial bioluminescent imaging was performed on anesthetized mice that were injected intraperitoneally with 0.15 mg/g of luciferin (Caliper Life Sciences). Images were taken 10 minutes after luciferin injection using a SPECTRAL LagoX imaging system (Spectral Instruments Imaging, LLC). Mice were imaged for 5 minutes with large binning ventrally. Organs were then harvested and imaged. Images were analyzed using AMIView software version 1.7.06.

To detect editing of the F8 gene, liver samples were collected from mice after administration of the AAV vectors, total DNA was isolated from the samples using the QIAamp DNA mini kit (Qiagen), and DNA concentrations were measured with NanoDrop (ThermoFisher). The DNA samples was analyzed by the following methods:

End-Point PCR

Figure 5A:
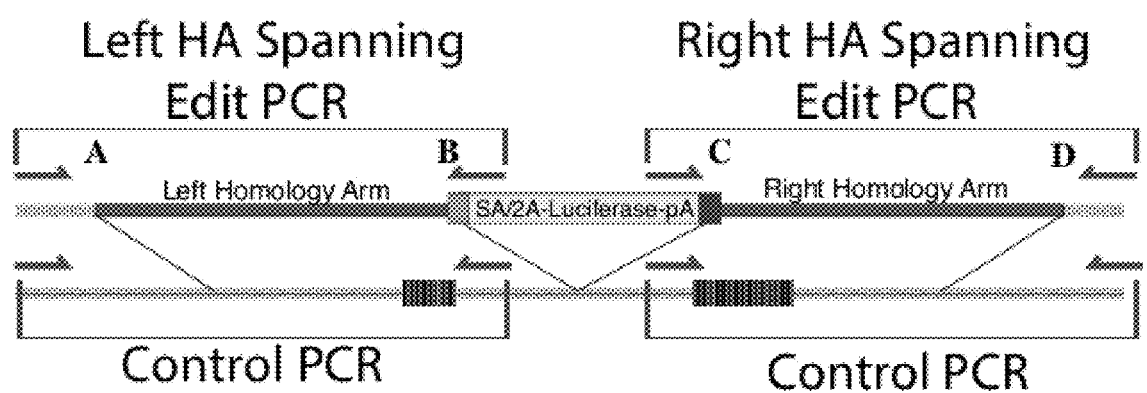
FIG. 5A illustrates two PCR designs for detecting homologous recombination of the VG-mF8-001-Luc vector into the mouse genome.

Liver genomic DNA was analyzed by end-point PCR using primers specific for integration of the luciferase cassette into the target site. The primer sequences are provided in Table 3 below, and their targeting regions are shown in FIG. 5A. The PCR conditions are provided in Table 4. As genomic PCR controls, comparably sized PCRs were run spanning each homology arm. The specificity of each amplicon was confirmed by Sanger sequencing.

TABLE 3

Primers for quantifying F8 edited DNA by end-point PCR

| Assay name | Primer name | Target region | Sequences | SEQ ID NO |
|---|---|---|---|---|
| Left HA Edit PCR | F8_LeftA_F | 5' homology arm | GGAAGAGCTGGCACTCAGAA | 53 |
|  | F8_LeftA_R | editing element | CTTAATATTCTTGGCATCCTCCATG | 54 |
| Left HA Control PCR | F8_LeftB_F | genomic sequence | GCTCCAGAATACACGGTTGTG | 55 |
|  | F8_LeftB_R | 5' homology arm | CCATTGACTGTGTGCATTTTAGG | 56 |
| Right HA Edit PCR | F8_RightA_F | editing element | ATGAAGCTTGACGGTGGTTC | 57 |
|  | F8_RightA_R | 3' homology arm | TACGTAGATAAGTAGCATGGCG | 58 |
| Right HA Control PCR | F8_RightB_F | 3' homology arm | ATGATACCCATTTCCCTAGATTCC | 59 |
|  | F8_RightB_R | genomic sequence | GGCACCACTCCTGAAATACAC | 60 |

TABLE 4

Cycle parameters for ddPCR

| Cycling step | Temp, °C | Time (sec) | # of cycles |
|---|---|---|---|
| Enzyme activation | 94 | 60 | 1 |
| Denaturation | 94 | 15 | 25 |
| Annealing | 60 | 15 |  |
| Extension | 72 | 60 |  |

TABLE 4-continued

Cycle parameters for ddPCR

| Cycling step | Temp, °C. | Time (sec) | # of cycles |
|---|---|---|---|
| Enzyme deactivation | 72 | 60 | 1 |
| Hold(optional) | 4 | infinite | 1 |

Droplet Digital PCR (ddPCR)

Figure 5B:
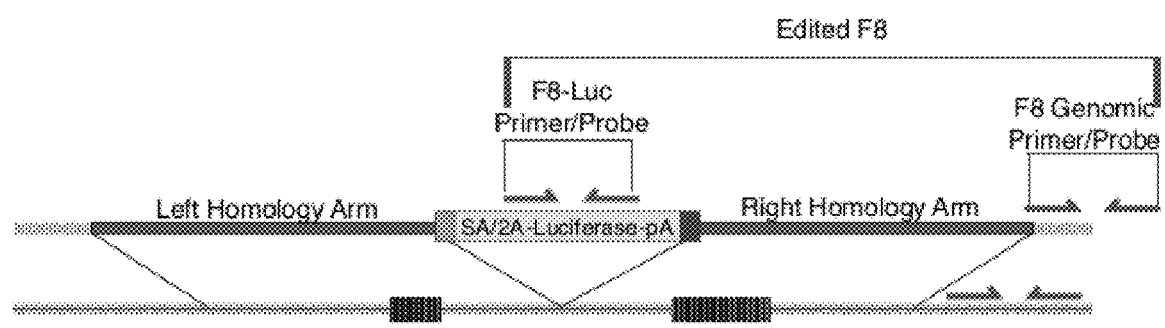
FIG. 5B illustrates the design of a droplet digital PCR (ddPCR) for detecting homologous recombination of the VG-mF8-001-Luc vector into the mouse genome.

Droplet digital PCR partitioned DNA samples into an oil emulsion in which end-point PCR reactions were run and quantified as a binary measurement of molecule density. This method allowed individual analysis of each genomic fragment and quantitation of edited and unedited DNA strands. The TaqMan® primers and probes used are shown in Table 5 below, and their targeting regions are shown in FIG. 5B. Briefly, the DNA samples were diluted in nuclease-free water to 10 ng/μl, and a mixture was made of 12 μl SuperMix no dUTP (BioRad), 0.6 μl of FAM probe (F8), 0.6 μl of VIC probe (SA2A), 4.8 μl of nuclease free water and 6 μl of diluted DNA (60 ng total). Droplets containing the sample mixture were generated using the QX200™ AutoDG™ Automated Droplet generator (BioRad), then transferred to a thermal cycler for PCR. The cycle parameters for the ddPCR are described in Table 6. After the PCR, the droplets were read on the QX200 droplet reader (Bio-Rad) and analyzed using the Quantasoft Software (BioRad). Edited DNA was recognized as a single DNA molecule that carried a payload (as detected by the SA2A assay) and a genomic DNA sequence outside of the homology arms (as detected by the F8 assay). Thus, editing frequencies were calculated based on the detected co-partitioning of the payload and the genomic DNA in a single droplet, in excess of the expected probability of co-partitioning of the payload and the genomic DNA from separate nucleic acid molecules.

Figure 5C:
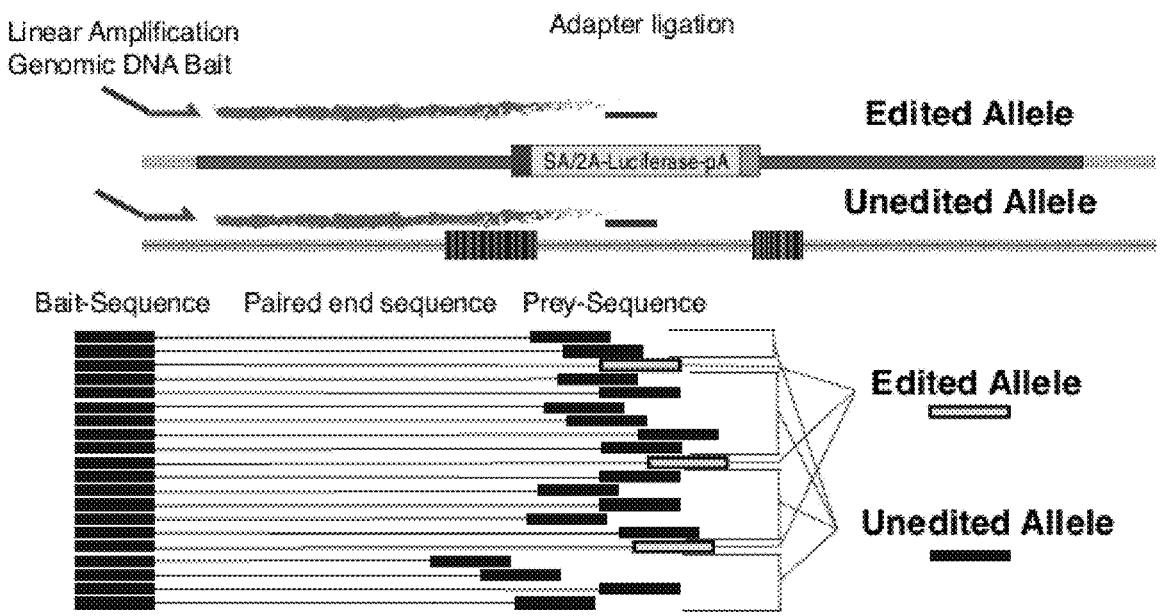
FIG. 5C illustrates the design of a quantitative next-generation sequencing method following linear amplification of the target locus.
Figure 5D:
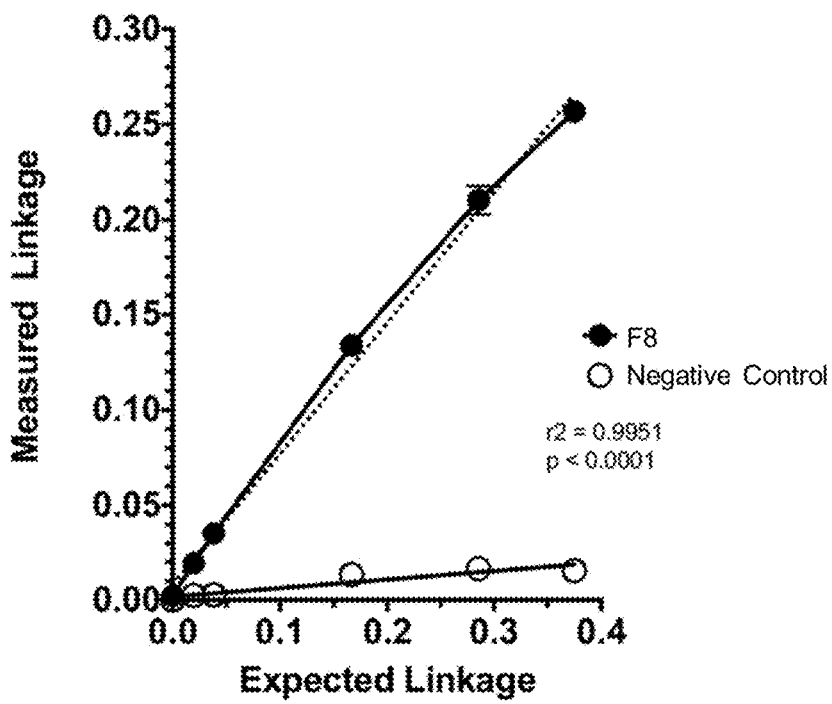
FIG. 5D is a plot showing the measured linkage against the expected linkage in cells transfected with the VG-mF8-001-Luc vector.

To determine if integration occurred at the expected location, genetic linkage was measured between the integrated sequence and the chromosome in which the sequence was integrated into. ddPCR was performed with probes targeting regions as shown in FIG. 5B. As shown in FIG. 5D, the measured linkage correlated well with expected linkage, indicating that integration occurred at the expected location.

Next Generation Sequencing (NGS)

Editing frequencies were also measured by a next generation sequencing assay. An exemplary method was described in Frock et al. (2015) *Nat Biotechnol* 33: 179-186. As shown in FIG. 5C, linear amplification using biotinylated bait primers targeting genomic regions outside of the homology arms were elongated toward the editing insertion site. The single stranded DNA products were purified by streptavidin isolation. Following ligation of NGS adapters and paired end sequencing, editing efficiency was determined as the ratio of reads that extend into the luciferase transgene relative to the unedited insertion site. To ensure accurate quantitation, these genotyping assays were tested against a standard control of artificially constructed editing control samples.

Results

Figure 6A:
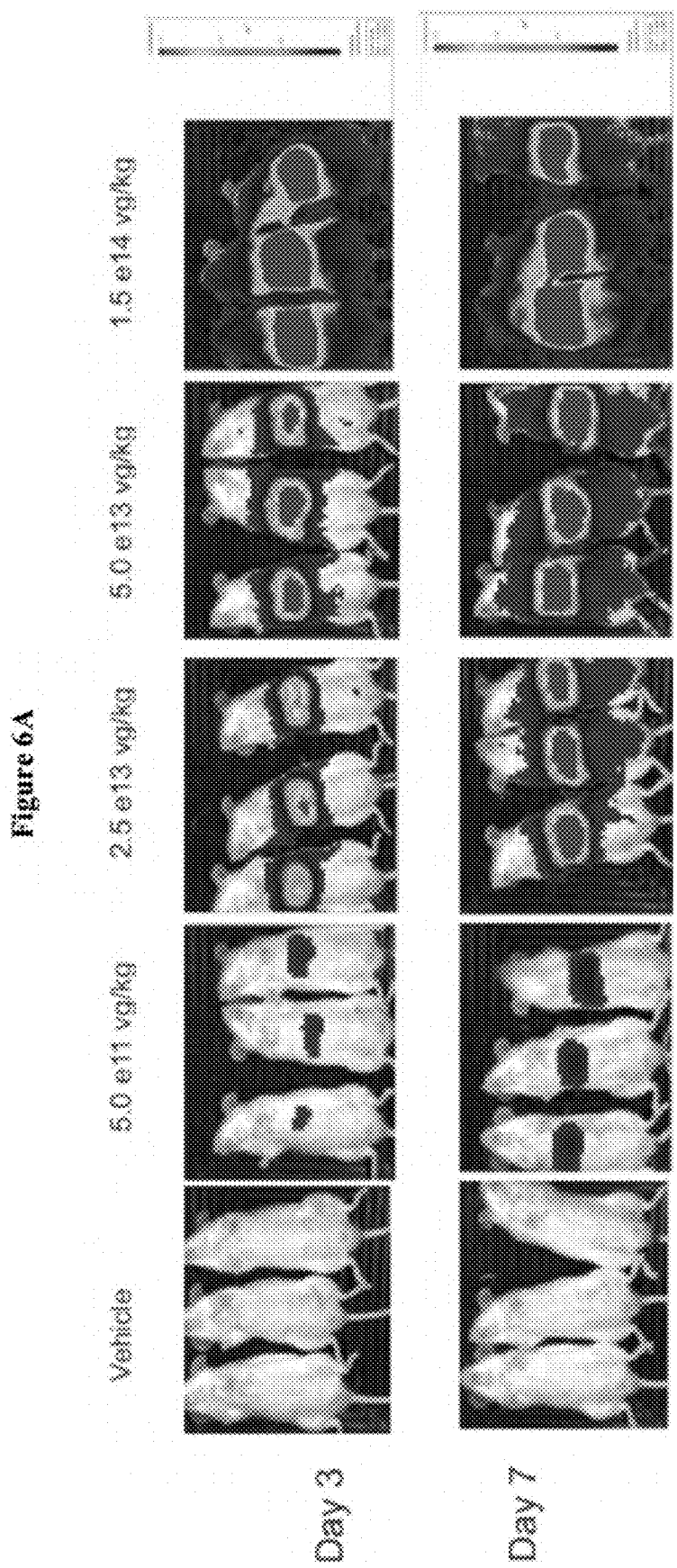
FIG. 6A is a set of photographs showing bioluminescence from mice after administration of the VG-mF8-001-Luc vector at the indicated doses.
Figure 6B:
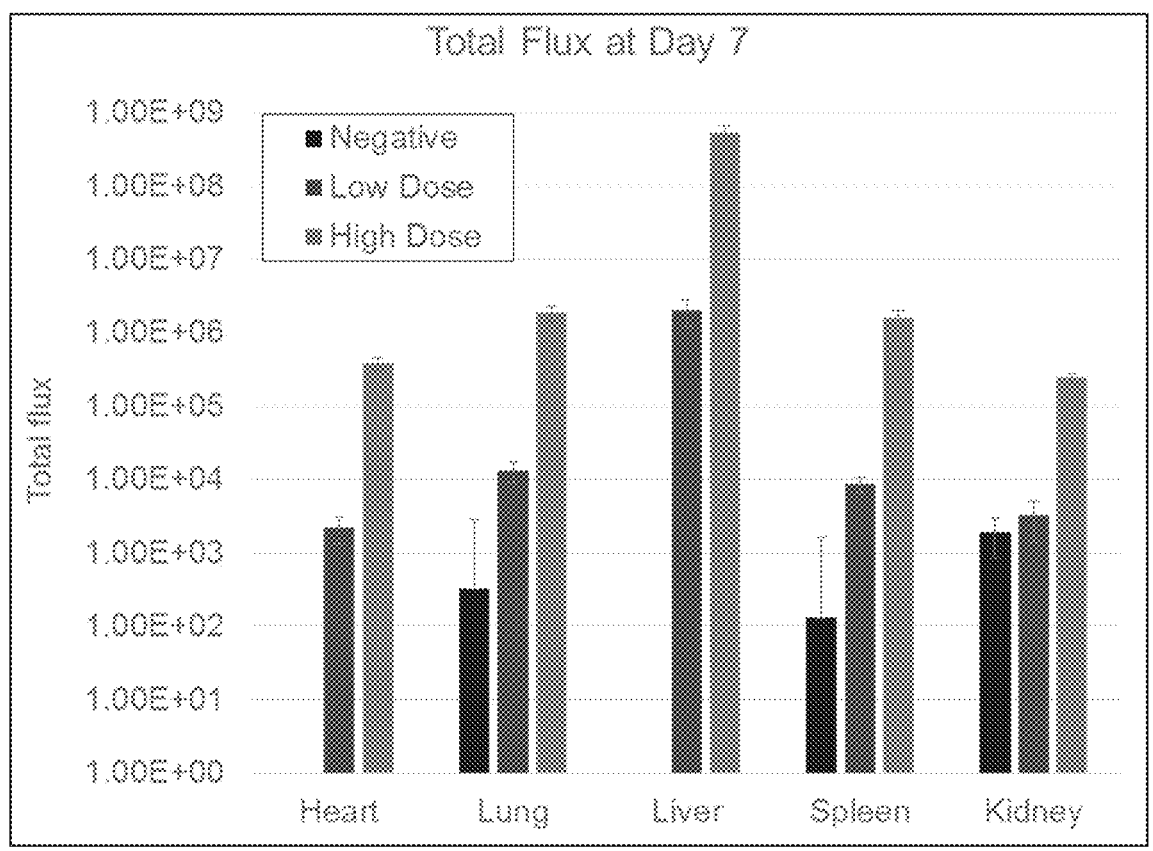
FIG. 6B is a graph showing the total flux of bioluminescence from the indicated organs obtained at day 7 from mice administered a low dose of $1 \times 10^{11}$ vector genomes or a high dose of $3 \times 10^{12}$ vector genomes of the VG-mF8-001-Luc vector.
Figure 6C:
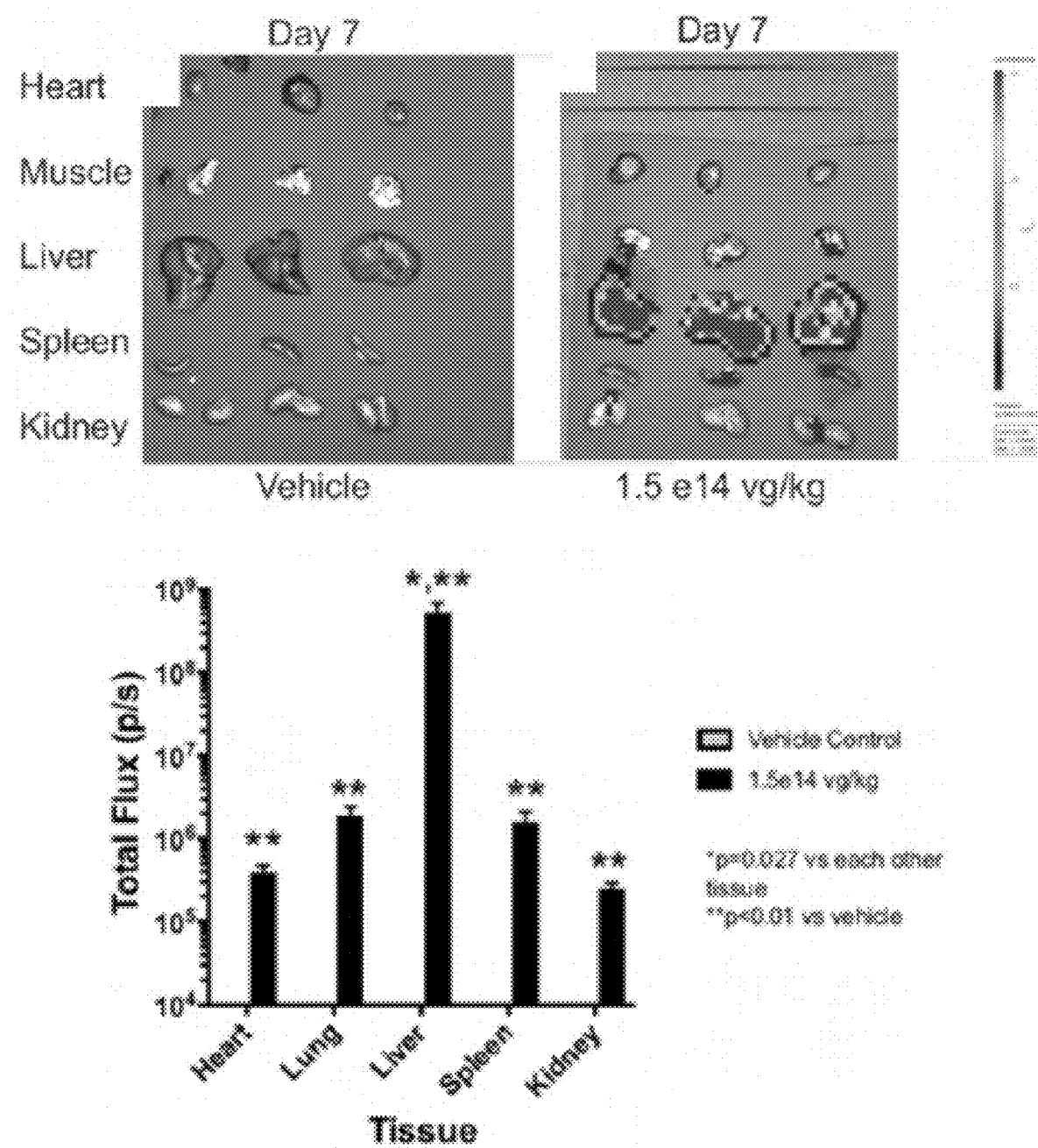
FIG. 6C is a set of photographs showing bioluminescence of the indicated organs obtained at day 7 from mice administered with the indicated dose of the VG-mF8-001-Luc vector. This figure also shows a graph of the total flux of luminiscence from the indicated organs. * indicates a significance level of p=0.27 as compared to each other organ; ** indicates a significance level of p<0.01 compared to vehicle control.
Figure 6D:
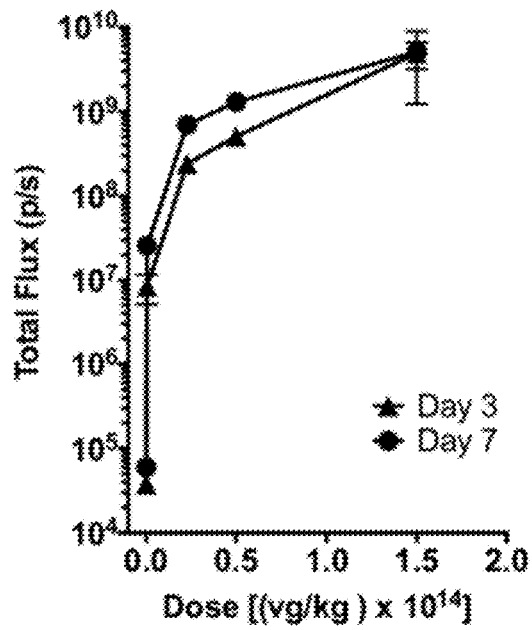
FIG. 6D is a graph showing the total flux of bioluminescence of day 3 and day 7 livers of mice administered the VG-mF8-001-Luc vector across the indicated doses.
Figure 6E:
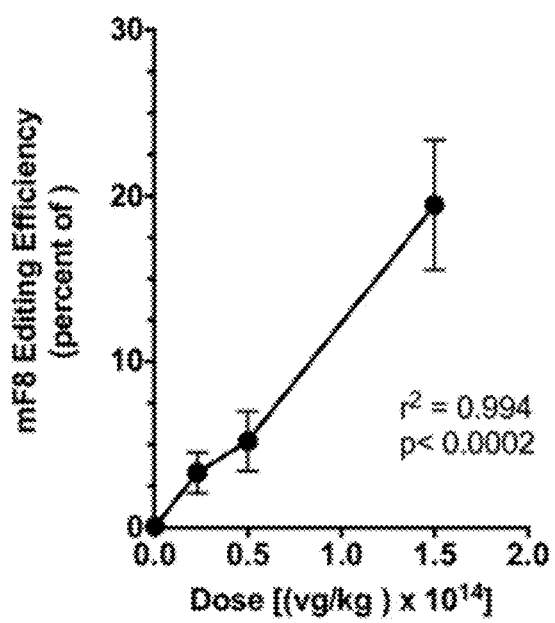
FIG. 6E is a graph showing editing efficiency of the VG-mF8-001-Luc vector in the liver across the indicated doses.
Figure 6F:
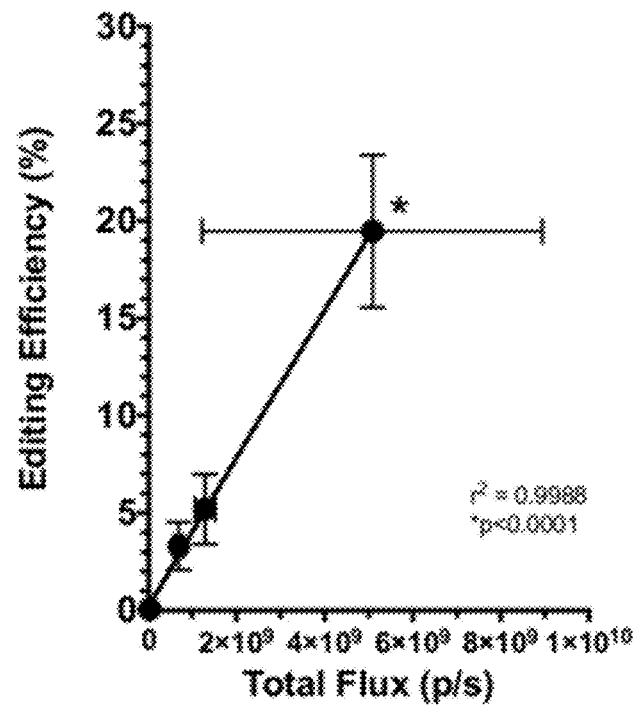
FIG. 6F is a graph showing the editing efficiency of the VG-mF8-001-Luc vector in mouse liver plotted against the total flux of bioluminescence in the liver. * indicates a significance level of p<0.0001.

As shown in FIGS. 6A, 6B, and 6C, 7 days after administration of the VG-mF8-001-Luc vector packaged in AAVHSC15, bioluminescence from integrated VG-mF8-001-Luc vector was detected primarily in the liver, but low levels were also observed in heart, lung, spleen, and kidney, in a dose-dependent manner. This result indicated that the editing of the F8 gene by intravenous administration of this vector occurred predominantly in the liver, but also could be detected at lower levels in other major organs. FIG. 6D shows the total flux of bioluminescence in livers of mice administered the VG-mF8-001-Luc vector packaged in AAVHSC15 at various doses, and indicates a dose-dependent response. FIG. 6D shows the editing efficiencies in the liver, as measured by ddPCR, after administration of various doses of the vector. FIG. 6F is a graph showing the editing efficiency of the VG-mF8-001-Luc vector in mouse liver plotted against the total flux of bioluminescence in the liver, and shows a string positive correlation between these two parameters. These data demonstrate that in vivo editing efficiency is dependent on dose of AAVHSC15-VG-mF8-001-Luc administered.

The ability of the AAV vector to edit F8 in vivo was also assessed in a long-term study. Briefly, the VG-mF8-001-Luc vector genome was packaged in AAVHSC15 or AAVHSC17 (see WO 2016/049230 A1). A dose of $5.8 \times 10^{12}$ vector genomes per kilogram of body weight was injected intravenously via tail vein to each NOD.CB17-Prkdc$^{scid}$/NCrCrl

TABLE 5

TaqMan ® primers and probes used for quantifying F8 edited DNA

| Assay ID | Assay name | Sequences | SEQ ID NO |
|---|---|---|---|
| mF8_gDNA2_Set1 | F8 | Probe: 5'-/56-FAM/AGTCCATCC/ZEN/ATGAGATGGAAACAAA/3IABkFQ/-3' | 47 |
| | | Primer 1: 5'-ACAAGCCAATTCTTGAAGTAACAG-3' | 48 |
| | | Primer 2: 5'-TCCTCTATATGATTTGAACTGTCTCC-3' | 49 |
| SA2A_Vector_Set2 | SA2A | Probe: 5'-/5HEX/TTCTAACAT/ZEN/GCGGTGACGTGGAGG/3IABkFQ/-3' | 50 |
| | | Primer 1: 5'-CCTAGGGCCGGGATTCT-3' | 51 |
| | | Primer 2: 5'-CCTCTTCTCTTCCTCCCACA-3' | 52 |

TABLE 6

Cycle parameters for ddPCR

| Cycling step | Temp, °C. | Time | ramp rate | # of cycles |
|---|---|---|---|---|
| Enzyme activation | 95 | 10 min | 2.5 C./sec | 1 |
| Denaturation | 95 | 30 sec | | 40 |
| Annealing/extension | 60 | 1 min | | 40 |
| Enzyme deactivation | 98 | 10 min | | 1 |
| Hold(optional) | 4 | infinite | | 1 |

(NOD/SCID) 6-8-week old male mouse. The mice were sacrificed 63 days after the vector injection, and liver samples were collected. Serial bioluminescent imaging of whole mice over time and editing efficiency measurement in the liver samples were performed using the same methods as described above.

Figure 7A:
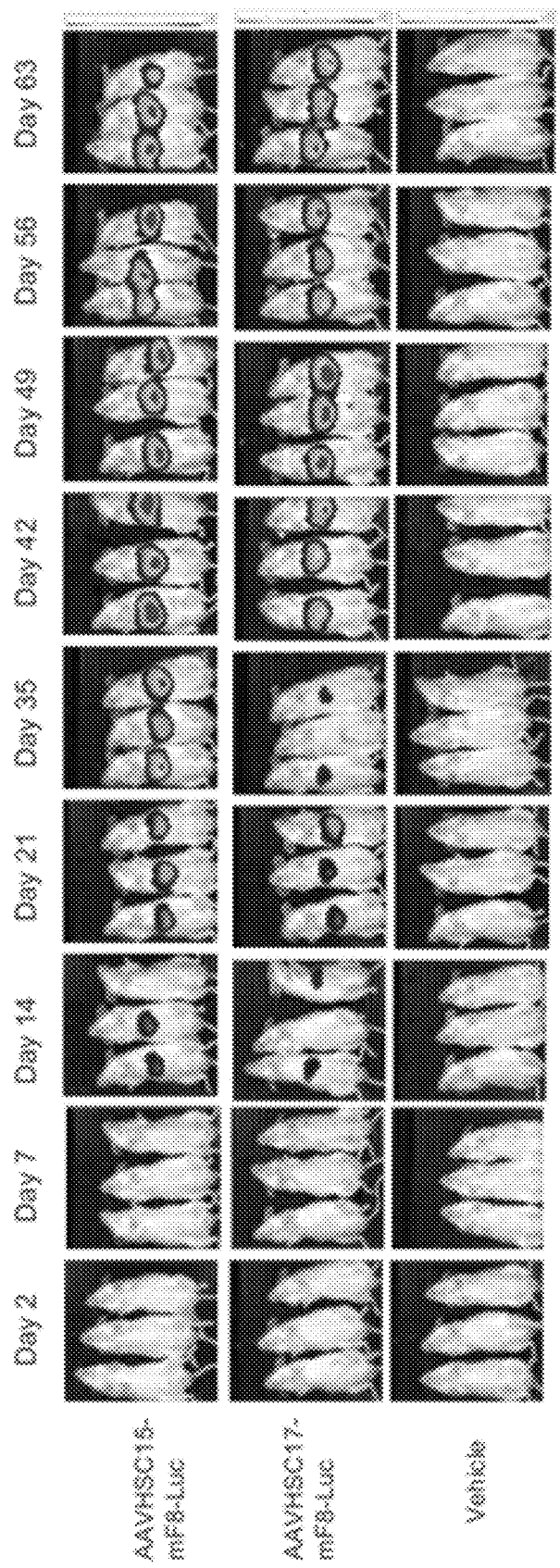
FIG. 7A is a set of photographs showing bioluminescence images from mice up to 63 days after administration of the VG-mF8-001-Luc vector packaged in AAVHSC15 or AAVHSC17 capsid.
Figure 7B:
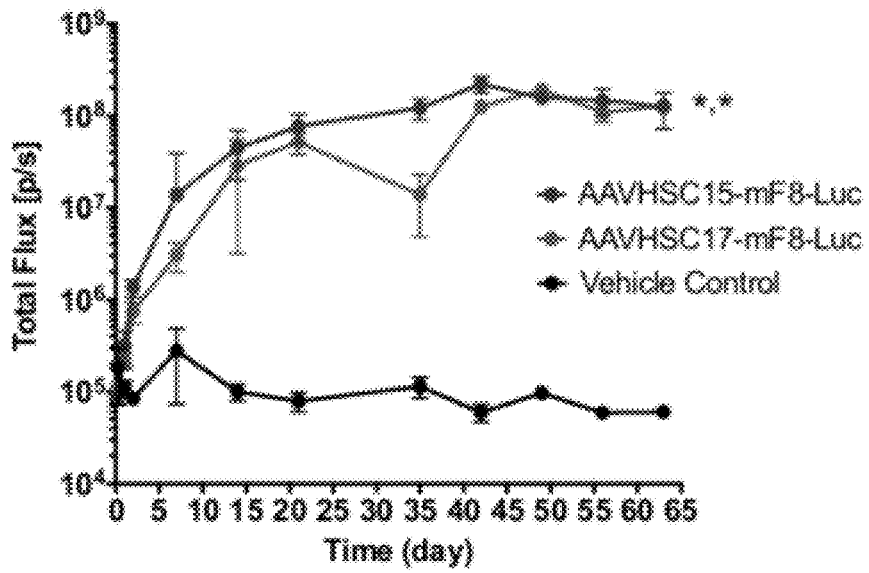
FIG. 7B is a graph showing the total flux of bioluminescence from these mice plotted against days post administration of vector (n=3 per treatment group). * indicates a significance level of p<0.004 compared to vehicle control.
Figure 7C:
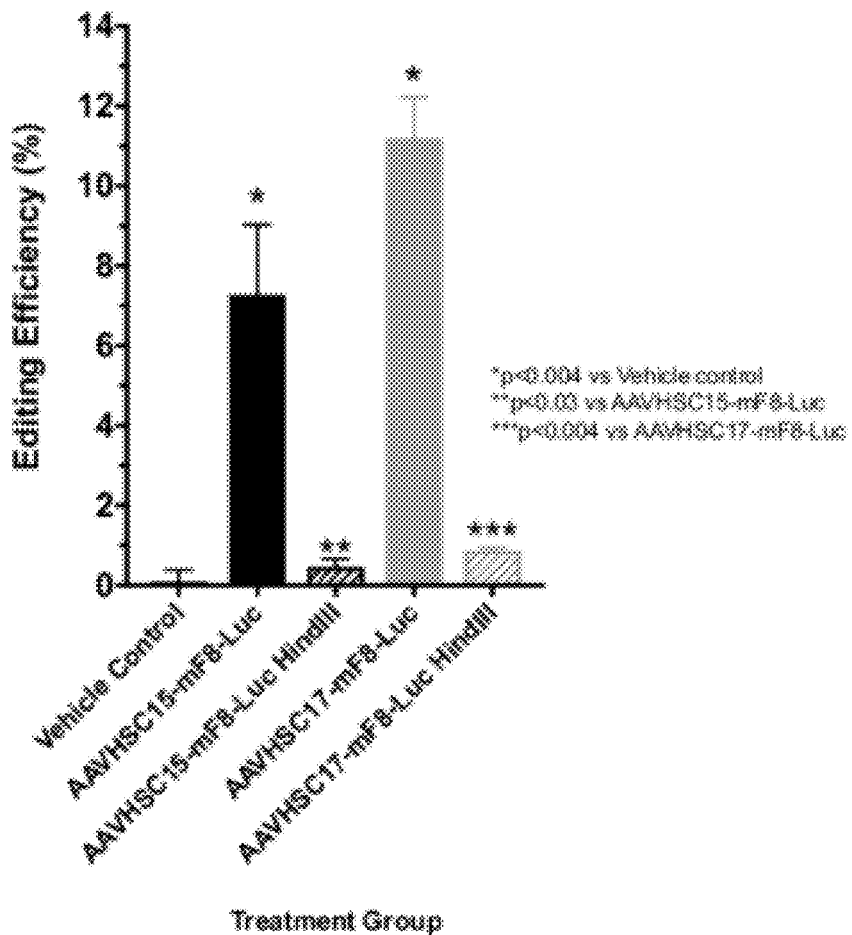
FIG. 7C is a graph showing the editing efficiency in cells obtained from mice administered the VG-mF8-001-Luc vector packaged in AAVHSC15 or AAVHSC17 capsids. Vectors indicated with "HindIII" refer to vectors that have been treated with the HindIII restriction enzyme; these vectors act as a negative control by artificially separating the inserted payload from the target genomic DNA. * indicates a significance level of p<0.004 compared to vehicle control;  indicates a significance level of p<0.03 compared to the VG-mF8-001-Luc vector packaged in AAVHSC15 capsids (AAVHSC15-mF8-Luc); * indicates a significance level of p<0.004 compared to the VG-mF8-001-Luc vector packaged in AAVHSC17 capsids (AAVHSC17-mF8-Luc).
Figure 7E:
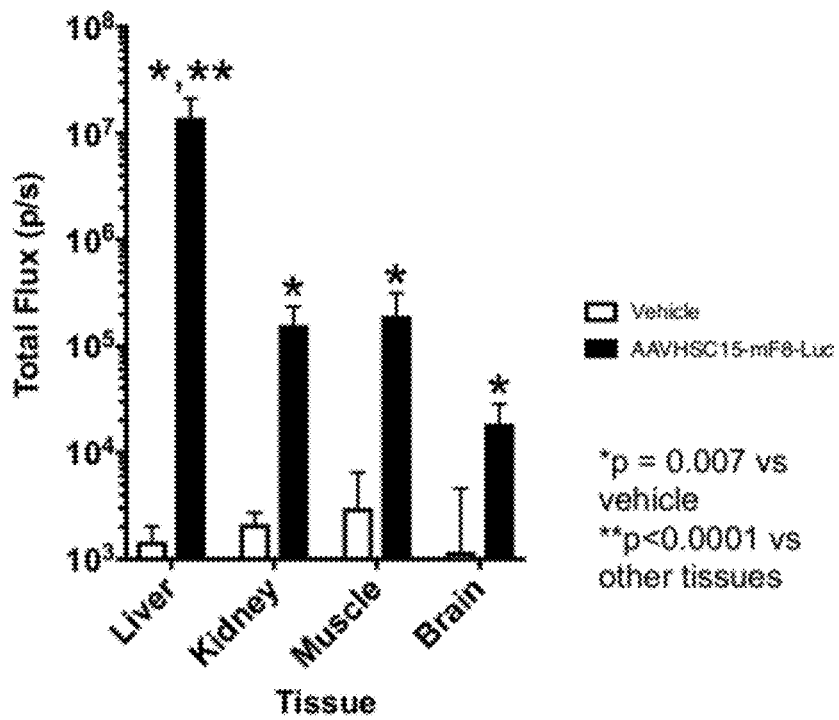
FIG. 7E is a graph showing the total flux of bioluminescence of the liver, kidney, muscle, and brain tissues of mice administered the VG-mF8-001-Luc vector packaged in AAVHSC15 capsids. * indicates a significance level of p=0.007 compared to vehicle control; ** indicates a significance level of p<0.0001 compared to other tissues.
Figure 7F:
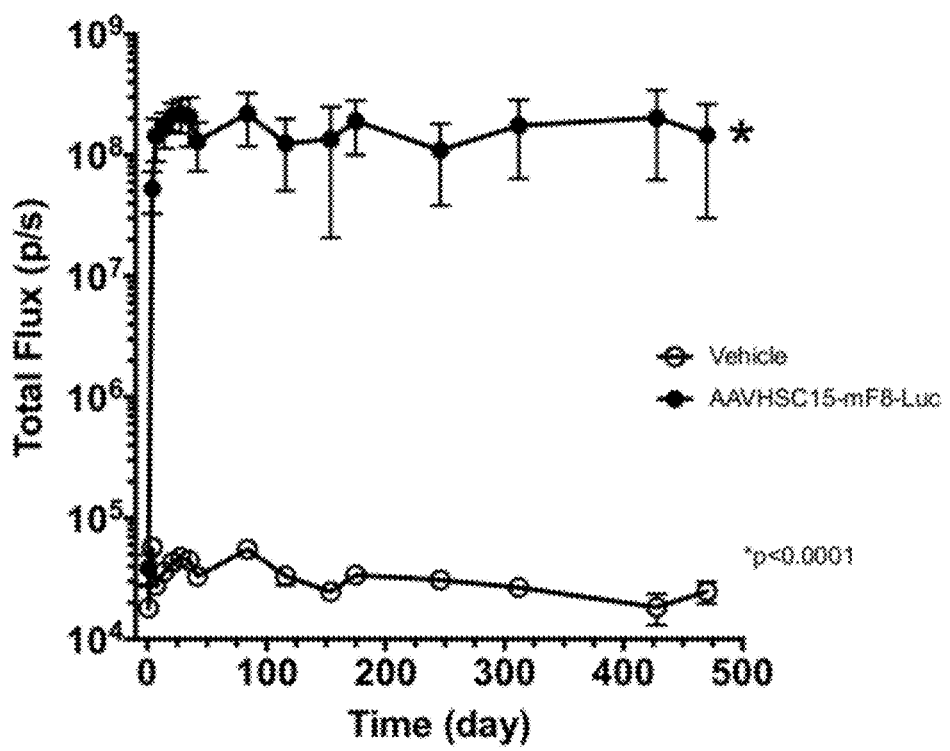
FIG. 7F is a graph showing the total flux of bioluminescence in mice administered the VG-mF8-001-Luc vector packaged in AAVHSC15 capsids up to 470 days after administration. * indicates a significance level of p<0.0001 compared to vehicle control.

Luminescence from integrated VG-mF8-001-Luc vector was initially detectable within 24 hours after the administration of the vector packaged in either AAVHSC15 or AAVHSC17, and reached a plateau approximately 40 days after the administration (FIG. 7B). The bioluminescence levels remained high 63 days after the administration (FIG. 7A). FIG. 7C shows the editing efficiency measured in cells obtained from mice administered the VG-mF8-001-Luc vector packaged in AAVHSC15 or AAVHSC17 capsids. Vectors indicated with "HindIII" refer to vectors that have been treated with the HindIII restriction enzyme; these vectors act as a negative control by artificially separating the inserted payload from the target genomic DNA. Bioluminescence was observed in the liver samples of the mice 7 days post injection of the vector packaged in the AAVHSC15 vector (FIG. 7D). As shown in FIG. 7E, bioluminescence was detected at significantly higher levels in the liver as compared to tissues of other major organs. FIG. 7F shows that the bioluminescence in normal mice administered the VG-mF8-001-Luc vector packaged in AAVHSC15 capsids is detected for at least 470 days. Taken together, these data indicate that intravenous delivery of the VG-mF8-001-Luc vector packaged in AAVHSC15 or AAVHSC17 capsids result in durable editing of the F8 locus in mice.

Figure 10A:
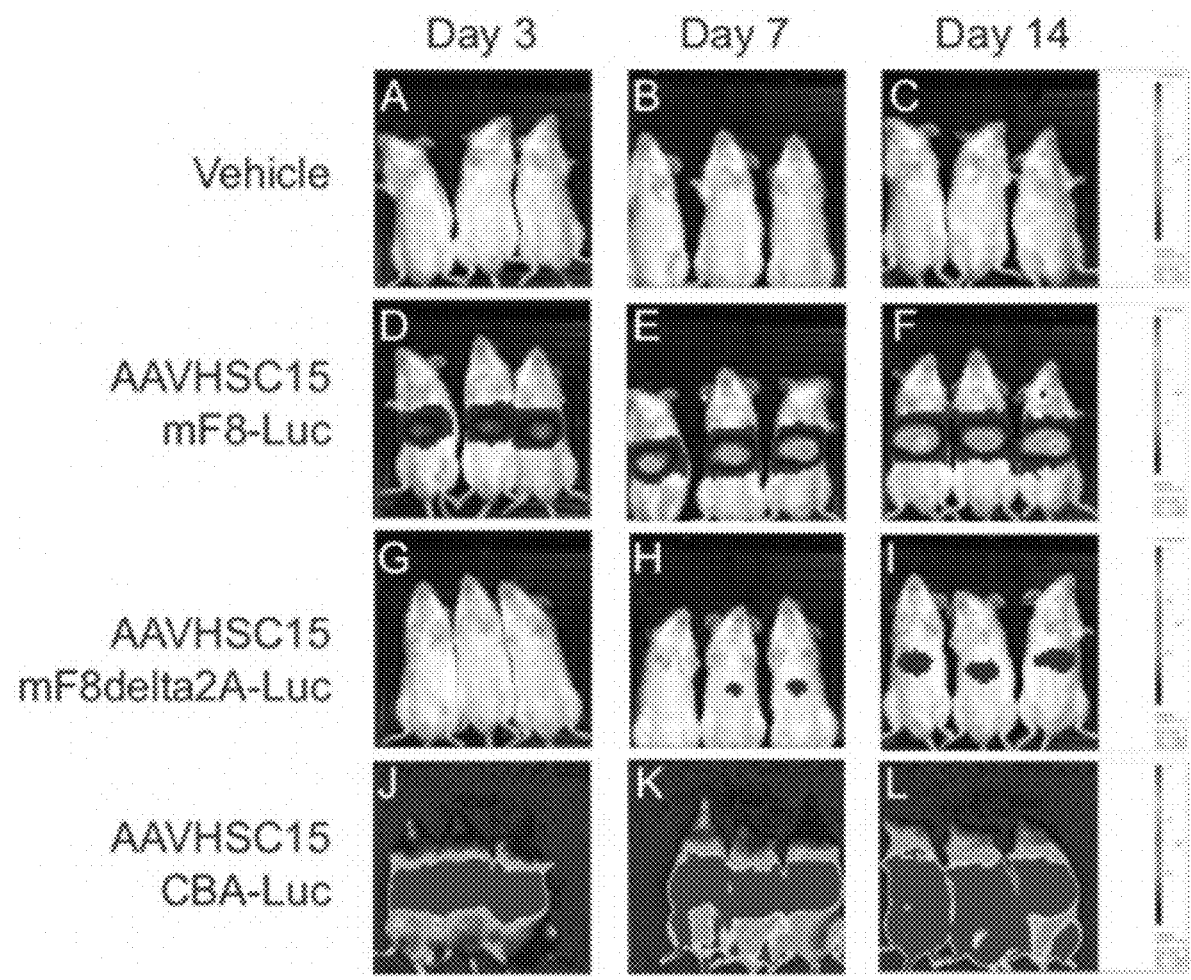
FIG. 10A is a set of photographs of day 3, day 7, and day 14 mice administered the indicated vectors. As positive control, a vector comprising a luciferase encoding sequence driven by a chicken β-actin (CBA) promoter was used.
Figure 10B:
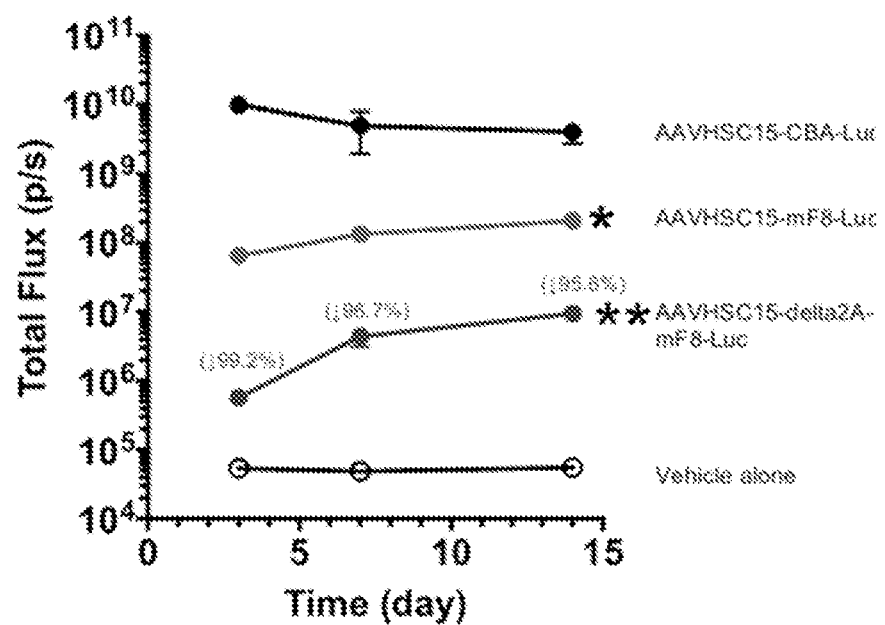
FIG. 10B is a graph showing the total flux of bioluminescence in mice administered the indicated vectors. * indicates a significance level of p<0.0001 compared to mice administered the mF8delta2A-luc vector; ** indicates a significance level of p<0.0001 compared to vehicle control.
Figure 10D:
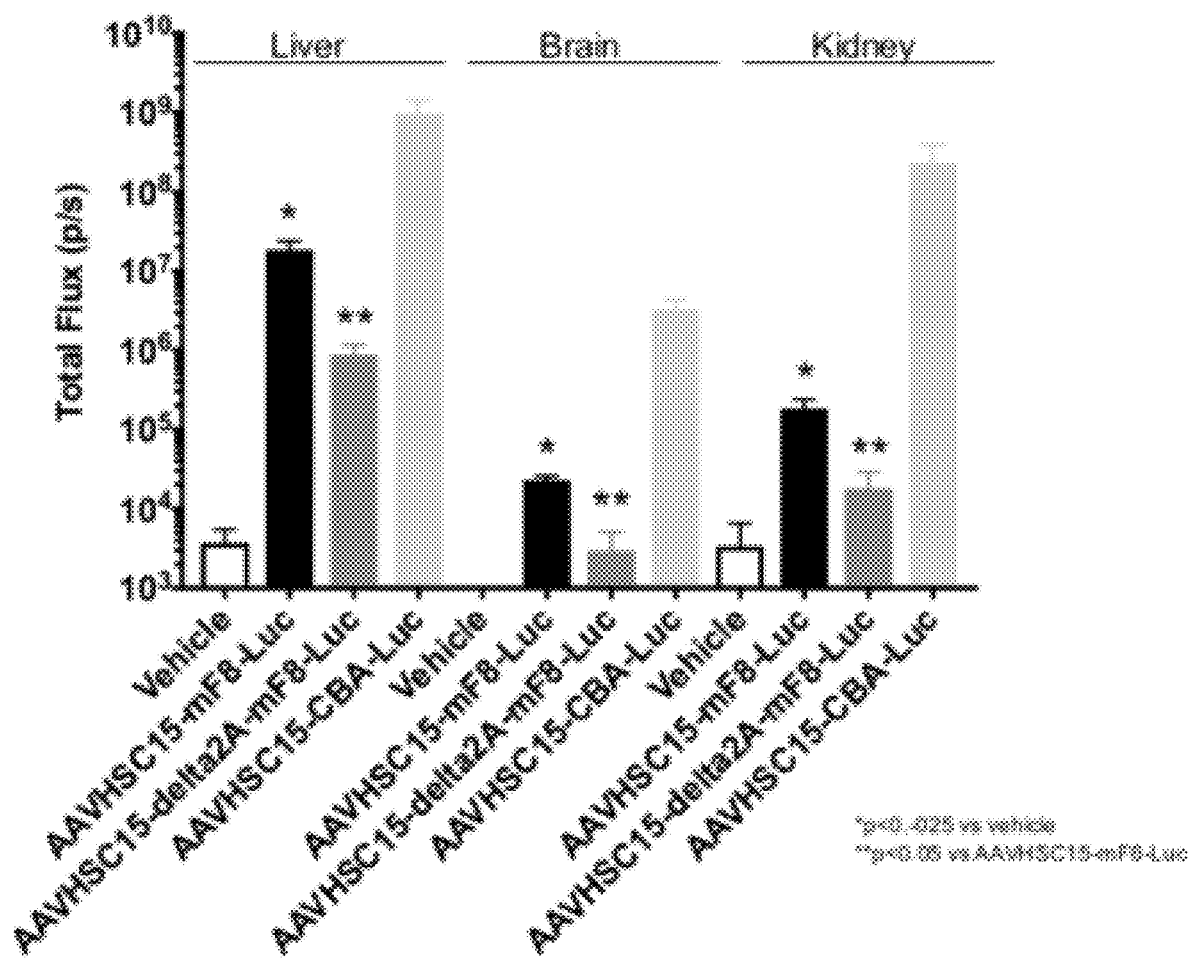
FIG. 10D is a graph showing the total flux of bioluminescence in each of these tissues obtained from mice administered the indicated vectors.
Figure 10E:
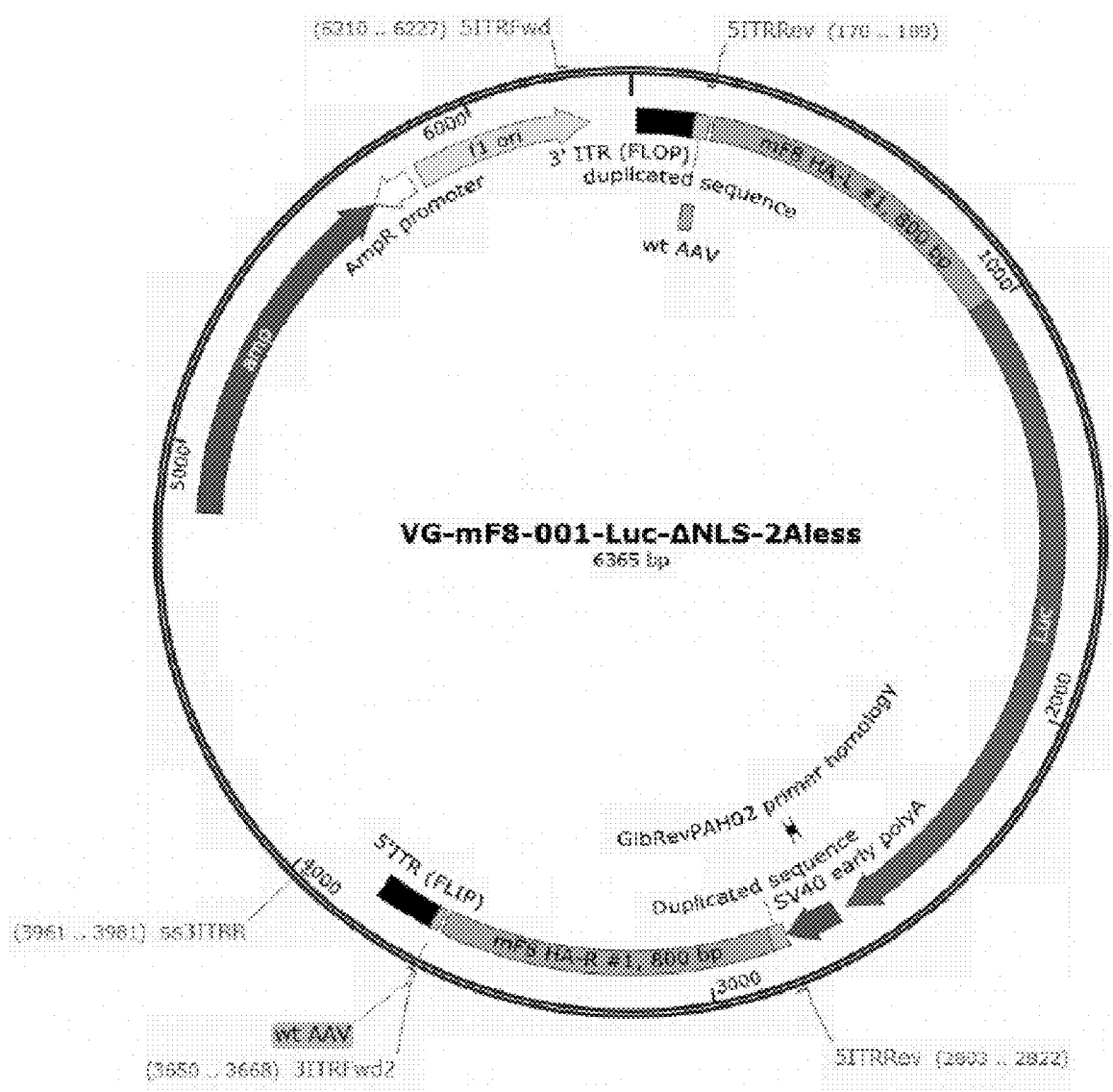
FIG. 10E is a map of the mF8delta2A-luc vector.

In contrast, removal of the splice acceptor from the VG-mF8-001-Luc vector greatly reduced luciferase expression in mice. See FIG. 10E for a map of the mF8delta2A-luc vector. Mice administered the mF8delta2A-luc vector packaged in AAVHSC15 capsids showed greatly reduced bioluminescence compared to the intact vector (FIG. 10A). When quantified, it was determined that mice administered the mF8delta2A-luc vector exhibited in a 96% loss of observable bioluminescence relative to the intact vector (FIG. 10B). As shown in FIG. 10C, bioluminescence was greatly reduced in the livers of mice administered the mF8delta2A-luc vector packaged in AAVHSC15 capsids compared to the intact vector. Reduction in bioluminescence was also observed in brain and kidney tissues (FIG. 10D).

Figure 8A:
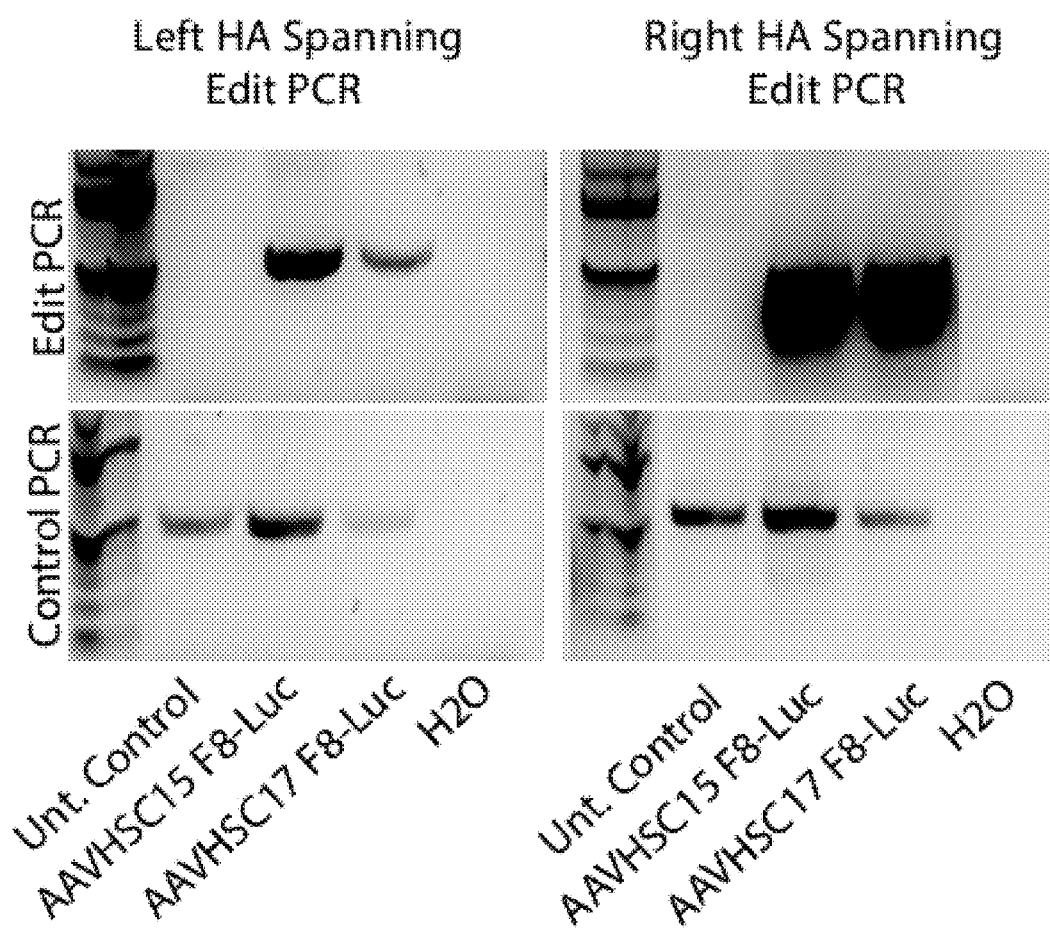
FIG. 8A is a set of gel electrophoresis graphs showing the PCR products amplified from liver samples of mice injected with the VG-mF8-001-Luc vector packaged in AAVHSC15 and AAVHSC17 capsids.
Figure 8B:
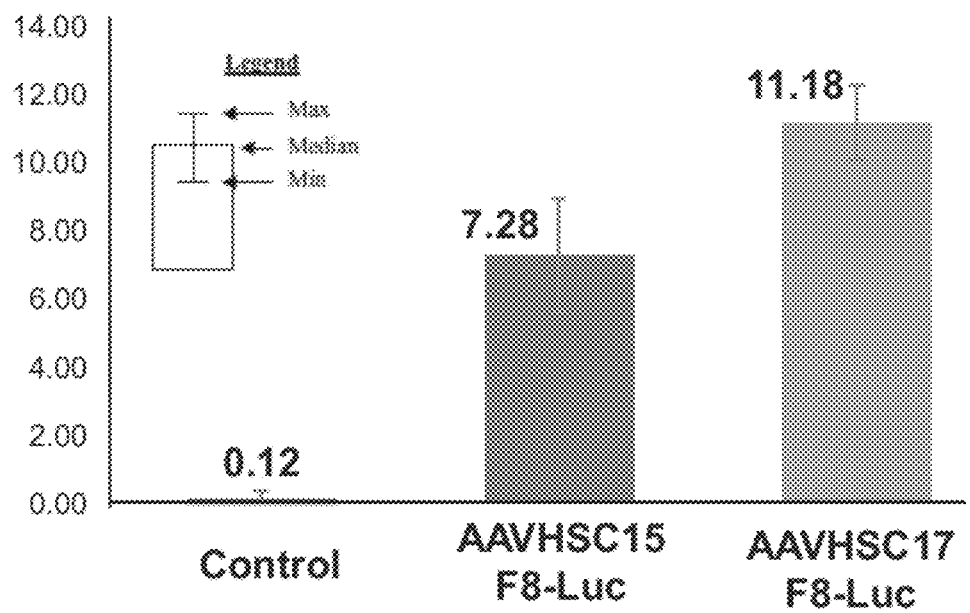
FIG. 8B is a graph showing the editing efficiency in the liver of these mice as measured by ddPCR.
Figure 8C:
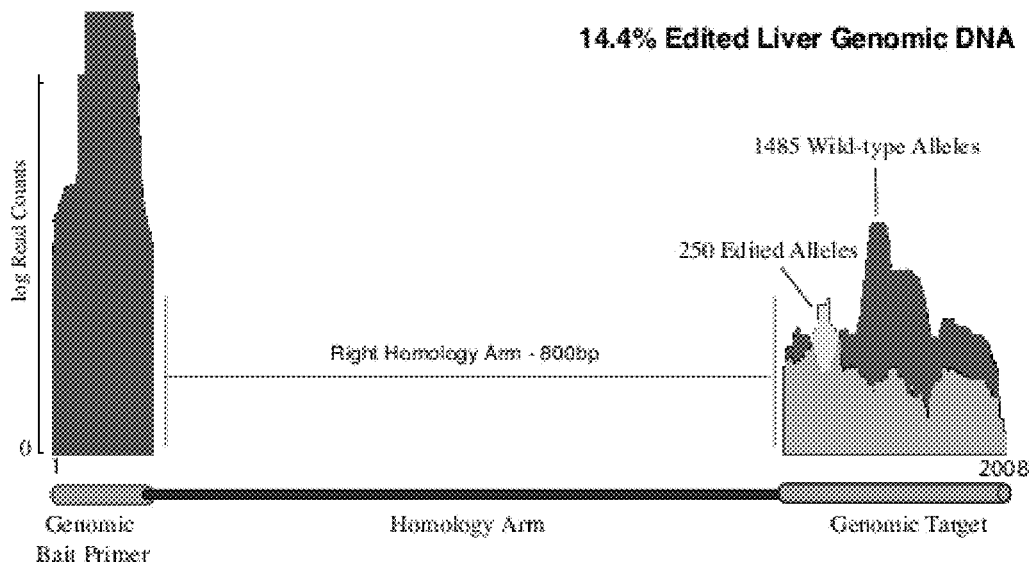
FIG. 8C is a graph showing the analysis of the next-generation sequencing results of the target locus in liver samples of mice injected with the VG-mF8-001-Luc vector packaged in AAVHSC15 capsid.
Figure 9A:
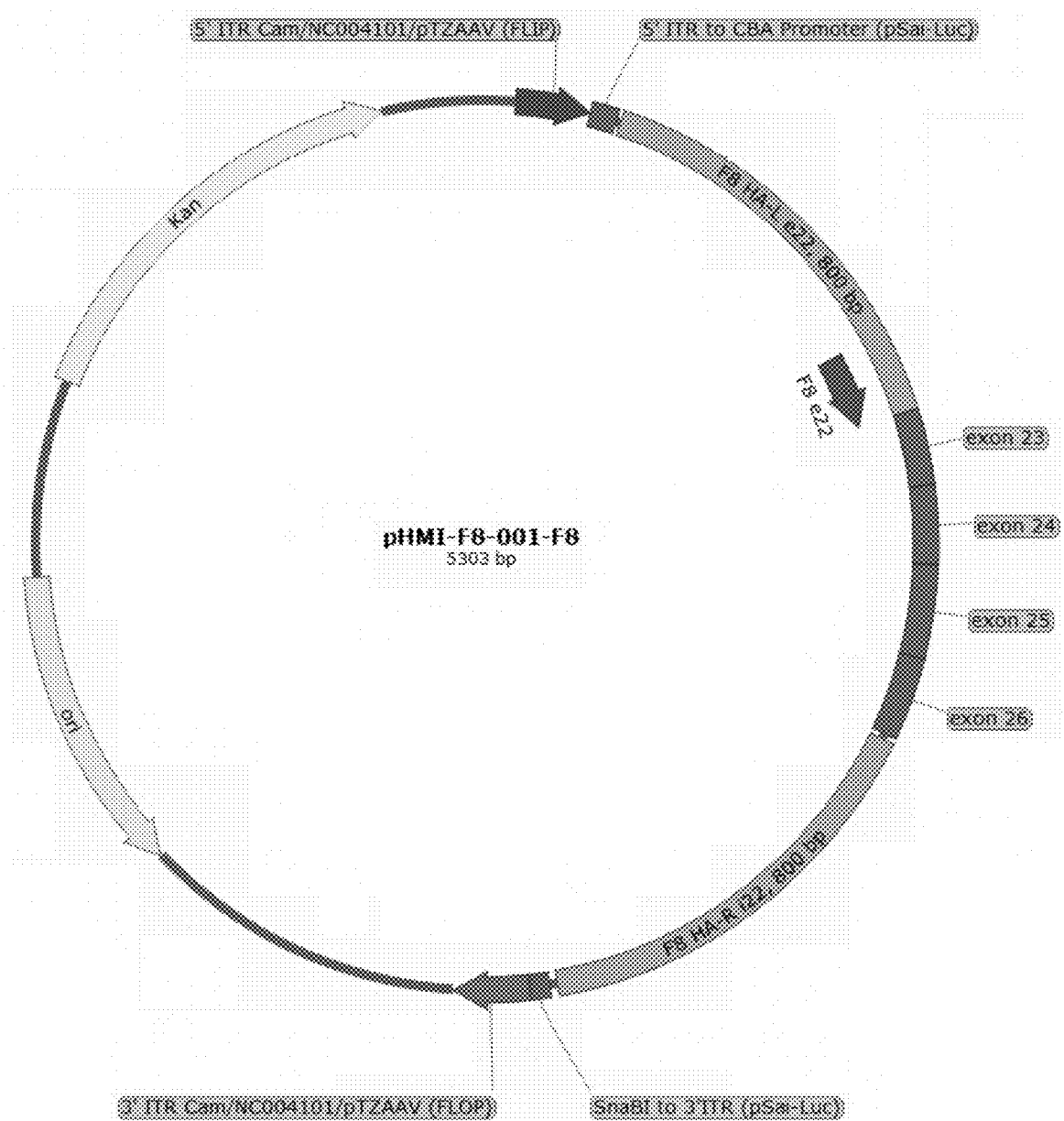
FIGS. 9A, 9B, 9C, and 9D are maps of the pHMI-F8-001-F8, pHMI-F8-002-F8, pHMI-F8-003-F8, and pHMI-F8-004-F8 vectors, respectivley.
Figure 9B:
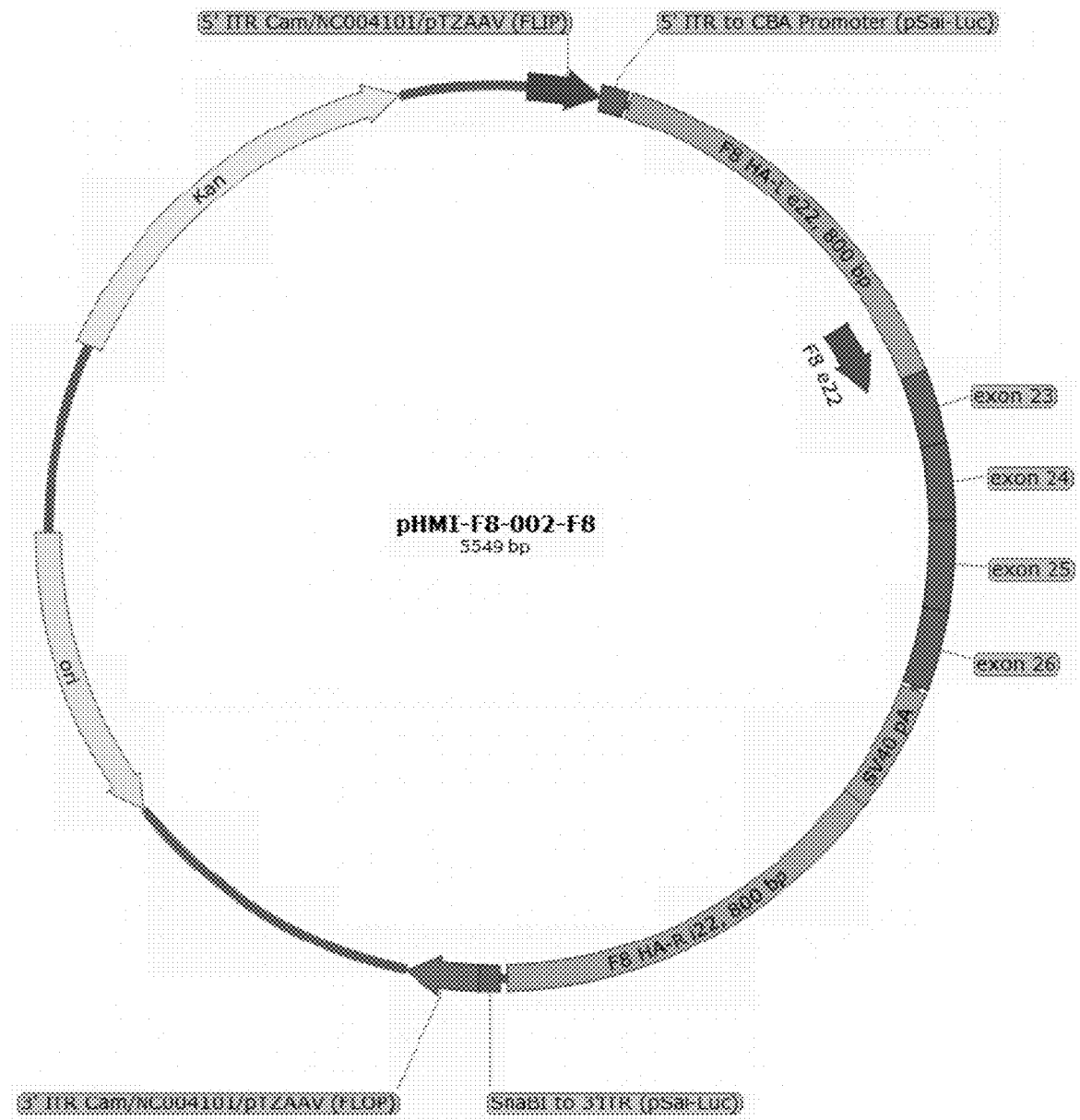
Figure 9C:
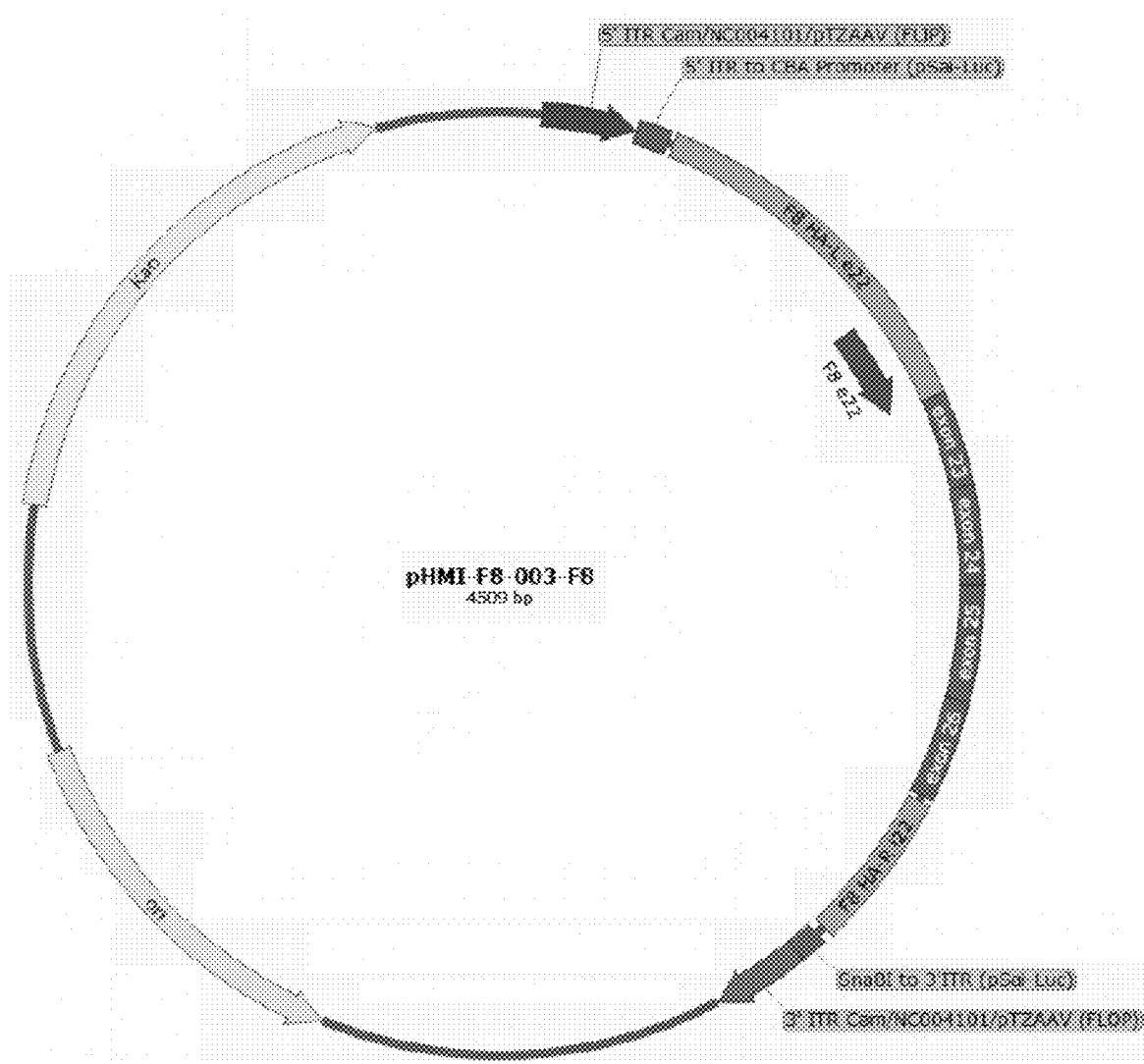
Figure 9D:
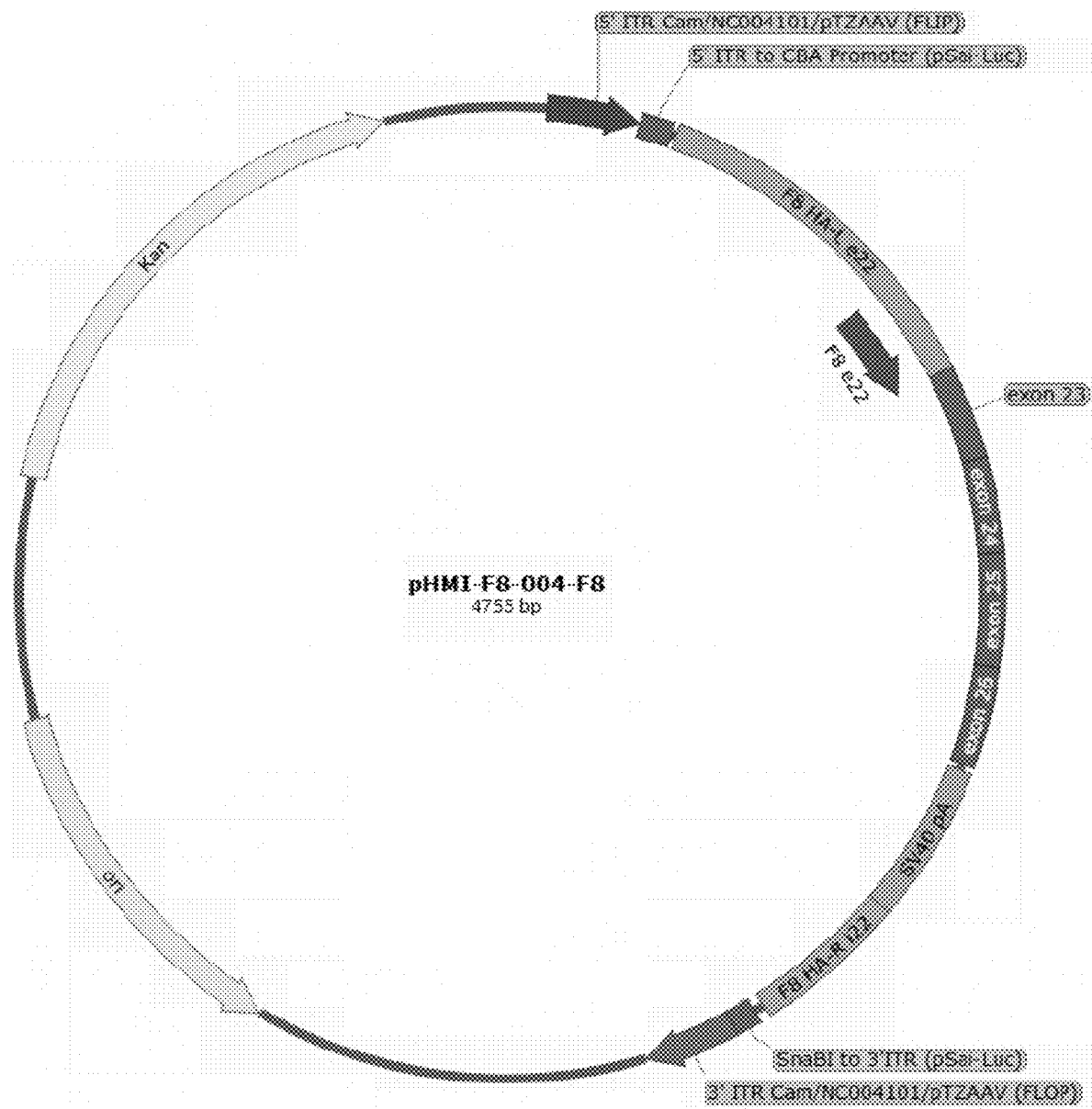

To detect editing of the F8 gene, DNA samples from the mouse liver 9 weeks post administration of the VG-mF8-001-Luc vector were analyzed by end-point PCR, droplet digital PCR, and next generation sequencing as described above. As shown in FIG. 8A, editing-specific PCR products were detected in liver samples of the mice injected with the VG-mF8-001-Luc vector packaged in AAVHSC15 and AAVHSC17. Editing efficiencies in the liver, as measured by ddPCR, were approximately 7% and 11% in the mice that received injections of the vector packaged in AAVHSC15 and AAVHSC17, respectively (FIG. 8B). Next generation sequencing detected a similar editing efficiency of 14.4% in liver samples of the mice injected with the VG-mF8-001-Luc vector packaged in AAVHSC15 (FIG. 8C).

The results above suggest that intravenous administration of an F8 correction vector may alter (e.g., restore) the expression of F8 from a liver cell with high efficiency.

FIG. 7C is a graph showing the editing efficiency in cells obtained from mice administered the VG-mF8-001-Luc vector packaged in AAVHSC15 or AAVHSC17 capsids. * indicates a significance level of p<0.004 compared to vehicle control. Vectors indicated with "HindIII" refer to vectors that have been treated with the HindIII restriction enzyme; these vectors act as a negative control by artificially separating the inserted payload from the target genomic DNA.  indicates a significance level of p<0.03 compared to the VG-mF8-001-Luc vector packaged in AAVHSC15 capsids (AAVHSC15-mF8-Luc); * indicates a significance level of p<0.004 compared to the VG-mF8-001-Luc vector packaged in AAVHSC17 capsids (AAVHSC17-mF8-Luc). FIG. 7D is a set of photographs showing bioluminescence images of the liver, kidney, muscle, and brain tissues (from left to right in each photograph) of mice at various time points post administration of the VG-mF8-001-Luc vector packaged in AAVHSC15 capsid (AAVHSC15-mF8-Luc). The various time points increase from left to right in the top row and continue from left to right in the bottom row of photographs. FIG. 7E is a graph showing the total flux of bioluminescence of the liver, kidney, muscle, and brain tissues of mice administered the VG-mF8-001-Luc vector packaged in AAVHSC15 capsids. * indicates a significance level of p=0.007 compared to vehicle control; ** indicates a significance level of p<0.0001 compared to other tissues. FIG. 7F is a graph showing the total flux of bioluminescence in mice administered the VG-mF8-001-Luc vector packaged in AAVHSC15 capsids up to 470 days after administration. * indicates a significance level of p<0.0001 compared to vehicle control.

Example 4: F8 Correction Vectors for Insertion of an F8 Coding Sequence into the F8 Gene This example provides F8 correction vectors pHMI-F8-001-F8, pHMI-F8-002-F8, pHMI-F8-003-F8, and pHMI-F8-004-F8, each containing an F8 coding sequence for insertion after the last nucleotide of exon 22 of the human F8 gene. These vectors are capable of restoring the expression of F8 from a mutant F8 gene locus having an intron 22 inversion.

The vector maps of pHMI-F8-001-F8, pHMI-F8-002-F8, pHMI-F8-003-F8, and pHMI-F8-004-F8 are shown in FIGS. 9A, 9B, 9C, and 9D, respectively. Each of these vectors comprises the following elements 5' to 3': a 5' ITR ("5' ITR Cam/NC004101/pTZAAV (FLIP)"); a 5' homology arm ("F8 HA-L e22, 800 bp" or "F8 HA-L e22"); the coding sequence of exons 23-26 of human F8 ("exon 23," "exon 24," "exon 25," and "exon 26"); an optional SV40 polyadenylation sequence ("SV40 pA" in pHMI-F8-002-F8 and pHMI-F8-004-F8 only); a 3' homology arm ("F8 HA-R i22, 800 bp" or "F8 HA-R i22"); and a 3' ITR ("3' ITR Cam/NC004101/pTZAAV (FLOP)"). The sequences of these elements are set forth in Table 7. A targeted integration restriction cassette ("TI RE cassette") comprising recognition and cleavage sites for unique restriction endonucleases may be inserted downstream from the polyadenylation sequence, facilitating detection of the desired homologous recombination.

TABLE 7

| | SEQ ID NO | | | |
|---|---|---|---|---|
| Genetic Element | pHMI-F8-001-F8 | pHMI-F8-002-F8 | pHMI-F8-003-F8 | pHMI-F8-004-F8 |
| 5' ITR element | 18 | 18 | 18 | 18 |
| 5' homology arm | 27 | 27 | 31 | 31 |
| partial coding sequence of human F8 (exons 22-26) | 26 | 26 | 26 | 26 |
| SV40 polyadenylation sequence | N/A | 37 | N/A | 37 |
| 3' homology arm | 28 | 28 | 32 | 32 |
| 3' ITR element | 19 | 19 | 19 | 19 |
| coding sequence cassette (including partial F8 coding sequence and SV40 polyadenylation sequence) | N/A | 33 | N/A | 33 |
| correction genome (from 5' homology arm to 3' homology arm) | 38 | 39 | 40 | 41 |
| correction genome (from 5' ITR to 3' ITR) | 42 | 43 | 44 | 45 |

The 5' homology arm comprises the wild-type genomic sequence upstream of the insertion site, wherein the insertion site is the internucleotide bond between exon 22 and intron 22 of the F8 gene. The 3' homology arm comprises the wild-type genomic sequence downstream from the insertion site. Integration of the pHMI-F8-001-F8, pHMI-F8-002-F8, pHMI-F8-003-F8, or pHMI-F8-004-F8 vector into the human genome allows transcription of the F8 locus into a pre-mRNA comprising 5' to 3' the following elements: a portion of the F8 pre-mRNA from the endogenous 5' end to the insertion site, and the partial F8 coding sequence (exons 22-26, excluding polyadenylation sequence). Splicing of this pre-mRNA generates an mRNA comprising 5' to 3' the following elements: exon 1, intron 1, exon 2, intron 2, exon 3, intron 3, exon 4, intron 4, exon 5, intron 5, exon 6, intron 6, exon 7, intron 7, exon 8, intron 8, exon 9, intron 9, exon 10, intron 10, exon 11, intron 11, exon 12, intron 12, exon 13, intron 13, exon 14, intron 14, exon 15, intron 15, exon 16, intron 16, exon 17, intron 17, exon 18, intron 18, exon 19, intron 19, exon 20, intron 20, exon 21, intron 21, exon 22, exon 23, exon 24, exon 25, and exon 26. An endogenous polyadenylation sequence is present downstream from the mutant F8 gene having an intron 22 inversion. Thus, transcription of the edited F8 gene will be properly terminated though the pHMI-F8-001-F8 and pHMI-F8-003-F8 vectors do not comprise a polyadenylation sequence. An SV40 polyadenylation sequence is added in the pHMI-F8-002-F8 and pHMI-F8-004-F8 vectors to ensure efficient transcription termination. Integration of any one of these vectors into the human genome inserts the coding sequence of exons 23-26 of human F8, thereby restoring the expression of a wild-type F8 protein that has been impaired by mutations (e.g., intron 22 inversion) downstream from exon 22 of the F8 gene.

The vectors are packaged with a clade F AAV capsid (e.g., AAVHSC7, AAVHSC15, and AAVHSC17). The packaged virus is examined in vitro for assessment of targeted integration. B lymphoblastoid cells are cultured in RPMI-1640 medium supplemented with 15% fetal calf serum (FCS) and 2 mM L-glutamine. Cells are seeded at approximately 200,000 cells per mL and split when cells reach approximately 500,000 to 1,000,000 cells per mL. Cells are in log phase growth on the day of transduction. Cells are counted and an appropriate number of cells are plated. Typically, 10,000 cells are plated for flow cytometry analysis. Vectors are thawed on ice and sonicated on ice if necessary prior to transductions. Virus is added to each well individually and media is pipetted up and down to evenly distribute virus. Vector does not exceed 10% of the culture volume. Vector is calculated based on the titer and MOI and is calculated before plating to ensure proper plates are used.

Forty-eight hours after transduction, cells transduced with the vector are harvested using FACS Buffer (1×PBS, 2% FCS, 0.1% sodium azide). Cells are spun down at 1200 RPM for 10 minutes. FACS buffer is removed so that approximately 200 µL remains. DAPI (100 µM working stock) is added immediately before flow cytometry analysis to a final concentration of 3 µM.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

We claim:

1. A replication-defective adeno-associated virus (AAV) comprising:
   a) an AAV capsid comprising an AAV Clade F capsid protein; and
   b) a correction genome comprising from 5' to 3':
      (i) a 5' AAV ITR nucleotide sequence;
      (ii) a 5' homology arm nucleotide sequence of up to 2000 nucleotides in length, comprising a nucleotide sequence that is at least 99% identical to SEQ ID NO: 27;
      (iii) an editing element for editing a target locus in the F8 gene, comprising an F8 nucleotide sequence that encodes an amino acid sequence consisting of the amino acid sequence encoded by SEQ ID NO: 26 operably linked to a polyadenylation sequence;
      (iv) a 3' homology arm nucleotide sequence of up to 2000 nucleotides in length, comprising a nucleotide sequence that is at least 99% identical to SEQ ID NO: 28; and
      (v) a 3' AAV ITR nucleotide sequence.

2. The AAV of claim 1, wherein the F8 coding sequence is silently altered.

3. The AAV of claim 1, wherein:
   the target locus is the internucleotide bond between nucleotide 126,476 and nucleotide 126,477 of the F8 gene; or
   the target locus is a nucleotide sequence adjacently 3' to nucleotide 126,476 of the F8 gene.

4. The AAV of claim 1, wherein:
   the 5' ITR nucleotide sequence has at least 95% sequence identity to SEQ ID NOs: 18 or 46, and the 3' ITR nucleotide sequence has at least 95% sequence identity to SEQ ID NOs: 19, 61, or 63; or
   the 5' ITR nucleotide sequence has at least 95% sequence identity to SEQ ID NO: 20, and the 3' ITR nucleotide sequence has at least 95% sequence identity to SEQ ID NO: 21.

5. The AAV of claim 1, wherein:
   the correction genome comprises a nucleic acid sequence selected from the group consisting of SEQ ID NOs: 39, 41, 43, and 45; and/or
   the correction genome consists of a nucleic acid sequence selected from the group consisting of SEQ ID NOs: 39, 41, 43, and 45.

6. The AAV of claim 1, wherein:
   the integration efficiency of the editing element into the target locus is at least 2% when the AAV is contacted in vitro in the absence of an exogenous nuclease with a population of B lymphoblastoid cells under standard AAV transduction conditions; and/or
   the allelic frequency of integration of the editing element into the target locus is at least 1% when the AAV is contacted in vitro in the absence of an exogenous nuclease with a population of B lymphoblastoid cells under standard AAV transduction conditions.

7. The AAV of claim 1, wherein: the AAV Clade F capsid protein comprises an amino acid sequence having at least 95% sequence identity with the amino acid sequence of amino acids 203-736 of SEQ ID NOs: 1, 2, 3, 4, 6, 7, 10, 11, 12, 13, 15, 16, or 17, wherein: (i) the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q, the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, (ii) (a) the amino acid in the capsid protein corresponding to amino acid 626 of SEQ ID NO: 2 is G, and the amino acid in the capsid protein corresponding to amino acid 718 of SEQ ID NO: 2 is G; (b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M; (c) the amino acid in the capsid protein corresponding to amino acid 505 of SEQ ID NO: 2 is R, and the amino acid in the capsid protein corresponding to amino acid 687 of SEQ ID NO: 2 is R; (d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C, or (iii) the capsid protein comprises the amino acid sequence of amino acids 203-736 of SEQ ID NOs: 1, 2, 3, 4, 6, 7, 10, 11, 12, 13, 15, 16, or 17.

8. The AAV of claim 1, wherein: the AAV Clade F capsid protein comprises an amino acid sequence having at least 95% sequence identity with the amino acid sequence of amino acids 138-736 of SEQ ID NOs: 1, 2, 3, 4, 5, 6, 7, 9, 10, 11, 12, 13, 15, 16, or 17, wherein: (i) the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, (ii) (a) the amino acid in the capsid protein corresponding to amino acid 626 of SEQ ID NO: 2 is G, and the amino acid in the capsid protein corresponding to amino acid 718 of SEQ ID NO: 2 is G; (b) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ ID NO: 2 is R, and the amino acid in the capsid protein corresponding to amino acid 681 of SEQ ID NO: 2 is M; (c) the amino acid in the capsid protein corresponding to amino acid 505 of SEQ ID NO: 2 is R, and the amino acid in the capsid protein corresponding to amino acid 687 of SEQ ID NO: 2 is R; (d) the amino acid in the capsid protein corresponding to amino acid 346 of SEQ ID NO: 2 is A, and the amino acid in the capsid protein corresponding to amino acid 505 of SEQ ID NO: 2 is R; or (e) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C, or (iii) the capsid protein comprises the amino acid sequence of amino acids 138-736 of SEQ ID NOs: 1, 2, 3, 4, 5, 6, 7, 9, 10, 11, 12, 13, 15, 16, or 17.

9. The AAV of claim 1, wherein: the AAV Clade F capsid protein comprises an amino acid sequence having at least 95% sequence identity with the amino acid sequence of amino acids 1-736 of SEQ ID NOs 1, 2, 3, 4, 5, 6, 7, 8, 9, 10, 11, 12, 13, 15, 16, or 17, wherein: (i) the amino acid in the capsid protein corresponding to amino acid 2 of SEQ ID NO: 2 is T; the amino acid in the capsid protein corresponding to amino acid 65 of SEQ ID NO: 2 is I; the amino acid in the capsid protein corresponding to amino acid 68 of SEQ ID NO: 2 is V; the amino acid in the capsid protein corresponding to amino acid 77 of SEQ ID NO: 2 is R; the amino acid in the capsid protein corresponding to amino acid 119 of SEQ ID NO: 2 is L; the amino acid in the capsid protein corresponding to amino acid 151 of SEQ ID NO: 2 is R; the amino acid in the capsid protein corresponding to amino acid 160 of SEQ ID NO: 2 is D; the amino acid in the capsid protein corresponding to amino acid 206 of SEQ ID NO: 2 is C; the amino acid in the capsid protein corresponding to amino acid 296 of SEQ ID NO: 2 is H; the amino acid in the capsid protein corresponding to amino acid 312 of SEQ ID NO: 2 is Q; the amino acid in the capsid protein corresponding to amino acid 346 of SEQ ID NO: 2 is A; the amino acid in the capsid protein corresponding to amino acid 464 of SEQ ID NO: 2 is N; the amino acid in the capsid protein corresponding to amino acid 468 of SEQ ID NO: 2 is S; the amino acid in the capsid protein corresponding to amino acid 501 of SEQ ID NO: 2 is I; the amino acid in the capsid protein corresponding to amino acid 505 of SEQ ID NO: 2 is R; the amino acid in the capsid protein corresponding to amino acid 590 of SEQ ID NO: 2 is R; the amino acid in the capsid protein corresponding to amino acid 626 of SEQ ID NO: 2 is G or Y; the amino acid in the capsid protein corresponding to amino acid 681 of SEQ ID NO: 2 is M; the amino acid in the capsid protein corresponding to amino acid 687 of SEQ ID NO: 2 is R; the amino acid in the capsid protein corresponding to amino acid 690 of SEQ ID NO: 2 is K; the amino acid in the capsid protein corresponding to amino acid 706 of SEQ ID NO: 2 is C; or, the amino acid in the capsid protein corresponding to amino acid 718 of SEQ ID NO: 2 is G, (ii) (a) the amino acid in the capsid protein corresponding to amino acid 2 of SEQ ID NO: 2 is T, and the amino acid in the capsid protein corresponding to amino acid 312 of SEQ ID NO: 2 is Q; (b) the amino acid in the capsid protein corresponding to amino acid 65 of SEQ ID NO: 2 is I, and the amino acid in the capsid protein corresponding to amino acid 626 of SEQ ID NO: 2 is Y; (c) the amino acid in the capsid protein corresponding to amino acid 77 of SEQ ID NO: 2 is R, and the amino acid in the capsid protein corresponding to amino acid 690 of SEQ ID NO: 2 is K; (d) the amino acid in the capsid protein corresponding to amino acid 119 of SEQ ID NO: 2 is L, and the amino acid in the capsid protein corresponding to amino acid 468 of SEQ D NO: 2 is S; (e) the amino acid in the capsid protein corresponding to amino acid 626 of SEQ ID NO: 2 is G, and the amino acid in the capsid protein corresponding to amino acid 718 of SEQ ID NO: 2 is G; (f) the amino acid in the capsid protein corresponding to amino acid 296 of SEQ ID NO: 2 is H, the amino acid in the capsid protein corresponding to amino acid 464 of SEQ ID NO: 2 is N, the amino acid in the capsid protein corresponding to amino acid 505 of SEQ D NO: 2 is R, and the amino acid in the capsid protein corresponding to amino acid 681 of SEQ ID NO: 2 is M; (g) the amino acid in the capsid protein corresponding to amino acid 505 of SEQ ID NO: 2 is R, and the amino acid in the capsid protein corresponding to amino acid 687 of SEQ ID NO: 2 is R; (h) the amino acid in the capsid protein corresponding to amino acid 346 of SEQ ID NO: 2 is A, and the amino acid in the capsid protein corresponding to amino acid 505 of SEQ ID NO: 2 is R; or (i) the amino acid in the capsid protein corresponding to amino acid 501 of SEQ ID NO: 2 is I, the amino acid in the capsid protein corresponding to amino acid 505 of SEQ ID NO: 2 is R, and the amino acid in the capsid protein corresponding to amino acid 706 of SEQ ID NO: 2 is C, or (iii) the capsid protein comprises the amino acid sequence of amino acids 1-736 of SEQ ID NOs: 1, 2, 3, 4, 5, 6, 7, 8, 9, 10, 11, 12, 13, 15, 16, or 17.

10. The AAV of claim 1, wherein the polyadenylation sequence is an exogenous polyadenylation sequence and/or an SV40 polyadenylation sequence comprising the nucleotide sequence set forth in SEQ ID NO: 23.

11. A pharmaceutical composition comprising the AAV of claim 1.

12. A packaging system for recombinant preparation of an AAV, wherein the packaging system comprises:

a) a Rep nucleotide sequence encoding one or more AAV Rep proteins;
b) a Cap nucleotide sequence encoding one or more AAV Clade F capsid proteins; and
c) a correction genome as set forth in claim 1, wherein the packaging system is operative in a cell for enclosing the correction genome in the capsid to form the AAV.

13. The packaging system of claim 12, wherein the packaging system comprises a first vector comprising the Rep nucleotide sequence and the Cap nucleotide sequence, and a second vector comprising the correction genome.

14. The packaging system of claim 12, wherein the Rep nucleotide sequence encodes an AAV2 Rep protein, wherein:
the AAV2 Rep protein is 78/68 or Rep 68/52; and/or
the AAV2 Rep protein comprises an amino acid sequence having a minimum percent sequence identity to the AAV2 Rep amino acid sequence of SEQ ID NO: 22, wherein the minimum percent sequence identity is at least 70% across the length of the amino acid sequence encoding the AAV2 Rep protein.

15. The packaging system of claim 12, further comprising a third vector, wherein: the third vector is a helper virus vector, wherein: the helper virus vector is an independent third vector; the helper virus vector is integral with the first vector; or the helper virus vector is integral with the second vector; and/or the third vector comprises genes encoding helper virus proteins.

16. The packaging system of claim 15, wherein the helper virus is selected from the group consisting of adenovirus, herpes virus, vaccinia virus, and cytomegalovirus (CMV), wherein: the adenovirus genome comprises one or more adenovirus RNA genes selected from the group consisting of E1, E2, E4 and VA; and/or the herpes virus is herpes simplex virus (HSV), wherein the HSV genome comprises one or more of HSV genes selected from the group consisting of UL5/8/52, ICP0, ICP4, ICP22 and UL30/UL42.

17. The packaging system of claim 15, wherein the first vector and the third vector are contained within a first transfecting plasmid.

18. The packaging system of claim 15, wherein the nucleotides of the second vector and the third vector are contained within a second transfecting plasmid.

19. The packaging system of claim 15, wherein the nucleotides of the first vector and the third vector are cloned into a recombinant helper virus.

20. The packaging system of claim 15, wherein the nucleotides of the second vector and the third vector are cloned into a recombinant helper virus.

21. A method for recombinant preparation of an AAV, the method comprising introducing the packaging system of claim 12 into a cell under conditions operative for enclosing the correction genome in the capsid to form the AAV.

* * * * *

SEQUENCE LISTING

<160> NUMBER OF SEQ ID NOS: 63

<210> SEQ ID NO 1
<211> LENGTH: 736
<212> TYPE: PRT

```
<213> ORGANISM: Artificial Sequence
<220> FEATURE:
<223> OTHER INFORMATION: adeno-associated AAV9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
```

```
            385                 390                 395                 400
        Pro Ser Gln Met Leu Arg Thr Gly Asn Asn Phe Gln Phe Ser Tyr Glu
                        405                 410                 415

Phe Glu Asn Val Pro Phe His Ser Ser Tyr Ala His Ser Gln Ser Leu
                        420                 425                 430

Asp Arg Leu Met Asn Pro Leu Ile Asp Gln Tyr Leu Tyr Tyr Leu Ser
                        435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ala Gln Ala Gln Ala Gln
                        580                 585                 590

Thr Gly Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                        660                 665                 670

Gln Tyr Ser Thr Gly Gln Val Ser Val Glu Ile Glu Trp Glu Leu Gln
                        675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

-continued

```
              20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Gln Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
```

```
Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
<223> OTHER INFORMATION: novel AAV isolate

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

-continued

```
Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Gly Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Ile Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
```

```
                    545                 550                 555                 560
Thr Asn Glu Glu Glu Ile Lys Thr Thr Asn Pro Val Ala Thr Glu Ser
                    565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
        610                 615                 620

Thr Tyr Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Asp
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
```

```
            180                 185                 190
Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605
```

Asp Arg Asp Val Tyr Leu Gln Gly Pro Ile Trp Ala Lys Ile Pro His
610             615                 620

Thr Asp Gly Asn Phe His Pro Ser Pro Leu Met Gly Gly Phe Gly Met
625             630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690             695                 700

Tyr Tyr Lys Ser Asn Asn Val Glu Phe Ala Val Asn Thr Glu Gly Val
705             710                 715                 720

Tyr Ser Glu Pro Arg Pro Ile Gly Thr Arg Tyr Leu Thr Arg Asn Leu
                725                 730                 735

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65              70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Leu Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145             150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225             230                 235                 240

```
Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655
```

-continued

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

-continued

```
Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
```

```
                705                 710                 715                 720
Tyr Ser Glu Pro Arg Pro Ile Gly Thr Arg Tyr Leu Thr Arg Asn Leu
                    725                 730                 735

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Val Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
```

```
                340                 345                 350
Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 736
<212> TYPE: PRT
<213> ORGANISM: Artificial Sequence
```

-continued

```
<220> FEATURE:
<223> OTHER INFORMATION: novel AAV isolate

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

-continued

Pro Ser Gln Met Leu Arg Thr Gly Asn Asn Phe Gln Phe Ser Tyr Glu
              405                 410                 415

Phe Glu Asn Val Pro Phe His Ser Ser Tyr Ala His Ser Gln Ser Leu
          420                 425                 430

Asp Arg Leu Met Asn Pro Leu Ile Asp Gln Tyr Leu Tyr Tyr Leu Ser
      435                 440                 445

Lys Thr Ile Asn Gly Ser Gly Gln Asn Gln Gln Thr Leu Lys Phe Ser
  450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
              485                 490                 495

Asn Asn Ser Glu Phe Ala Trp Pro Gly Ala Ser Ser Trp Ala Leu Asn
          500                 505                 510

Gly Arg Asn Ser Leu Met Asn Pro Gly Pro Ala Met Ala Ser His Lys
      515                 520                 525

Glu Gly Glu Asp Arg Phe Phe Pro Leu Ser Gly Ser Leu Ile Phe Gly
  530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
              565                 570                 575

Tyr Gly Gln Val Ala Thr Asn His Gln Ser Ala Gln Ala Gln Ala Gln
          580                 585                 590

Thr Gly Trp Val Gln Asn Gln Gly Ile Leu Pro Gly Met Val Trp Gln
      595                 600                 605

Asp Arg Asp Val Tyr Leu Gln Gly Pro Ile Trp Ala Lys Ile Pro His
  610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
              645                 650                 655

Asp Pro Pro Thr Ala Phe Asn Lys Asp Lys Leu Asn Ser Phe Ile Thr
          660                 665                 670

Gln Tyr Ser Thr Gly Gln Val Ser Val Glu Ile Glu Trp Glu Leu Gln
      675                 680                 685

Lys Glu Asn Ser Lys Arg Trp Asn Pro Glu Ile Gln Tyr Thr Ser Asn
  690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
              725                 730                 735

<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

```
Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445
```

```
Lys Thr Ile Asn Gly Ser Gly Gln Asn Gln Gln Thr Leu Lys Phe Ser
            450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Arg Ala Tyr Asp
65                  70                  75                  80
```

```
Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
```

```
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
            530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
            580                 585                 590
Thr Gly Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
            610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
            675                 680                 685
Lys Lys Asn Ser Lys Arg Trp Asn Pro Glu Ile Gln Tyr Thr Ser Asn
            690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp Gln
65                  70                  75                  80
Gln Leu Lys Ala Gly Asp Asn Pro Tyr Leu Lys Tyr Asn His Ala Asp
                85                  90                  95
Ala Glu Phe Gln Glu Arg Leu Lys Glu Asp Thr Ser Phe Gly Gly Asn
            100                 105                 110
Leu Gly Arg Ala Val Phe Gln Ala Lys Lys Arg Leu Leu Glu Pro Leu
        115                 120                 125
Gly Leu Val Glu Glu Ala Ala Lys Thr Ala Pro Gly Lys Lys Arg
```

-continued

```
                130                 135                 140
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro His Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Asn
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560
```

-continued

```
Thr Asn Glu Glu Ile Lys Thr Thr Asn Pro Val Ala Thr Glu Ser
            565                 570                 575
Tyr Gly Gln Val Ala Thr Asn His Gln Ser Ala Gln Ala Gln Ala Gln
        580                 585                 590
Thr Gly Trp Val Gln Asn Gln Gly Ile Leu Pro Gly Met Val Trp Gln
    595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
            645                 650                 655
Asp Pro Pro Thr Ala Phe Asn Lys Asp Lys Leu Asn Ser Phe Ile Thr
        660                 665                 670
Gln Tyr Ser Thr Gly Gln Val Ser Met Glu Ile Glu Trp Glu Leu Gln
    675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
            725                 730                 735
```

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

```
Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
```

```
Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
        595                 600                 605
```

```
Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 736
<212> TYPE: PRT
<213> ORGANISM: Artificial Sequence
<220> FEATURE:
<223> OTHER INFORMATION: novel AAV isolate

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240
```

```
Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
```

```
                    660                 665                 670
Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 15
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
```

```
                290                 295                 300
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Arg Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720
```

```
Tyr Ser Glu Pro Arg Pro Ile Gly Thr Arg Tyr Leu Thr Arg Asn Leu
            725                 730                 735

<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Ala Asp Ser Asp Tyr Gln Leu
            340                 345                 350
```

```
Pro Tyr Val Leu Gly Ser Ala His Glu Gly Cys Leu Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 17
<211> LENGTH: 736
<212> TYPE: PRT
<213> ORGANISM: Artificial Sequence
<220> FEATURE:
```

<223> OTHER INFORMATION: novel AAV isolate

<400> SEQUENCE: 17

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

| | | | | | | | | | | | |
|---|---|---|---|---|---|---|---|---|---|---|---|
|Pro|Ser|Gln|Met|Leu|Arg|Thr|Gly|Asn|Asn|Phe|Gln|Phe|Ser|Tyr|Glu|
| | | | |405| | | |410| | | |415|

Phe Glu Asn Val Pro Phe His Ser Ser Tyr Ala His Ser Gln Ser Leu
         420                 425                 430

Asp Arg Leu Met Asn Pro Leu Ile Asp Gln Tyr Leu Tyr Tyr Leu Ser
         435                 440                 445

Lys Thr Ile Asn Gly Ser Gly Gln Asn Gln Gln Thr Leu Lys Phe Ser
450                        455                 460

Val Ala Gly Pro Ser Asn Met Ala Val Gln Gly Arg Asn Tyr Ile Pro
465                   470                 475                 480

Gly Pro Ser Tyr Arg Gln Gln Arg Val Ser Thr Thr Val Thr Gln Asn
         485                 490                 495

Asn Asn Ser Glu Ile Ala Trp Pro Arg Ala Ser Ser Trp Ala Leu Asn
             500                 505                 510

Gly Arg Asn Ser Leu Met Asn Pro Gly Pro Ala Met Ala Ser His Lys
         515                 520                 525

Glu Gly Glu Asp Arg Phe Phe Pro Leu Ser Gly Ser Leu Ile Phe Gly
         530                 535                 540

Lys Gln Gly Thr Gly Arg Asp Asn Val Asp Ala Asp Lys Val Met Ile
545                   550                 555                 560

Thr Asn Glu Glu Glu Ile Lys Thr Thr Asn Pro Val Ala Thr Glu Ser
             565                 570                 575

Tyr Gly Gln Val Ala Thr Asn His Gln Ser Ala Gln Ala Gln Ala Gln
         580                 585                 590

Thr Gly Trp Val Gln Asn Gln Gly Ile Leu Pro Gly Met Val Trp Gln
         595                 600                 605

Asp Arg Asp Val Tyr Leu Gln Gly Pro Ile Trp Ala Lys Ile Pro His
610                        615                 620

Thr Asp Gly Asn Phe His Pro Ser Pro Leu Met Gly Gly Phe Gly Met
625                  630                 635                 640

Lys His Pro Pro Pro Gln Ile Leu Ile Lys Asn Thr Pro Val Pro Ala
             645                 650                 655

Asp Pro Pro Thr Ala Phe Asn Lys Asp Lys Leu Asn Ser Phe Ile Thr
         660                 665                 670

Gln Tyr Ser Thr Gly Gln Val Ser Val Glu Ile Glu Trp Glu Leu Gln
         675                 680                 685

Lys Glu Asn Ser Lys Arg Trp Asn Pro Glu Ile Gln Tyr Thr Ser Asn
         690                 695                 700

Tyr Cys Lys Ser Asn Asn Val Glu Phe Ala Val Asn Thr Glu Gly Val
705                   710                 715                 720

Tyr Ser Glu Pro Arg Pro Ile Gly Thr Arg Tyr Leu Thr Arg Asn Leu
         725                 730                 735

```
<210> SEQ ID NO 18
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 18
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145
```

<210> SEQ ID NO 19
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 19

```
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag agagggagtg gccaa                                         145
```

<210> SEQ ID NO 20
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 20

```
ctctcccccc tgtcgcgttc gctcgctcgc tggctcgttt ggggggtgg cagctcaaag    60 agctgccaga cgacggccct ctggccgtcg ccccccaaa cgagccagcg agcgagcgaa    120
cgcgacaggg gggagagtgc cacactctca agcaagggg ttttgta                  167
```

<210> SEQ ID NO 21
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 21

```
tacaaaacct ccttgcttga gagtgtggca ctctcccccc tgtcgcgttc gctcgctcgc    60
tggctcgttt ggggggtgg cagctcaaag agctgccaga cgacggccct ctggccgtcg    120 ccccccaaa cgagccagcg agcgagcgaa cgcgacaggg gggagag                  167
```

<210> SEQ ID NO 22
<211> LENGTH: 621
<212> TYPE: PRT
<213> ORGANISM: Artificial Sequence
<220> FEATURE:
<223> OTHER INFORMATION: AAV2 Rep

<400> SEQUENCE: 22

```
Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110
```

-continued

```
Arg Glu Lys Leu Ile Gln Arg Ile Tyr Arg Gly Ile Glu Pro Thr Leu
            115                 120                 125
Pro Asn Trp Phe Ala Val Thr Lys Thr Arg Asn Gly Ala Gly Gly Gly
        130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
        275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
Ala Gln Pro Ser Thr Ser Asp Ala Glu Ala Ser Ile Asn Tyr Ala Asp
        515                 520                 525
Arg Tyr Gln Asn Lys Cys Ser Arg His Val Gly Met Asn Leu Met Leu
```

```
                    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620

<210> SEQ ID NO 23
<211> LENGTH: 198
<212> TYPE: DNA
<213> ORGANISM: Artificial Sequence
<220> FEATURE:
<223> OTHER INFORMATION: SV40 polyadenylation sequence

<400> SEQUENCE: 23
gatccagaca tgataagata cattgatgag tttggacaaa ccacaactag aatgcagtga      60
aaaaaatgct ttatttgtga aatttgtgat gctattgctt tatttgtaac cattataagc     120
tgcaataaac aagttaacaa caacaattgc attcatttta tgtttcaggt tcaggggggag    180 gtgtgggagg ttttttaa                                                   198

<210> SEQ ID NO 24
<211> LENGTH: 26
<212> TYPE: DNA
<213> ORGANISM: Artificial Sequence
<220> FEATURE:
<223> OTHER INFORMATION: splice acceptor

<400> SEQUENCE: 24
ctgacctctt ctcttcctcc cacagg                                           26

<210> SEQ ID NO 25
<211> LENGTH: 209
<212> TYPE: PRT
<213> ORGANISM: Homo sapiens

<400> SEQUENCE: 25

Met Val Phe Phe Gly Asn Val Asp Ser Ser Gly Ile Lys His Asn Ile
1               5                   10                  15

Phe Asn Pro Pro Ile Ile Ala Arg Tyr Ile Arg Leu His Pro Thr His
            20                  25                  30

Tyr Ser Ile Arg Ser Thr Leu Arg Met Glu Leu Met Gly Cys Asp Leu
        35                  40                  45

Asn Ser Cys Ser Met Pro Leu Gly Met Glu Ser Lys Ala Ile Ser Asp
    50                  55                  60

Ala Gln Ile Thr Ala Ser Ser Tyr Phe Thr Asn Met Phe Ala Thr Trp
65                  70                  75                  80

Ser Pro Ser Lys Ala Arg Leu His Leu Gln Gly Arg Ser Asn Ala Trp
                85                  90                  95

Arg Pro Gln Val Asn Asn Pro Lys Glu Trp Leu Gln Val Asp Phe Gln
            100                 105                 110

Lys Thr Met Lys Val Thr Gly Val Thr Thr Gln Gly Val Lys Ser Leu
        115                 120                 125
```

```
Leu Thr Ser Met Tyr Val Lys Glu Phe Leu Ile Ser Ser Gln Asp
        130                 135                 140

Gly His Gln Trp Thr Leu Phe Phe Gln Asn Gly Lys Val Lys Val Phe
145                 150                 155                 160

Gln Gly Asn Gln Asp Ser Phe Thr Pro Val Val Asn Ser Leu Asp Pro
                165                 170                 175

Pro Leu Leu Thr Arg Tyr Leu Arg Ile His Pro Gln Ser Trp Val His
            180                 185                 190

Gln Ile Ala Leu Arg Met Glu Val Leu Gly Cys Glu Ala Gln Asp Leu
        195                 200                 205

Tyr

<210> SEQ ID NO 26
<211> LENGTH: 627
<212> TYPE: DNA
<213> ORGANISM: Homo sapiens

<400> SEQUENCE: 26
gtcttctttg gcaatgtgga ttcatctggg ataaaacaca atatttttaa ccctccaatt      60
attgctcgat acatccgttt gcacccaact cattatagca ttcgcagcac tcttcgcatg     120
gagttgatgg gctgtgattt aaatagttgc agcatgccat tgggaatgga gagtaaagca     180
atatcagatg cacagattac tgcttcatcc tactttacca atatgtttgc cacctggtct     240
ccttcaaaag ctcgacttca cctccaaggg aggagtaatg cctggagacc tcaggtgaat     300
aatccaaaag agtggctgca agtggacttc cagaagacaa tgaaagtcac aggagtaact     360
actcagggag taaaatctct gcttaccagc atgtatgtga aggagttcct catctccagc     420
agtcaagatg gccatcagtg gactctcttt tttcagaatg gcaaagtaaa ggttttttcag    480 ggaaatcaag actccttcac acctgtggtg aactctctag acccaccgtt actgactcgc     540
taccttcgaa ttcaccccca gagttgggtg caccagattg ccctgaggat ggaggttctg     600
ggctgcgagg cacaggacct ctactga                                         627

<210> SEQ ID NO 27
<211> LENGTH: 800
<212> TYPE: DNA
<213> ORGANISM: Homo sapiens

<400> SEQUENCE: 27
agtctaataa ggaaagcaga aaagcaaagc aaccttataa tatggtgcaa taatttgcta      60
taatgaagtt atatacaaag tgaagtagaa gcatagaaga agcagcacta aatttgtctg     120
ggtgagtcag agaaggctaa ccaggaaaaa tagtttctga actaacactt gaaggaggtg     180
tagcagttca tcactgacag tgatgttggg gtggtctggg tttcaggaga ggggaggaaa     240
ttggctttgg tctgaggctg aggtgtgggc aaagcattag cttatgtggg tccattagct     300
tatgtgagtc cacaaaaggt gtgtgtgtgt tgtgtgtat gtgtgtgtgt gtgtgtgtgt      360
gtgtgtgtgt acgaaatggg ggctcaatga tttggtagtg gtttggtttg tcaagaagca     420
ggctgggaac tcaataagca tctttccatt catttctact gtgtatccca cagcttcaca     480
cacacatgca catttcaaca ttggtgactg cttcacttgc acacctaagg taatgatgga     540
cacacctgta gcaatgtaga ttcttcctaa gctaataatt agtttcagga ggtagcacat     600
acatttaaaa ataggttaaa ataaagtgtt attttaattg gtaggtggat ctgttggcac     660
caatgattat tcacggcatc aagacccagg gtgcccgtca gaagttctcc agcctctaca     720
```

| | |
|---|---|
| tctctcagtt tatcatcatg tatagtcttg atgggaagaa gtggcagact tatcgaggaa | 780 |
| attccactgg aaccttaatg | 800 |

<210> SEQ ID NO 28
<211> LENGTH: 800
<212> TYPE: DNA
<213> ORGANISM: Homo sapiens

<400> SEQUENCE: 28

| | |
|---|---|
| gtatgtaatt agtcatttaa agggaatgcc tgaatacttt aaagaatttt ggcagatttc | 60 |
| agatattgga caaacactct tagcttccac aaacttaatt ccaaaaaata attttcact | 120 |
| tatgagcaat agagttatta cggacatatc agcaaaaatg tagtagtgtc aaggctcata | 180 |
| gatgatagaa atgaagagat gctgtattga tagaaatatg tgattcagga ctgtgtggat | 240 |
| tgatgattgt gagcttgctt atggatatcc taggtttgag gttatagtag gacaatcagg | 300 |
| ttgaaatgtc cagcaggcag taggtgaaag acaagtttag ggggcaaaac catggatgga | 360 |
| gatgaagatt catgacttcc acataaaagg atgggtgaaa ctttgggaat tgatgaattc | 420 |
| tctagaggtg agctcaagac ccttaaaggc ttaaaacctc agcgttattg tctactcttc | 480 |
| cctcattttt atgcccacaa atctggtcaa tcctttattt gcaatgcctc tcacatctct | 540 |
| ttcttctgtt tccatttata ccgctgttgc cacagcccag ggtcccatca cctcacactt | 600 |
| gatctattgt attacattcc taactagtct tcccccgttt ctaatctgtt ctccgataaa | 660 |
| agctgcacat cattttcagg ataatcatca gtcgcctgcc taaaacttt caatgtcttc | 720 |
| ccattgtctt tagaataaag ttcaaagtct tcaaatgacc ccaagcaaga taacttttgt | 780 |
| ttgccccttt agatccattt | 800 |

<210> SEQ ID NO 29
<211> LENGTH: 800
<212> TYPE: DNA
<213> ORGANISM: Homo sapiens

<400> SEQUENCE: 29

| | |
|---|---|
| agcagcacta aatttgtctg ggtgagtcag agaaggctaa ccaggaaaaa tagtttctga | 60 |
| actaacactt gaaggaggtg tagcagttca tcactgacag tgatgttggg gtgggtctgg | 120 |
| tttcaggaga ggggaggaaa ttggctttgg tctgaggctg aggtgtgggc aaagcattag | 180 |
| cttatgtggg tccattagct tatgtgagtc cacaaaaggt gtgtgtgtgt tgtgtgtat | 240 |
| gtgtgtgtgt gtgtgtgtgt gtgtgtgtgt acgaaatggg ggctcaatga tttggtagtg | 300 |
| gtttggtttg tcaagaagca ggctgggaac tcaataagca tctttccatt catttctact | 360 |
| gtgtatccca cagcttcaca cacacatgca catttcaaca ttggtgactg cttcacttgc | 420 |
| acacctaagg taatgatgga cacacctgta gcaatgtaga ttcttcctaa gctaataatt | 480 |
| agtttcagga ggtagcacat acatttaaaa ataggttaaa ataaagtgtt attttaattg | 540 |
| gtaggtggat ctgttggcac caatgattat tcacggcatc aagacccagg gtgcccgtca | 600 |
| gaagttctcc agcctctaca tctctcagtt tatcatcatg tatagtcttg atgggaagaa | 660 |
| gtggcagact tatcgaggaa attccactgg aaccttaatg gtatgtaatt agtcatttaa | 720 |
| agggaatgcc tgaatacttt aaagaatttt ggcagatttc agatattgga caaacactct | 780 |
| tagcttccac aaacttaatt | 800 |

<210> SEQ ID NO 30
<211> LENGTH: 800

```
<212> TYPE: DNA
<213> ORGANISM: Homo sapiens

<400> SEQUENCE: 30
ccaaaaaata attttcact tatgagcaat agagttatta cggacatatc agcaaaaatg      60
tagtagtgtc aaggctcata gatgatagaa atgaagagat gctgtattga tagaaatatg    120
tgattcagga ctgtgtggat tgatgattgt gagcttgctt atggatatcc taggtttgag    180
gttatagtag gacaatcagg ttgaaatgtc cagcaggcag taggtgaaag acaagtttag    240
ggggcaaaac catggatgga gatgaagatt catgacttcc acataaaagg atgggtgaaa    300
ctttgggaat tgatgaattc tctagaggtg agctcaagac ccttaaaggc ttaaaacctc    360
agcgttattg tctactcttc cctcattttt atgcccacaa atctggtcaa tcctttattt    420
gcaatgcctc tcacatctct ttcttctgtt tccatttata ccgctgttgc cacagcccag    480
ggtcccatca cctcacactt gatctattgt attacattcc taactagtct tccccccgttt   540
ctaatctgtt ctccgataaa agctgcacat cattttcagg ataatcatca gtcgcctgcc    600
taaaactttt caatgtcttc ccattgtctt tagaataaag ttcaaagtct tcaaatgacc    660
ccaagcaaga taactttgt ttgccccttt agatccattt tcctgcttct ctaccctgct     720
tcttgttctg tgaggtgagc ttgtatagaa tacatcaaca ggttaccttg tcctccagct    780
tttggttgga tttcaccaac                                               800

<210> SEQ ID NO 31
<211> LENGTH: 565
<212> TYPE: DNA
<213> ORGANISM: Homo sapiens

<400> SEQUENCE: 31
ggaaattggc tttggtctga ggctgaggtg tgggcaaagc attagcttat gtgggtccat      60
tagcttatgt gagtccacaa aaggtgtgtg tgtgtttgtg tgtatgtgtg tgtgtgtgtg    120
tgtgtgtgtg tgtgtacgaa atgggggctc aatgatttgg tagtggtttg gtttgtcaag    180
aagcaggctg ggaactcaat aagcatcttt ccattcattt ctactgtgta tcccacagct    240
tcacacacac atgcacattt caacattggt gactgcttca cttgcacacc taaggtaatg    300
atggacacac ctgtagcaat gtagattctt cctaagctaa taattagttt caggaggtag    360
cacatacatt taaaataggg ttaaaataaa gtgttatttt aattggtagg tggatctgtt    420
ggcaccaatg attattcacg gcatcaagac ccagggtgcc cgtcagaagt tctccagcct    480
ctacatctct cagtttatca tcatgtatag tcttgatggg aagaagtggc agacttatcg    540
aggaaattcc actggaacct taatg                                         565

<210> SEQ ID NO 32
<211> LENGTH: 241
<212> TYPE: DNA
<213> ORGANISM: Homo sapiens

<400> SEQUENCE: 32
gtatgtaatt agtcatttaa agggaatgcc tgaatacttt aaagaatttt ggcagatttc      60
agatattgga caaacactct tagcttccac aaacttaatt ccaaaaaata attttcact     120
tatgagcaat agagttatta cggacatatc agcaaaaatg tagtagtgtc aaggctcata    180
gatgatagaa atgaagagat gctgtattga tagaaatatg tgattcagga ctgtgtggat    240
t                                                                   241
```

<210> SEQ ID NO 33
<211> LENGTH: 1447
<212> TYPE: DNA
<213> ORGANISM: Artificial Sequence
<220> FEATURE:
<223> OTHER INFORMATION: pHMI-hF8-004-F8 coding sequence cassette
      (including FVIII partial coding sequence and SV40 polyA)

<400> SEQUENCE: 33

```
ggaaattggc tttggtctga ggctgaggtg tgggcaaagc attagcttat gtgggtccat      60
tagcttatgt gagtccacaa aaggtgtgtg tgtgtttgtg tgtatgtgtg tgtgtgtgtg     120
tgtgtgtgtg tgtgtacgaa atgggggctc aatgatttgg tagtggtttg gtttgtcaag     180
aagcaggctg ggaactcaat aagcatcttt ccattcattt ctactgtgta tcccacagct     240
tcacacacac atgcacattt caacattggt gactgcttca cttgcacacc taaggtaatg     300
atggacacac ctgtagcaat gtagattctt cctaagctaa taattagttt caggaggtag     360
cacatacatt taaaaatagg ttaaaataaa gtgttatttt aattggtagg tggatctgtt     420
ggcaccaatg attattcacg gcatcaagac ccagggtgcc cgtcagaagt tctccagcct     480
ctacatctct cagtttatca tcatgtatag tcttgatggg aagaagtggc agacttatcg     540
aggaaattcc actggaacct taatggtctt ctttggcaat gtggattcat ctgggataaa     600
acacaatatt tttaaccctc caattattgc tcgatacatc cgtttgcacc caactcatta     660
tagcattcgc agcactcttc gcatggagtt gatgggctgt gatttaaata gttgcagcat     720
gccattggga atggagagta aagcaatatc agatgcacag attactgctt catcctactt     780
taccaatatg tttgccacct ggtctccttc aaaagctcga cttcacctcc aagggaggag     840
taatgcctgg agacctcagg tgaataatcc aaaagagtgg ctgcaagtgg acttccagaa     900
gacaatgaaa gtcacaggag taactactca gggagtaaaa tctctgctta ccagcatgta     960
tgtgaaggag ttcctcatct ccagcagtca agatggccat cagtggactc tcttttttca    1020
gaatggcaaa gtaaaggttt ttcagggaaa tcaagactcc ttcacacctg tggtgaactc    1080
tctagaccca ccgttactga ctcgctacct tcgaattcac ccccagagtt gggtgcacca    1140
gattgccctg aggatggagg ttctgggctg cgaggcacag gacctctact gaaagcttta    1200
ccaaggcctc tcgagcctct agaactatag tgagtcgtat tacgtagatc cagacatgat    1260
aagatacatt gatgagtttg gacaaaccac aactagaatg cagtgaaaaa aatgctttat    1320
ttgtgaaatt tgtgatgcta ttgctttatt tgtaaccatt ataagctgca ataaacaagt    1380
taacaacaac aattgcattc attttatgtt tcaggttcag ggggaggtgt gggaggtttt    1440
ttaagct                                                              1447
```

<210> SEQ ID NO 34
<211> LENGTH: 806
<212> TYPE: DNA
<213> ORGANISM: Homo sapiens

<400> SEQUENCE: 34

```
ggaaattggc tttggtctga ggctgaggtg tgggcaaagc attagcttat gtgggtccat      60
tagcttatgt gagtccacaa aaggtgtgtg tgtgtttgtg tgtatgtgtg tgtgtgtgtg     120
tgtgtgtgtg tgtgtacgaa atgggggctc aatgatttgg tagtggtttg gtttgtcaag     180
aagcaggctg ggaactcaat aagcatcttt ccattcattt ctactgtgta tcccacagct     240
tcacacacac atgcacattt caacattggt gactgcttca cttgcacacc taaggtaatg     300
```

```
atggacacac ctgtagcaat gtagattctt cctaagctaa taattagttt caggaggtag    360
cacatacatt taaaaatagg ttaaaataaa gtgttatttt aattggtagg tggatctgtt    420
ggcaccaatg attattcacg gcatcaagac ccagggtgcc cgtcagaagt tctccagcct    480
ctacatctct cagtttatca tcatgtatag tcttgatggg aagaagtggc agacttatcg    540
aggaaattcc actggaacct taatggtatg taattagtca tttaagggga atgcctgaat    600
actttaaaga attttggcag atttcagata ttggacaaac actcttagct tccacaaact    660
taattccaaa aaataatttt tcacttatga gcaatagagt tattacggac atatcagcaa    720
aaatgtagta gtgtcaaggc tcatagatga tagaaatgaa gagatgctgt attgatagaa    780
atatgtgatt caggactgtg tggatt                                         806
```

<210> SEQ ID NO 35
<211> LENGTH: 246
<212> TYPE: DNA
<213> ORGANISM: Artificial Sequence
<220> FEATURE:
<223> OTHER INFORMATION: SV40 polyadenylation sequence

<400> SEQUENCE: 35

```
caaggcctct cgagcctcta gaactatagt gagtcgtatt acgtagatcc agacatgata     60
agatacattg atgagtttgg acaaaccaca actagaatgc agtgaaaaaa atgctttatt    120
tgtgaaattt gtgatgctat tgctttattt gtaaccatta taagctgcaa taaacaagtt    180
aacaacaaca attgcattca ttttatgttt caggttcagg ggaggtgtg ggaggttttt     240 taagct                                                               246
```

<210> SEQ ID NO 36
<211> LENGTH: 198
<212> TYPE: DNA
<213> ORGANISM: Artificial Sequence
<220> FEATURE:
<223> OTHER INFORMATION: SV40 polyadenylation sequence

<400> SEQUENCE: 36

```
ttaaaaaacc tcccacacct cccctgaac ctgaaacata aaatgaatgc aattgttgtt      60
gttaacttgt ttattgcagc ttataatggt tacaaataaa gcaatagcat cacaaatttc    120
acaaataaag cattttttc actgcattct agttgtggtt tgtccaaact catcaatgta    180
tcttatcatg tctggatc                                                  198
```

<210> SEQ ID NO 37
<211> LENGTH: 246
<212> TYPE: DNA
<213> ORGANISM: Artificial Sequence
<220> FEATURE:
<223> OTHER INFORMATION: SV40 polyadenylation sequence

<400> SEQUENCE: 37

```
agcttaaaaa acctcccaca cctcccctg aacctgaaac ataaaatgaa tgcaattgtt       60
gttgttaact tgtttattgc agcttataat ggttacaaat aaagcaatag catcacaaat    120
ttcacaaata aagcattttt ttcactgcat tctagttgtg gtttgtccaa actcatcaat    180
gtatcttatc atgtctggat ctacgtaata cgactcacta gttctaga ggctcgagag    240 gccttg                                                               246
```

<210> SEQ ID NO 38
<211> LENGTH: 2236

<212> TYPE: DNA
<213> ORGANISM: Artificial Sequence
<220> FEATURE:
<223> OTHER INFORMATION: pHMI-hF8-001-F8 correction genome

<400> SEQUENCE: 38

```
agtctaataa ggaaagcaga aaagcaaagc aaccttataa tatggtgcaa taatttgcta      60
taatgaagtt atatacaaag tgaagtagaa gcatagaaga agcagcacta aatttgtctg     120
ggtgagtcag agaaggctaa ccaggaaaaa tagtttctga actaacactt gaaggaggtg     180
tagcagttca tcactgacag tgatgttggg gtgggtctgg tttcaggaga ggggaggaaa     240
ttggctttgg tctgaggctg aggtgtgggc aaagcattag cttatgtggg tccattagct     300
tatgtgagtc cacaaaaggt gtgtgtgtgt ttgtgtgtat gtgtgtgtgt gtgtgtgtgt     360
gtgtgtgtgt acgaaatggg ggctcaatga tttggtagtg gtttggtttg tcaagaagca     420
ggctgggaac tcaataagca tctttccatt catttctact gtgtatccca cagcttcaca     480
cacacatgca catttcaaca ttggtgactg cttcacttgc acacctaagg taatgatgga     540
cacacctgta gcaatgtaga ttcttcctaa gctaataatt agtttcagga ggtagcacat     600
acatttaaaa ataggttaaa ataaagtgtt attttaattg gtaggtggat ctgttggcac     660
caatgattat tcacggcatc aagacccagg gtgcccgtca gaagttctcc agcctctaca     720
tctctcagtt tatcatcatg tatagtcttg atgggaagaa gtggcagact tatcgaggaa     780
attccactgg aaccttaatg gtcttctttg gcaatgtgga ttcatctggg ataaaacaca     840
atatttttaa ccctccaatt attgctcgat acatccgttt gcacccaact cattatagca     900
ttcgcagcac tcttcgcatg gagttgatgg gctgtgattt aaatagttgc agcatgccat     960
tgggaatgga gagtaaagca atatcagatg cacagattac tgcttcatcc tactttacca    1020
atatgtttgc cacctggtct ccttcaaaag ctcgacttca cctccaaggg aggagtaatg    1080
cctggagacc tcaggtgaat aatccaaaag agtggctgca agtggacttc cagaagacaa    1140
tgaaagtcac aggagtaact actcagggag taaaatctct gcttaccagc atgtatgtga    1200
aggagttcct catctccagc agtcaagatg gccatcagtg gactctcttt tttcagaatg    1260
gcaaagtaaa ggttttttcag ggaaatcaag actccttcac acctgtggtg aactctctag    1320
acccaccgtt actgactcgc taccttcgaa ttcaccccca gagttgggtg caccagattg    1380
ccctgaggat ggaggttctg ggctgcgagg cacaggacct ctactgaaag ctttacgtat    1440
gtaattagtc atttaaaggg aatgcctgaa tactttaaag aattttggca gatttcagat    1500
attggacaaa cactcttagc ttccacaaac ttaattccaa aaaataattt ttcacttatg    1560
agcaatagag ttattacgga catatcagca aaaatgtagt agtgtcaagg ctcatagatg    1620
atagaaatga gagatgctg tattgataga aatatgtgat tcaggactgt gtggattgat    1680
gattgtgagc ttgcttatgg atatcctagg tttgaggtta tagtaggaca atcaggttga    1740
aatgtccagc aggcagtagg tgaaagacaa gtttaggggg caaaaccatg gatggagatg    1800
aagattcatg acttccacat aaaaggatgg gtgaaacttt gggaattgat gaattctcta    1860
gaggtgagct caagaccctt aaaggcttaa aacctcagcg ttattgtcta ctcttccctc    1920
atttttatgc ccacaaatct ggtcaatcct ttatttgcaa tgcctctcac atctctttct    1980
tctgtttcca tttataccgc tgttgccaca gcccagggtc ccatcacctc acacttgatc    2040
tattgtatta cattcctaac tagtcttccc ccgtttctaa tctgttctcc gataaaagct    2100
gcacatcatt ttcaggataa tcatcagtcg cctgcctaaa acttttcaat gtcttcccat    2160
```

```
tgtcttttaga ataaagttca aagtcttcaa atgaccccaa gcaagataac ttttgtttgc    2220
ccctttagat ccattt                                                    2236

<210> SEQ ID NO 39
<211> LENGTH: 2482
<212> TYPE: DNA
<213> ORGANISM: Artificial Sequence
<220> FEATURE:
<223> OTHER INFORMATION: pHMI-hF8-002-F8 correction genome

<400> SEQUENCE: 39
agtctaataa ggaaagcaga aaagcaaagc aaccttataa tatggtgcaa taatttgcta      60
taatgaagtt atatacaaag tgaagtagaa gcatagaaga agcagcacta aatttgtctg     120
ggtgagtcag agaaggctaa ccaggaaaaa tagtttctga actaacactt gaaggaggtg     180
tagcagttca tcactgacag tgatgttggg gtgggtctgg tttcaggaga ggggaggaaa     240 ttggcttttgg tctgaggctg aggtgtgggc aaagcattag cttatgtggg tccattagct    300
tatgtgagtc cacaaaaggt gtgtgtgtgt tgtgtgtat gtgtgtgtgt gtgtgtgtgt      360
gtgtgtgtgt acgaaatggg ggctcaatga tttggtagtg gtttggtttg tcaagaagca     420
ggctgggaac tcaataagca tctttccatt catttctact gtgtatccca cagcttcaca     480
cacacatgca catttcaaca ttggtgactg cttcacttgc acacctaagg taatgatgga     540
cacacctgta gcaatgtaga ttcttcctaa gctaataatt agtttcagga ggtagcacat     600
acatttaaaa ataggttaaa ataaagtgtt attttaattg gtaggtggat ctgttggcac     660
caatgattat tcacggcatc aagacccagg gtgcccgtca gaagttctcc agcctctaca     720
tctctcagtt tatcatcatg tatagtcttg atgggaagaa gtggcagact tatcgaggaa     780
attccactgg aacctaatg gtcttctttg gcaatgtgga ttcatctggg ataaaacaca      840 atattttttaa ccctccaatt attgctcgat acatccgttt gcacccaact cattatagca    900
ttcgcagcac tcttcgcatg gagttgatgg gctgtgattt aaatagttgc agcatgccat     960
tgggaatgga gagtaaagca atatcagatg cacagattac tgcttcatcc tactttacca    1020
atatgtttgc cacctggtct ccttcaaaag ctcgacttca cctccaaggg aggagtaatg    1080
cctggagacc tcaggtgaat aatccaaaag agtggctgca agtggacttc cagaagacaa    1140
tgaaagtcac aggagtaact actcagggag taaaatctct gcttaccagc atgtatgtga    1200
aggagttcct catctccagc agtcaagatg gccatcagtg gactctcttt tttcagaatg    1260
gcaaagtaaa ggttttttcag ggaaatcaag actccttcac acctgtggtg aactctctag    1320
acccaccgtt actgactcgc taccttcgaa ttcacccca gagttgggtg caccagattg      1380
ccctgaggat ggaggttctg ggctgcgagg cacaggacct ctactgaaag ctttaccaag    1440
gcctctcgag cctctagaac tatagtgagt cgtattacgt agatccagac atgataagat    1500
acattgatga gtttggacaa accacaacta gaatgcagtg aaaaaaatgc tttatttgtg    1560
aaatttgtga tgctattgct ttatttgtaa ccattataag ctgcaataaa caagttaaca    1620
acaacaattg cattcatttt atgtttcagg ttcaggggga ggtgtgggag gttttttaag    1680
ctgtatgtaa ttagtcattt aaagggaatg cctgaatact ttaaagaatt ttggcagatt    1740
tcagatattg gacaaacact cttagcttcc acaaacttaa ttccaaaaaa taatttttca    1800
cttatgagca atagagttat tacggacata tcagcaaaaa tgtagtagtg tcaaggctca    1860
tagatgatag aaatgaagag atgctgtatt gatagaaata tgtgattcag gactgtgtgg    1920
attgatgatt gtgagcttgc ttatggatat cctaggtttg aggttatagt aggacaatca    1980
```

| | | |
|---|---|---|
| ggttgaaatg tccagcaggc agtaggtgaa agacaagttt aggggcaaaa accatggatg | 2040 |
| gagatgaaga ttcatgactt ccacataaaa ggatgggtga aactttggga attgatgaat | 2100 |
| tctctagagg tgagctcaag acccttaaag gcttaaaacc tcagcgttat tgtctactct | 2160 |
| tccctcattt ttatgcccac aaatctggtc aatcctttat ttgcaatgcc tctcacatct | 2220 |
| ctttcttctg tttccattta taccgctgtt gccacagccc agggtcccat cacctcacac | 2280 |
| ttgatctatt gtattacatt cctaactagt cttcccccgt ttctaatctg ttctccgata | 2340 |
| aaagctgcac atcattttca ggataatcat cagtcgcctg cctaaaactt tcaatgtct | 2400 |
| tcccattgtc tttagaataa agttcaaagt cttcaaatga ccccaagcaa gataactttt | 2460 |
| gtttgcccct ttagatccat tt | 2482 |

<210> SEQ ID NO 40
<211> LENGTH: 1442
<212> TYPE: DNA
<213> ORGANISM: Artificial Sequence
<220> FEATURE:
<223> OTHER INFORMATION: pHMI-hF8-003-F8 correction genome

<400> SEQUENCE: 40

| | | |
|---|---|---|
| ggaaattggc tttggtctga ggctgaggtg tgggcaaagc attagcttat gtgggtccat | 60 |
| tagcttatgt gagtccacaa aaggtgtgtg tgtgtttgtg tgtatgtgtg tgtgtgtgtg | 120 |
| tgtgtgtgtg tgtgtacgaa atgggggctc aatgatttgg tagtggtttg gtttgtcaag | 180 |
| aagcaggctg ggaactcaat aagcatcttt ccattcattt ctactgtgta tcccacagct | 240 |
| tcacacacac atgcacattt caacattggt gactgcttca cttgcacacc taaggtaatg | 300 |
| atggacacac ctgtagcaat gtagattctt cctaagctaa taattagttt caggaggtag | 360 |
| cacatacatt taaaaatagg ttaaaataaa gtgttatttt aattggtagg tggatctgtt | 420 |
| ggcaccaatg attattcacg gcatcaagac ccagggtgcc cgtcagaagt ctccagcct | 480 |
| ctacatctct cagtttatca tcatgtatag tcttgatggg aagaagtggc agacttatcg | 540 |
| aggaaattcc actggaacct taatggtctt ctttggcaat gtggattcat ctgggataaa | 600 |
| acacaatatt tttaaccctc caattattgc tcgatacatc cgtttgcacc caactcatta | 660 |
| tagcattcgc agcactcttc gcatggagtt gatgggctgt gatttaaata gttgcagcat | 720 |
| gccattggga atggagagta aagcaatatc agatgcacag attactgctt catcctactt | 780 |
| taccaatatg tttgccacct ggtctccttc aaaagctcga cttcacctcc aagggaggag | 840 |
| taatgcctgg agacctcagg tgaataatcc aaaagagtgg ctgcaagtgg acttccagaa | 900 |
| gacaatgaaa gtcacaggag taactactca gggagtaaaa tctctgctta ccagcatgta | 960 |
| tgtgaaggag ttcctcatct ccagcagtca agatggccat cagtggacct ctttttttca | 1020 |
| gaatggcaaa gtaaaggttt ttcagggaaa tcaagactcc ttcacacctg tggtgaactc | 1080 |
| tctagaccca ccgttactga ctcgctacct tcgaattcac ccccagagtt gggtgcacca | 1140 |
| gattgccctg aggatggagg ttctgggctg cgaggcacag gacctctact gaaagcttta | 1200 |
| cgtatgtaat tagtcattta aagggaatgc ctgaatactt taaagaattt tggcagattt | 1260 |
| cagatattgg acaaacactc ttagcttcca caaacttaat tccaaaaaat aattttcac | 1320 |
| ttatgagcaa tagagttatt acggacatat cagcaaaaat gtagtagtgt caaggctcat | 1380 |
| agatgataga aatgaagaga tgctgtattg atagaaatat gtgattcagg actgtgtgga | 1440 |
| tt | 1442 |

<210> SEQ ID NO 41
<211> LENGTH: 1688
<212> TYPE: DNA
<213> ORGANISM: Artificial Sequence
<220> FEATURE:
<223> OTHER INFORMATION: pHMI-hF8-004-F8 correction genome

<400> SEQUENCE: 41

```
ggaaattggc tttggtctga ggctgaggtg tgggcaaagc attagcttat gtgggtccat      60
tagcttatgt gagtccacaa aaggtgtgtg tgtgtttgtg tgtatgtgtg tgtgtgtgtg     120
tgtgtgtgtg tgtgtacgaa atgggggctc aatgatttgg tagtggtttg gtttgtcaag     180
aagcaggctg ggaactcaat aagcatcttt ccattcattt ctactgtgta tcccacagct     240
tcacacacac atgcacattt caacattggt gactgcttca cttgcacacc taaggtaatg     300
atggacacac ctgtagcaat gtagattctt cctaagctaa taattagttt caggaggtag     360
cacatacatt taaaaatagg ttaaaataaa gtgttatttt aattggtagg tggatctgtt     420
ggcaccaatg attattcacg gcatcaagac ccagggtgcc cgtcagaagt tctccagcct     480
ctacatctct cagtttatca tcatgtatag tcttgatggg aagaagtggc agacttatcg     540
aggaaattcc actggaacct taatggtctt ctttggcaat gtggattcat ctgggataaa     600
acacaatatt tttaaccctc caattattgc tcgatacatc cgtttgcacc caactcatta     660
tagcattcgc agcactcttc gcatggagtt gatgggctgt gatttaaata gttgcagcat     720
gccattggga atggagagta aagcaatatc agatgcacag attactgctt catcctactt     780
taccaatatg tttgccacct ggtctccttc aaaagctcga cttcacctcc aagggaggag     840
taatgcctgg agacctcagg tgaataatcc aaaagagtgg ctgcaagtgg acttccagaa     900
gacaatgaaa gtcacaggag taactactca gggagtaaaa tctctgctta ccagcatgta     960
tgtgaaggag ttcctcatct ccagcagtca agatggccat cagtggactc tcttttttca    1020
gaatggcaaa gtaaaggttt ttcagggaaa tcaagactcc ttcacacctg tggtgaactc    1080
tctagaccca ccgttactga ctcgctacct tcgaattcac ccccagagtt gggtgcacca    1140
gattgccctg aggatggagg ttctgggctg cgaggcacag gacctctact gaaagcttta    1200
ccaaggcctc tcgagcctct agaactatag tgagtcgtat tacgtagatc cagacatgat    1260
aagatacatt gatgagtttg gacaaaccac aactagaatg cagtgaaaaa atgctttat    1320
ttgtgaaatt tgtgatgcta ttgctttatt tgtaaccatt ataagctgca ataaacaagt    1380
taacaacaac aattgcattc attttatgtt tcaggttcag ggggaggtgt gggaggtttt    1440
ttaagctgta tgtaattagt catttaaagg gaatgcctga atactttaaa gaattttggc    1500
agatttcaga tattggacaa acactcttag cttccacaaa cttaattcca aaaataatt    1560
tttcacttat gagcaataga gttattacgg acatatcagc aaaaatgtag tagtgtcaag    1620
gctcatagat gatagaaatg aagagatgct gtattgatag aaatatgtga ttcaggactg    1680
tgtggatt                                                             1688
```

<210> SEQ ID NO 42
<211> LENGTH: 2640
<212> TYPE: DNA
<213> ORGANISM: Artificial Sequence
<220> FEATURE:
<223> OTHER INFORMATION: pHMI-hF8-001-F8 correction genome including
     ITRs

<400> SEQUENCE: 42

-continued

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgcata tggcagtcta ataaggaaag cagaaaagca aagcaacctt     240
ataatatggt gcaataattt gctataatga agttatatac aaagtgaagt agaagcatag     300
aagaagcagc actaaatttg tctgggtgag tcagagaagg ctaaccagga aaaatagttt     360
ctgaactaac acttgaagga ggtgtagcag ttcatcactg acagtgatgt tggggtgggt     420
ctggtttcag gagaggggag gaaattggct ttggtctgag gctgaggtgt gggcaaagca     480
ttagcttatg tgggtccatt agcttatgtg agtccacaaa aggtgtgtgt gtgtttgtgt     540
gtatgtgtgt gtgtgtgtgt gtgtgtgtgt gtgtacgaaa tggggctca atgatttggt      600
agtggtttgg tttgtcaaga agcaggctgg gaactcaata agcatctttc cattcatttc     660
tactgtgtat cccacagctt cacacacaca tgcacatttc aacattggtg actgcttcac     720
ttgcacacct aaggtaatga tggacacacc tgtagcaatg tagattcttc ctaagctaat     780
aattagtttc aggaggtagc acatacattt aaaaataggt taaaataaag tgttattta     840
attggtaggt ggatctgttg gcaccaatga ttattcacgg catcaagacc cagggtgccc     900
gtcagaagtt ctccagcctc tacatctctc agtttatcat catgtatagt cttgatggga     960
agaagtggca gacttatcga ggaaattcca ctggaacctt aatggtcttc tttggcaatg    1020
tggattcatc tgggataaaa cacaatattt ttaaccctcc aattattgct cgatacatcc    1080
gtttgcaccc aactcattat agcattcgca gcactcttcg catggagttg atgggctgtg    1140
atttaaatag ttgcagcatg ccattgggaa tggagagtaa agcaatatca gatgcacaga    1200
ttactgcttc atcctacttt accaatatgt ttgccacctg gtctccttca aaagctcgac    1260
ttcacctcca agggaggagt aatgcctgga gacctcaggt gaataatcca aaagagtggc    1320
tgcaagtgga cttccagaag acaatgaaag tcacaggagt aactactcag ggagtaaaat    1380
ctctgcttac cagcatgtat gtgaaggagt tcctcatctc cagcagtcaa gatggccatc    1440
agtggactct ctttttttcag aatggcaaag taaaggtttt tcagggaaat caagactcct    1500
tcacacctgt ggtgaactct ctagacccac cgttactgac tcgctacctt cgaattcacc    1560
cccagagttg ggtgcaccag attgccctga ggatggaggt tctgggctgc gaggcacagg    1620
acctctactg aaagctttac gtatgtaatt agtcatttaa agggaatgcc tgaatacttt    1680
aaagaatttt ggcagatttc agatattgga caaacactct tagcttccac aaacttaatt    1740
ccaaaaaata atttttcact tatgagcaat agagttatta cggacatatc agcaaaaatg    1800
tagtagtgtc aaggctcata gatgatgaa atgaagagat gctgtattga tagaaatatg    1860
tgattcagga ctgtgtggat tgatgattgt gagcttgctt atggatatcc taggtttgag    1920
gttatagtag acaatcagg ttgaaatgtc cagcaggcag taggtgaaag acaagtttag     1980
ggggcaaaac catggatgga gatgaagatt catgacttcc acataaaagg atgggtgaaa    2040
ctttgggaat tgatgaattc tctagaggtg agctcaagac ccttaaaggc ttaaaacctc    2100
agcgttattg tctactcttc cctcatttt atgcccacaa atctggtcaa tcctttattt    2160
gcaatgcctc tcacatctct ttcttctgtt tccatttata ccgctgttgc cacagcccag    2220
ggtcccatca cctcacactt gatctattgt attacattcc taactagtct tcccccgttt    2280
ctaatctgtt ctccgataaa agctgcacat cattttcagg ataatcatca gtcgcctgcc    2340
taaaactttt caatgtcttc ccattgtctt tagaataaag ttcaaagtct tcaaatgacc    2400
```

```
ccaagcaaga taactttttgt ttgccccttt agatccattt aaatgcaggt ctagatacgt   2460
agataagtag catggcgggt taatcattaa ctacaaggaa ccctagtga tggagttggc    2520 cactccctct ctgcgcgctc gctcgctcac tgaggccggg cgaccaaagg tcgcccgacg    2580
cccgggcttt gcccgggcgg cctcagtgag cgagcgagcg cgcagagagg gagtggccaa    2640
```

<210> SEQ ID NO 43
<211> LENGTH: 2886
<212> TYPE: DNA
<213> ORGANISM: Artificial Sequence
<220> FEATURE:
<223> OTHER INFORMATION: pHMI-hF8-002-F8 correction genome including
      ITRs

<400> SEQUENCE: 43

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtgagtcg tgacgtgaat tacgtcatag      180
ggttagggag gtcctgcata tggcagtcta ataaggaaag cagaaaagca aagcaacctt     240
ataatatggt gcaataattt gctataatga agttatatac aaagtgaagt agaagcatag     300
aagaagcagc actaaatttg tctgggtgag tcagagaagg ctaaccagga aaaatagttt     360
ctgaactaac acttgaagga ggtgtagcag ttcatcactg acagtgatgt tggggtgggt     420
ctggtttcag gagaggggag gaaattggct ttggtctgag gctgaggtgt gggcaaagca     480
ttagcttatg tgggtccatt agcttatgtg agtccacaaa aggtgtgtgt gtgtttgtgt     540
gtatgtgtgt gtgtgtgtgt gtgtgtgtgt gtgtacgaaa tgggggctca atgatttggt     600
agtggtttgg tttgtcaaga agcaggctgg gaactcaata agcatctttc cattcatttc     660
tactgtgtat cccacagctt cacacacaca tgcacatttc aacattggtg actgcttcac     720
ttgcacacct aaggtaatga tggacacacc tgtagcaatg tagattcttc ctaagctaat     780
aattagtttc aggaggtagc acatacattt aaaaatagt taaaataaag tgttattta      840 attggtaggt ggatctgttg gcaccaatga ttattcacgg catcaagacc cagggtgccc     900
gtcagaagtt ctccagcctc tacatctctc agtttatcat catgtatagt cttgatggga     960
agaagtggca gacttatcga ggaaattcca ctggaacctt aatggtcttc tttggcaatg    1020
tggattcatc tgggataaaa cacaatattt ttaaccctcc aattattgct cgatacatcc    1080
gtttgcaccc aactcattat agcattcgca gcactcttcg catggagttg atgggctgtg    1140
atttaaatag ttgcagcatg ccattgggaa tggagagtaa agcaatatca gatgcacaga    1200
ttactgcttc atcctacttt accaatatgt ttgccacctg gtctccttca aaagctcgac    1260
ttcacctcca agggaggagt aatgcctgga gacctcaggt gaataatcca aaagagtggc    1320
tgcaagtgga cttccagaag acaatgaaag tcacaggagt aactactcag ggagtaaaat    1380
ctctgcttac cagcatgtat gtgaaggagt tcctcatctc cagcagtcaa gatggccatc    1440
agtggactct ctttttttcag aatggcaaag taaaggtttt tcaggaaaat caagactcct    1500
tcacacctgt ggtgaactct ctagacccac cgttactgac tcgctacctt cgaattcacc    1560
cccagagttg ggtgcaccag attgccctga ggatggaggt tctgggctgc gaggcacagg    1620
acctctactg aaagctttac caaggcctct cgagcctcta gaactatagt gagtcgtatt    1680
acgtagatcc agacatgata agatacattg atgagtttgg acaaaccaca actagaatgc    1740
agtgaaaaaa atgctttatt tgtgaaattt gtgatgctat tgctttattt gtaaccatta    1800
```

```
taagctgcaa taaacaagtt aacaacaaca attgcattca ttttatgttt caggttcagg    1860
gggaggtgtg ggaggttttt taagctgtat gtaattagtc atttaaaggg aatgcctgaa    1920
tactttaaag aattttggca gatttcagat attggacaaa cactcttagc ttccacaaac    1980
ttaattccaa aaaataattt ttcacttatg agcaatagaa ttattacgga catatcagca    2040
aaaatgtagt agtgtcaagg ctcatagatg atagaaatga agagatgctg tattgataga    2100
aatatgtgat tcaggactgt gtggattgat gattgtgagc ttgcttatgg atatcctagg    2160
tttgaggtta tagtaggaca atcaggttga aatgtccagc aggcagtagg tgaaagacaa    2220
gtttaggggg caaaaccatg gatggagatg aagattcatg acttccacat aaaaggatgg    2280
gtgaaacttt gggaattgat gaattctcta gaggtgagct caagacccttt aaaggcttaa    2340 aacctcagcg ttattgtcta ctcttccctc attttttatgc ccacaaatct ggtcaatcct    2400
ttatttgcaa tgcctctcac atctctttct tctgtttcca tttataccgc tgttgccaca    2460
gcccagggtc ccatcacctc acacttgatc tattgtatta cattcctaac tagtcttccc    2520
ccgtttctaa tctgttctcc gataaaagct gcacatcatt ttcaggataa tcatcagtcg    2580
cctgcctaaa acttttcaat gtcttcccat tgtctttaga ataaagttca aagtcttcaa    2640
atgaccccaa gcaagataac ttttgtttgc ccctttagat ccatttaaat gcaggtctag    2700
atacgtagat aagtagcatg gcgggttaat cattaactac aaggaacccc tagtgatgga    2760
gttggccact ccctctctgc gcgctcgctc gctcactgag gccgggcgac caaaggtcgc    2820
ccgacgcccg ggctttgccc gggcggcctc agtgagcgag cgagcgcgca gagggagt     2880 ggccaa                                                               2886
```

<210> SEQ ID NO 44
<211> LENGTH: 1846
<212> TYPE: DNA
<213> ORGANISM: Artificial Sequence
<220> FEATURE:
<223> OTHER INFORMATION: pHMI-hF8-003-F8 correction genome including ITRs

<400> SEQUENCE: 44

```
ttggccactc cctctctgcg cgctcgctcg ctcactgagg ccgggcgacc aaaggtcgcc     60
cgacgcccgg gctttgcccg gcggcctca gtgagcgagc gagcgcgcag agggagtg      120 gccaactcca tcactagggg ttcctggagg ggtggagtcg tgacgtgaat tacgtcatag    180
ggttagggag gtcctgcata tggcggaaat tggctttggt ctgaggctga ggtgtgggca    240
aagcattagc ttatgtgggt ccattagctt atgtgagtcc acaaaaggtg tgtgtgtgtt    300
tgtgtgtatg tgtgtgtgtg tgtgtgtgtg tgtgtgtgta cgaaatgggg gctcaatgat    360
ttggtagtgg tttggtttgt caagaagcag gctgggaact caataagcat ctttccattc    420
atttctactg tgtatcccac agcttccacac acacatgcac atttcaacat tggtgactgc    480
ttcacttgca cacctaaggt aatgatggac acacctgtag caatgtagat tcttcctaag    540
ctaataatta gtttcaggag gtagcacata catttaaaaa taggttaaaa taaagtgtta    600
ttttaattgg taggtggatc tgttggcacc aatgattatt cacggcatca agacccaggg    660
tgcccgtcag aagttctcca gcctctacat ctctcagttt atcatcatgt atagtcttga    720
tgggaagaag tggcagactt atcgaggaaa ttccactgga accttaatgg tcttctttgg    780
caatgtggat tcatctggga taaaacacaa tattttttaac cctccaatta ttgctcgata    840
catccgtttg cacccaactc attatagcat tcgcagcact cttcgcatgg agttgatggg    900
```

```
ctgtgattta aatagttgca gcatgccatt gggaatggag agtaaagcaa tatcagatgc      960
acagattact gcttcatcct actttaccaa tatgtttgcc acctggtctc cttcaaaagc     1020
tcgacttcac ctccaaggga ggagtaatgc ctggagacct caggtgaata atccaaaaga     1080
gtggctgcaa gtggacttcc agaagacaat gaaagtcaca ggagtaacta ctcagggagt     1140
aaaatctctg cttaccagca tgtatgtgaa ggagttcctc atctccagca gtcaagatgg     1200
ccatcagtgg actctctttt ttcagaatgg caaagtaaag gttttcagg gaaatcaaga      1260 ctccttcaca cctgtggtga actctctaga cccaccgtta ctgactcgct accttcgaat     1320 tcaccccag agtgggtgc accagattgc cctgaggatg gaggttctgg gctgcgaggc       1380
acaggacctc tactgaaagc tttacgtatg taattagtca tttaaaggga atgcctgaat     1440
actttaaaga attttggcag atttcagata ttggacaaac actcttagct tccacaaact    1500
taattccaaa aaataatttt tcacttatga gcaatagagt tattacggac atatcagcaa    1560
aaatgtagta gtgtcaaggc tcatagatga tagaaatgaa gagatgctgt attgatagaa    1620
atatgtgatt caggactgtg tggattaaat gcaggtctag atacgtagat aagtagcatg    1680
gcgggttaat cattaactac aaggaacccc tagtgatgga gttggccact ccctctctgc    1740
gcgctcgctc gctcactgag gccgggcgac caaaggtcgc ccgacgcccg gctttgccc      1800 gggcggcctc agtgagcgag cgagcgcgca gagagggagt ggccaa                    1846

<210> SEQ ID NO 45
<211> LENGTH: 2092
<212> TYPE: DNA
<213> ORGANISM: Artificial Sequence
<220> FEATURE:
<223> OTHER INFORMATION: pHMI-hF8-004-F8 correction genome including
      ITRs

<400> SEQUENCE: 45
ttggccactc cctctctgcg cgctcgctcg ctcactgagg ccgggcgacc aaaggtcgcc       60
cgacgcccgg ctttgcccgg gcggcctca gtgagcgagc gagcgcgcag agagggagtg      120
gccaactcca tcactagggg ttcctggagg ggtggagtcg tgacgtgaat tacgtcatag     180
ggttagggag gtcctgcata tggcggaaat tggctttggt ctgaggctga ggtgtgggca     240
aagcattagc ttatgtgggt ccattagctt atgtgagtcc acaaaaggtg tgtgtgtgtt     300
tgtgtgtatg tgtgtgtgtg tgtgtgtgtg tgtgtgtgta cgaaatgggg gctcaatgat     360
ttggtagtgg tttggtttgt caagaagcag gctgggaact caataagcat ctttccattc     420
atttctactg tgtatcccac agcttcacac acacatgcac atttcaacat tggtgactgc     480
ttcacttgca cacctaaggt aatgatggac acacctgtag caatgtagat tcttcctaag     540
ctaataatta gtttcaggag gtagcacata catttaaaaa taggttaaaa taaagtgtta     600
ttttaattgg taggtggatc tgttggcacc aatgattatt cacggcatca agacccaggg     660
tgcccgtcag aagttctcca gcctctacat ctctcagttt atcatcatgt atagtcttga     720
tgggaagaag tggcagactt atcgaggaaa ttccactgga accttaatgg tcttctttgg     780
caatgtggat tcatctggga taaaacacaa tattttttaac cctccaatta ttgctcgata    840
catccgtttg cacccaactc attatagcat tcgcagcact cttcgcatgg agttgatggg    900
ctgtgattta aatagttgca gcatgccatt gggaatggag agtaaagcaa tatcagatgc     960
acagattact gcttcatcct actttaccaa tatgtttgcc acctggtctc cttcaaaagc    1020
tcgacttcac ctccaaggga ggagtaatgc ctggagacct caggtgaata atccaaaaga   1080
```

```
gtggctgcaa gtggacttcc agaagacaat gaaagtcaca ggagtaacta ctcagggagt    1140
aaaatctctg cttaccagca tgtatgtgaa ggagttcctc atctccagca gtcaagatgg    1200
ccatcagtgg actctctttt ttcagaatgg caaagtaaag gttttcagg gaaatcaaga     1260 ctccttcaca cctgtggtga actctctaga cccaccgtta ctgactcgct accttcgaat    1320 tcaccccag agttgggtgc accagattgc cctgaggatg gaggttctgg gctgcgaggc     1380
acaggacctc tactgaaagc tttaccaagg cctctcgagc tctagaact atagtgagtc      1440 gtattacgta gatccagaca tgataagata cattgatgag tttggacaaa ccacaactag    1500
aatgcagtga aaaaaatgct ttatttgtga aatttgtgat gctattgctt tatttgtaac    1560
cattataagc tgcaataaac aagttaacaa caacaattgc attcatttta tgtttcaggt    1620
tcagggggag gtgtgggagg ttttttaagc tgtatgtaat tagtcattta aagggaatgc   1680
ctgaatactt taagaatttt tggcagattt cagatattgg acaaacactc ttagcttcca    1740
caaacttaat tccaaaaaat aattttttcac ttatgagcaa tagagttatt acggacatat   1800
cagcaaaaat gtagtagtgt caaggctcat agatgataga aatgaagaga tgctgtattg    1860
atagaaatat gtgattcagg actgtgtgga ttaaatgcag gtctagatac gtagataagt    1920
agcatggcgg gttaatcatt aactacaagg aaccctagt gatggagttg gccactccct     1980
ctctgcgcgc tcgctcgctc actgaggccg gcgaccaaa ggtcgcccga cgcccgggct     2040 tgcccgggc ggcctcagtg agcgagcgag cgcgcagaga gggagtggcc aa             2092

<210> SEQ ID NO 46
<211> LENGTH: 106
<212> TYPE: DNA
<213> ORGANISM: Artificial Sequence
<220> FEATURE:
<223> OTHER INFORMATION: truncated AAV2 5' ITR

<400> SEQUENCE: 46
ctgcgcgctc gctcgctcac tgaggccgcc cgggcaaagc ccgggcgtcg ggcgaccttt     60
ggtcgcccgg cctcagtgag cgagcgagcg cgcagagagg gagtgg                   106

<210> SEQ ID NO 47
<211> LENGTH: 25
<212> TYPE: DNA
<213> ORGANISM: Mus musculus

<400> SEQUENCE: 47
agtccatcca tgagatggaa acaaa                                          25

<210> SEQ ID NO 48
<211> LENGTH: 24
<212> TYPE: DNA
<213> ORGANISM: Mus musculus

<400> SEQUENCE: 48
acaagccaat tcttgaagta acag                                           24

<210> SEQ ID NO 49
<211> LENGTH: 26
<212> TYPE: DNA
<213> ORGANISM: Mus musculus

<400> SEQUENCE: 49
tcctctatat gatttgaact gtctcc                                         26
```

<210> SEQ ID NO 50
<211> LENGTH: 24
<212> TYPE: DNA
<213> ORGANISM: Artificial Sequence
<220> FEATURE:
<223> OTHER INFORMATION: SA2A_Vector_Set2 probe

<400> SEQUENCE: 50
ttctaacatg cggtgacgtg gagg                                              24

<210> SEQ ID NO 51
<211> LENGTH: 17
<212> TYPE: DNA
<213> ORGANISM: Artificial Sequence
<220> FEATURE:
<223> OTHER INFORMATION: SA2A_Vector_Set2 primer 1

<400> SEQUENCE: 51
cctagggccg ggattct                                                      17

<210> SEQ ID NO 52
<211> LENGTH: 20
<212> TYPE: DNA
<213> ORGANISM: Artificial Sequence
<220> FEATURE:
<223> OTHER INFORMATION: SA2A_Vector_Set2 primer 2

<400> SEQUENCE: 52
cctcttctct tcctcccaca                                                   20

<210> SEQ ID NO 53
<211> LENGTH: 20
<212> TYPE: DNA
<213> ORGANISM: Mus musculus

<400> SEQUENCE: 53
ggaagagctg gcactcagaa                                                   20

<210> SEQ ID NO 54
<211> LENGTH: 25
<212> TYPE: DNA
<213> ORGANISM: Artificial Sequence
<220> FEATURE:
<223> OTHER INFORMATION: F8_LeftA_R

<400> SEQUENCE: 54
cttaatattc ttggcatcct ccatg                                             25

<210> SEQ ID NO 55
<211> LENGTH: 21
<212> TYPE: DNA
<213> ORGANISM: Mus musculus

<400> SEQUENCE: 55
gctccagaat acacggttgt g                                                 21

<210> SEQ ID NO 56
<211> LENGTH: 23
<212> TYPE: DNA
<213> ORGANISM: Mus musculus

<400> SEQUENCE: 56
ccattgactg tgtgcatttt agg                                               23

```
<210> SEQ ID NO 57
<211> LENGTH: 20
<212> TYPE: DNA
<213> ORGANISM: Artificial Sequence
<220> FEATURE:
<223> OTHER INFORMATION: F8_RightA_F

<400> SEQUENCE: 57
atgaagcttg acggtggttc                                                    20

<210> SEQ ID NO 58
<211> LENGTH: 22
<212> TYPE: DNA
<213> ORGANISM: Mus musculus

<400> SEQUENCE: 58
tacgtagata agtagcatgg cg                                                 22

<210> SEQ ID NO 59
<211> LENGTH: 24
<212> TYPE: DNA
<213> ORGANISM: Mus musculus

<400> SEQUENCE: 59
atgataccca tttccctaga ttcc                                               24

<210> SEQ ID NO 60
<211> LENGTH: 21
<212> TYPE: DNA
<213> ORGANISM: Mus musculus

<400> SEQUENCE: 60
ggcaccactc ctgaaataca c                                                  21

<210> SEQ ID NO 61
<211> LENGTH: 143
<212> TYPE: DNA
<213> ORGANISM: Artificial Sequence
<220> FEATURE:
<223> OTHER INFORMATION: 3' ITR

<400> SEQUENCE: 61
aggaacccct agtgatggag ttggccactc cctctctgcg cgctcgctcg ctcactgagg        60
ccgggcgacc aaaggtcgcc cgacgcccgg gctttgcccg gcggcctcag tgagcgagc        120 gagcgcgcag agggagtg gcc                                                 143

<210> SEQ ID NO 62
<211> LENGTH: 37
<212> TYPE: DNA
<213> ORGANISM: Artificial Sequence
<220> FEATURE:
<223> OTHER INFORMATION: additional 37 bp for 3' ITR

<400> SEQUENCE: 62
gtagataagt agcatggcgg gttaatcatt aactaca                                 37

<210> SEQ ID NO 63
<211> LENGTH: 180
<212> TYPE: DNA
<213> ORGANISM: Artificial Sequence
<220> FEATURE:
<223> OTHER INFORMATION: 3' ITR with additional 37 bp sequence

<400> SEQUENCE: 63
```

-continued

```
gtagataagt agcatggcgg gttaatcatt aactacaagg aaccccctagt gatggagttg    60 gccactccct ctctgcgcgc tcgctcgctc actgaggccg ggcgaccaaa ggtcgcccga   120
cgcccgggct ttgcccgggc ggcctcagtg agcgagcgag cgcgcagaga gggagtggcc   180
```